US011820999B2

(12) United States Patent
Lahusen et al.

(10) Patent No.: US 11,820,999 B2
(45) Date of Patent: Nov. 21, 2023

(54) COMPOSITIONS AND METHODS FOR TREATING PHENYLKETONURIA

(71) Applicant: American Gene Technologies International Inc., Rockville, MD (US)

(72) Inventors: Tyler Lahusen, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 870 days.

(21) Appl. No.: 16/494,196

(22) PCT Filed: Apr. 2, 2018

(86) PCT No.: PCT/US2018/025733
§ 371 (c)(1),
(2) Date: Sep. 13, 2019

(87) PCT Pub. No.: WO2018/187231
PCT Pub. Date: Oct. 11, 2018

(65) Prior Publication Data
US 2020/0087682 A1     Mar. 19, 2020

Related U.S. Application Data

(60) Provisional application No. 62/491,118, filed on Apr. 27, 2017, provisional application No. 62/480,962, filed on Apr. 3, 2017.

(51) Int. Cl.
C12N 15/86      (2006.01)
A61K 35/76      (2015.01)
A61K 48/00      (2006.01)
C12N 9/02       (2006.01)

(52) U.S. Cl.
CPC .............. *C12N 15/86* (2013.01); *A61K 35/76* (2013.01); *C12N 9/0071* (2013.01); *C12Y 114/16001* (2013.01); *A61K 48/00* (2013.01); *C12N 2310/14* (2013.01); *C12N 2310/531* (2013.01); *C12N 2740/15021* (2013.01); *C12N 2740/15022* (2013.01); *C12N 2740/15032* (2013.01); *C12N 2740/15042* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 5,668,255 A | 9/1997 | Murphy | |
| 5,674,703 A | 10/1997 | Woo et al. | |
| 6,156,514 A | 12/2000 | Acevedo et al. | |
| 6,399,383 B1 | 6/2002 | Apt et al. | |
| 6,635,472 B1 | 10/2003 | Lauermann | |
| 7,371,542 B2 | 5/2008 | Ivanova et al. | |
| 8,124,752 B2 | 2/2012 | Bumcrot et al. | |
| 8,287,857 B2 | 10/2012 | Dudley et al. | |
| 8,993,532 B2 | 3/2015 | Hannon et al. | |
| 9,522,176 B2 | 12/2016 | DeRosa et al. | |
| 9,527,904 B2 | 12/2016 | Balazs | |
| 9,834,790 B1 | 12/2017 | Pauza et al. | |
| 9,834,791 B2 | 12/2017 | Zhang | |
| 9,914,938 B2 | 3/2018 | Pauza et al. | |
| 10,023,880 B2 | 7/2018 | Pauza et al. | |
| 10,036,038 B2 | 7/2018 | Pauza et al. | |
| 10,036,040 B2 | 7/2018 | Pauza et al. | |
| 10,137,144 B2 | 11/2018 | Pauza et al. | |
| 10,208,295 B2 | 2/2019 | DeRosa et al. | |
| 10,233,464 B2 | 3/2019 | Pauza et al. | |
| 2002/0168345 A1 | 11/2002 | Dong et al. | |
| 2003/0013196 A1 | 1/2003 | Engleman et al. | |
| 2003/0096787 A1 | 5/2003 | Perridcaudet et al. | |
| 2003/0119770 A1 | 6/2003 | Lai | |
| 2003/0138444 A1 | 7/2003 | Zavitz et al. | |
| 2003/0198620 A1 | 10/2003 | Ozawa et al. | |
| 2004/0142416 A1 | 7/2004 | Laipis et al. | |
| 2004/0161412 A1 | 8/2004 | Penn et al. | |
| 2004/0192629 A1 | 9/2004 | Xu et al. | |
| 2004/0214158 A1 | 10/2004 | Sethi et al. | |
| 2004/0248296 A1 | 12/2004 | Beresford et al. | |
| 2005/0019927 A1 | 1/2005 | Markus et al. | |
| 2005/0138677 A1 | 6/2005 | Pfister et al. | |
| 2006/0057553 A1 | 3/2006 | Aguilar-Cordova | |
| 2006/0183230 A1 | 8/2006 | Silla et al. | |

(Continued)

FOREIGN PATENT DOCUMENTS

BR              2515        3/2019
CN          101516365       8/2009
(Continued)

OTHER PUBLICATIONS

Charron, Gene Therapy for Phenylketonuria: Dominant-Negative Interference in a Recessive Disease. Dissertation. University of Florida. 2005. (Year: 2005).*
Ho et al., Translational Pediatrics, 2014, 3(2):49-62. (Year: 2014).*
Oh et al. "Lentiviral Vector Design Using Alternative RNA Export Elements," Retrovirology, vol. 4:38, pp. 1-10, (2007).
PCT; International Preliminary Report on Patentability dated Oct. 8, 2019 in the Application No. PCT/US2018/025733.
PCT; International Search Report and Written Opinion of the International Search Report dated Jul. 22, 2019 in the Application No. PCT/US2019/024410.
USPTO; Notice of Allowance dated Nov. 27, 2019 in the U.S. Appl. No. 13/333,882.

(Continued)

*Primary Examiner* — Nicole Kinsey White
(74) *Attorney, Agent, or Firm* — DLA Piper LLP (US)

(57) ABSTRACT

A lentiviral vector system for expressing a lentiviral particle is disclosed. The lentiviral vector system includes a therapeutic vector. The therapeutic vector comprises a phenylalanine hydroxylase (PAH) sequence for expressing at least one of PAH or a variant thereof, wherein the PAH sequence is truncated.

6 Claims, 16 Drawing Sheets

Specification includes a Sequence Listing.

(56) References Cited

U.S. PATENT DOCUMENTS

| | | |
|---|---|---|
| 2006/0246520 A1 | 11/2006 | Champagne et al. |
| 2007/0026521 A1 | 2/2007 | Colosi |
| 2007/0141679 A1 | 6/2007 | Sodroski |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodriguez et al. |
| 2010/0316676 A1 | 12/2010 | Sanders |
| 2011/0008803 A1 | 1/2011 | Stockwell et al. |
| 2011/0177155 A1 | 7/2011 | Peer et al. |
| 2011/0207226 A1 | 8/2011 | Ni et al. |
| 2012/0053223 A1 | 1/2012 | Benkirane et al. |
| 2012/0027725 A1 | 2/2012 | Galvin et al. |
| 2012/0114607 A1 | 5/2012 | Lai et al. |
| 2012/0034197 A1 | 8/2012 | Young et al. |
| 2012/0201794 A1 | 9/2012 | Chen et al. |
| 2013/0078276 A1 | 3/2013 | Robinson et al. |
| 2013/0090371 A1 | 4/2013 | Lu et al. |
| 2013/0142766 A1 | 6/2013 | Dodo et al. |
| 2013/0211380 A1 | 8/2013 | Aquino et al. |
| 2014/0105965 A1 | 4/2014 | Bancel et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kashara et al. |
| 2014/0248277 A1 | 9/2014 | Hoffman et al. |
| 2014/0336245 A1 | 11/2014 | Mingozzi et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2016/0289681 A1 | 10/2016 | Rossi |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0314041 A1 | 11/2017 | DeRosa et al. |
| 2017/0335344 A1 | 11/2017 | Pauza et al. |
| 2018/0010147 A1 | 1/2018 | Pauza |
| 2018/0142257 A1 | 5/2018 | Pauza |
| 2018/0142258 A1 | 5/2018 | Pauza |
| 2018/0161455 A1 | 6/2018 | Pauza |
| 2018/0177866 A1 | 6/2018 | Pauza |
| 2018/0195046 A1 | 7/2018 | Deng |
| 2018/0195050 A1 | 7/2018 | Szalay |
| 2018/0256624 A1 | 9/2018 | Pauza |
| 2018/0305716 A1 | 10/2018 | Pauza |
| 2018/0355032 A1 | 12/2018 | Roberts |
| 2019/0046633 A1 | 2/2019 | Pauza et al. |
| 2019/0062786 A1 | 2/2019 | Pauza et al. |
| 2019/0078096 A1 | 3/2019 | Lahusen et al. |
| 2019/0083523 A1 | 3/2019 | Pauza |
| 2019/0388456 A1 | 12/2019 | Pauza et al. |
| 2020/0063161 A1 | 2/2020 | Pauza |
| 2020/0109417 A1 | 4/2020 | Pauza et al. |
| 2020/0155590 A1 | 5/2020 | Zhennan |
| 2020/0181645 A1 | 6/2020 | Pauza |
| 2020/0318081 A1 | 10/2020 | Lahusen et al. |
| 2021/0047644 A1 | 2/2021 | Lahusen |

FOREIGN PATENT DOCUMENTS

| | | | |
|---|---|---|---|
| CN | 101679466 | 3/2010 | |
| CN | 101805750 | 8/2010 | |
| CN | 103184224 | 7/2013 | |
| CN | 104428009 A | 3/2015 | |
| CN | 105112370 | 12/2015 | |
| CN | 106459932 A | 2/2017 | |
| CN | 108883100 | 11/2018 | |
| EP | 1647595 | 4/2006 | |
| EP | 3402483 | 11/2018 | |
| EP | 3413926 | 12/2018 | |
| EP | 3426777 | 1/2019 | |
| EP | 3468617 | 4/2019 | |
| EP | 3468618 | 4/2019 | |
| EP | 3481418 | 5/2019 | |
| EP | 3481435 | 5/2019 | |
| IN | 201947000153 | 2/2016 | |
| JP | 2002506652 | 3/2002 | |
| JP | 2007-527240 | 9/2007 | |
| JP | 2008518591 | 6/2008 | |
| JP | 2008-538174 | 10/2008 | |
| JP | 2012508591 | 4/2012 | |
| JP | 2013-5300152 | 7/2013 | |
| JP | 2015-518838 | 7/2015 | |
| JP | 2016-502404 | 1/2016 | |
| JP | 2019509029 | 4/2019 | |
| WO | 199947691 | 9/1999 | |
| WO | WO 2001036620 | 5/2001 | |
| WO | 2002020554 | 3/2002 | |
| WO | 2003093436 | 11/2003 | |
| WO | 2004053137 | 6/2004 | |
| WO | 2005028634 | 3/2005 | |
| WO | 2005033282 | 4/2005 | |
| WO | 2006039721 | 4/2006 | |
| WO | 2006048215 | 5/2006 | |
| WO | 2007000668 | 1/2007 | |
| WO | 2007015122 | 2/2007 | |
| WO | 2007132292 | 11/2007 | |
| WO | 2007133674 | 11/2007 | |
| WO | 2008025025 | 2/2008 | |
| WO | 2008090185 | 7/2008 | |
| WO | 2009100928 | 8/2009 | |
| WO | 2009147445 | 12/2009 | |
| WO | 2010051521 | 5/2010 | |
| WO | 2010117974 | 10/2010 | |
| WO | 2010127166 | 11/2010 | |
| WO | 2011008348 | 1/2011 | |
| WO | 2011071476 | 6/2011 | |
| WO | 2011119942 | 9/2011 | |
| WO | 2012145624 | 2/2012 | |
| WO | 2012048303 | 4/2012 | |
| WO | 2012061075 | 5/2012 | |
| WO | 2013096455 | 6/2013 | |
| WO | 2014016817 | 1/2014 | |
| WO | 2014117050 | 7/2014 | |
| WO | 2014187881 | 11/2014 | |
| WO | 2015017755 | 2/2015 | |
| WO | 2015042308 | 3/2015 | |
| WO | 2015061491 | 4/2015 | |
| WO | 2015078999 | 6/2015 | |
| WO | 2015086854 | 8/2015 | |
| WO | WO2015164759 | 10/2015 | |
| WO | 2016046234 | 3/2016 | |
| WO | 2016061232 | 4/2016 | |
| WO | 2016069716 | 5/2016 | |
| WO | 2016200997 | 7/2016 | |
| WO | WO-2016122058 A1 * | 8/2016 | ............ C12N 15/79 |
| WO | 2016189159 | 12/2016 | |
| WO | 2017007994 | 1/2017 | |
| WO | 20170068077 | 4/2017 | |
| WO | 2017100551 | 6/2017 | |
| WO | 2017123918 | 7/2017 | |
| WO | 2017139065 | 8/2017 | |
| WO | 2017156311 | 9/2017 | |
| WO | 20170173453 | 10/2017 | |
| WO | 2017213697 | 12/2017 | |
| WO | 2017214327 | 12/2017 | |
| WO | 2018009246 | 1/2018 | |

(56) References Cited

FOREIGN PATENT DOCUMENTS

| WO | 2018009847 | 1/2018 |
| WO | 2018017882 | 1/2018 |
| WO | 2018126112 | 7/2018 |
| WO | 2018129540 | 7/2018 |
| WO | 20180148443 | 8/2018 |
| WO | 2018187231 | 10/2018 |
| WO | 2018232359 | 12/2018 |
| WO | 2019070674 | 4/2019 |
| WO | 2020097049 | 5/2020 |
| WO | 2020243717 | 12/2020 |

OTHER PUBLICATIONS

USPTO; Non-Final Office Action dated Jan. 13, 2020 in the U.S. Appl. No. 15/580,661.

Brites, C., M. Abrahao, P. Bozza, E. M. Netto, A. Lyra and F. Bahia (2018). "Infection by HTLV-1 Is Associated with High Levels of Proinflammatory Cytokines in HIV-HCV-Coinfected Patients." J Acquir Immune Defic Syndr 77(2): 230-234.

Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.

Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.

Futsch, N., R. Mahieux and H. Dutartre (2017). "HTLV-1, the Other Pathogenic Yet Neglected Human Retrovirus: From Transmission to Therapeutic Treatment." Viruses, 10, 1; doi: 10.3390/v10010001.

Gessain, A., F. Barin, J. C. Vernant, O. Gout, L. Maurs, A. Calender and G. de The (1985). "Antibodies to human T-lymphotropic virus type-I in patients with tropical spastic paraparesis." Lancet 2(8452): 407-410.

Gessain, A. and O. Cassar (2012). "Epidemiological Aspects and World Distribution of HTLV-1 Infection." Front Microbiol 3: 388.

Goncalves, D. U., F. A. Proietti, J. G. Ribas, M. G. Araujo, S. R. Pinheiro, A. C. Guedes and A. B. Carneiro-Proietti (2010). "Epidemiology, treatment, and prevention of human T-cell leukemia virus type 1-associated diseases." Clin Microbiol Rev 23(3): 577-589.

Kagdi, H., M. A. Demontis, J. C. Ramos and G. P. Taylor (2018). "Switching and loss of cellular cytokine producing capacity characterize in vivo viral infection and malignant transformation in human T-lymphotropic virus type 1 infection." PLOS Pathog 14(2): e1006861.

Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.

Macnamara, A., A. Rowan, S. Hilburn, U. Kadolsky, H. Fujiwara, et al. (2010). "HLA class I binding of HBZ determines outcome in HTLV-1 infection." PLOS Pathog 6(9): e1001117.

Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.

Martinez, M. P., J. Al-Saleem and P. L. Green (2019). "Comparative virology of HTLV-1 and HTLV-2." Retrovirology 16(1): 21.

Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.

Mosley, A. J., B. Asquith and C. R. Bangham (2005). "Cell-mediated immune response to human T-lymphotropic virus type I." Viral Immunol 18(2): 293-305.

Nagai, M. and M. Osame (2003). "Human T-cell lymphotropic virus type I and neurological diseases." J Neurovirol 9(2): 228-235.

Yamano, Y. and T. Sato (2012). "Clinical pathophysiology of human T-lymphotropic virus-type 1-associated myelopathy/tropical spastic paraparesis." Front Microbiol 3: 389.

Nishioka, K., I. Maruyama, K. Sato, I. Kitajima, Y. Nakajima and M. Osame (1989). "Chronic inflammatory arthropathy associated with HTLV-I." Lancet 1(8635): 441.

Osame, M., K. Usuku, S. Izumo, N. Ijichi, H. Amitani, et al. (1986). "HTLV-I associated myelopathy, a new clinical entity." Lancet 1(8488): 1031-1032.

Poiesz, B. J., F. W. Ruscetti, A. F. Gazdar, P. A. Bunn, J. D. Minna and R. C. Gallo (1980). "Detection and isolation of type C retrovirus particles from fresh and cultured lymphocytes of a patient with cutaneous T-cell lymphoma." Proc Natl Acad Sci U S A 77(12): 7415-7419.

Poiesz, B. J., F. W. Ruscetti, J. W. Mier, A. M. Woods and R. C. Gallo (1980). "T-cell lines established from human T-lymphocytic neoplasias by direct response to T-cell growth factor." Proc Natl Acad Sci U S A 77(11): 6815-6819.

Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.

Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.

Uchiyama, T., J. Yodoi, K. Sagawa, K. Takatsuki and H. Uchino (1977). "Adult T-cell leukemia: clinical and hematologic features of 16 cases." Blood 50(3): 481-492.

Dickler, H. B., et al. (1973). "Lymphocyte binding of aggregated IgG and surface Ig staining in chronic lymphocytic leukaemia." Clin Exp Immunol 14(1): 97-106.

USPTO; Notice of Allowance dated May 18, 2020 in the U.S. Appl. No. 16/083,384.

USPTO; Final Office Action dated Jun. 2, 2020 in the U.S. Appl. No. 15/580,661.

USPTO; Non-Final Office Action dated Jun. 1, 2020 in the U.S. Appl. No. 16/530,908.

CN; 1st Office Action in the CN Application No. 20170017712.6 dated May 8, 2020.

EPO; Office Action in the EPO Application No. 16808223.8 dated May 11, 2020.

Nada et al., "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.

Benyamine et al., "BTN3A molecules considerably improve Vγ9Vδ2T cells-based immunotherapy in acute myeloid leukemia," Oncolmmunology, vol. 5, No. 10, 10 pages, (Oct. 2, 2016), E1146843 *the whole document*.

Harly et al., "Key implication of CD277/butyrophilin-3 (BTN3A) in cellular stress sensing by a major human γδ T-cell subset," American Society of Hematology, vol. 120, No. 11, (Sep. 13, 2012), pp. 2269-2279, XP055081172, ISSN: 0006-4971, DOI: 10.1182/blood-2012-05-430470 *the whole document*.

Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.

USPTO; Notice of Allowance dated Feb. 10, 2021 in the U.S. Appl. No. 16/943,800.

USPTO; Non-Final Office Action dated Feb. 19, 2021 in the U.S. Appl. No. 15/580,661.

USPTO; Final Office Action dated Feb. 26, 2021 in the U.S. Appl. No. 16/312,056.

USPTO; Corrected Notice of Allowance dated Mar. 3, 2021 in the U.S. Appl. No. 16/687,525.

USPTO; Non-Final Office Action dated Mar. 12, 2021 in the U.S. Appl. No. 16/563,738.

CN; 1st Office Action in the CN Application No. 202010396594.8 dated Jan. 15, 2021.

EP; Supplementary Search Report in the EP Application No. 18817253 dated Feb. 10, 2021.

JP; Office Action in the JP Application No. 2018-547354 dated Feb. 16, 2021.

(56) References Cited

OTHER PUBLICATIONS

JP; Office Action in the JP Application No. 2018-541270 dated Jan. 8, 2021.
USPTO; Notice of Allowance dated Jan. 26, 2021 in the U.S. Appl. No. 16/593,882.
Yang et al., "Construction of PARP-1 gene silencing cell lines by lentiviral-mediated RNA interference," School of Public Health, Guangdong Medical College, Abstract (2006).
Zhaobing Ding et al., "Liver-Directed, AAV- and Lentivirus-Mediated Gene Therapy in the Phenylketonuria Mouse Model Pah-enu2", Molecular Therapy, vol. 11, Supp. 1. (May 2005) XP055751452.
Ledley et al., "Retroviral-mediated gene transfer of human phenylalanine hydroxylase into NIH 3T3 and hepatoma cells", Proceedings of the National Academy of Sciences, vol. 83, No. 2. (Jan. 1, 1986), pp. 409-413, XP002583115.
Ledley et al., "Molecular biology of phenylalanine hydroxylase and phenylketonurina", Trends in Genetics, Elsevier Science Publishers B.V. Amsterdam, NL, vol. 1. (Jan. 1, 1985), pp. 309-313, XP025943064.
USPTO; Notice of Allowance dated Jan. 13, 2021 in the U.S. Appl. No. 16/687,525.
EP; Supplementary Search Report in the EP Application No. 18781288.8 dated Dec. 8, 2020.
JP; Final Office Action in the JP Application No. 2018-536892 dated Nov. 16, 2020.
Quan Jun-Jie et al., "Parp3 interacts with FoxM1 to confer glioblastoma cell radio resistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/S13277-015-3554-4 [retrieved on Jun. 4, 2015] *whole document*.
Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/ J.Ymthe.2005.11.012 *the whole document*.
Yun Jong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119 *the whole document*.
Lang Yoo et al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/ J. BBRC.2011.04.070 [retrieved on Apr. 22, 2011] *whole document*.
Tae-In Kam et al., "Poly (ADP-ribose) derived pathologic [alpha]-synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407 *whole document*.
Olsen A.L. and Feany M.B., "PARP Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020] *the whole document*.
Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.
FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.
Kathleen Van Craenenbroeck et al., "Episomal vectors for gene expression in mammalian cells", Eur J. Biochem, vol. 267, p. 5665-5678, Jul. 14, 2000.
USPTO; Non-Final Office Action dated Mar. 16, 2020 in the U.S. Appl. No. 16/083,384.

EPO; Extended European Supplemental Search Report dated Mar. 11, 2020 in the Application No. 17831904.2.
JP; Japanese Office Action in the Application No. 2017-564550 dated Mar. 18, 2020.
USPTO; Restriction Requirement dated Jan. 29, 2020 in the U.S. Appl. No. 16/312,056.
EPO; Supplementary European Search Report dated Dec. 19, 2019 in the Application No. 16904834.5.
EPO; Supplementary European Search Report dated Dec. 19, 2019 in the Application No. 17810976.5.
Vargas, J. Jr. et al., "Conditionally replicating lentiviral-hybrid episomal vectors for suicide gene therapy," Antiviral Res. Dec. 2008 vol. 80 No. 3, pp. 288-294.
Thompson et al., "Alkylamines cause Vγ9Vδ2 T-cell activation and proliferation by inhibiting the mevalonate pathway," Blood, Jan. 15, 2006, vol. 107, pp. 651-654.
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, Jul. 1, 2014, vol. 210, pp. 99-110.
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.
{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&RID=H3FCKA00014; p. 1.
Tebas, P. et al, "Antiviral effects of autologous CD4 T cells genetically modified with a conditionally replicating lentiviral vector expressing long antisense to HIV," Blood, 2013, vol. 121, No. 9, pp. 1524-1533.
Tebas, p. et al., "Gene Editing of CCR5 in Autologous CD4 T Cells of Persons Infected with HIV," The New England Journal of Medicine, vol. 370 (10), pp. 901-910, Mar. 6, 2014.
Li et al., "Reduced Expression of the Mevalonate Pathway Enzyme Farnesyl Pyrophosphate Synthase Unveils Recognition of Tumor Cells by Vγ2Vδ2 T Cells," J. of Immunology, 2009, vol. 182, pp. 8118-8124.
Wang et al., "Indirect Stimulation of Human Vγ2Vδ2 T Cells through Alterations in Isoprenoid Metabolism," J. of Immunology, vol. 187 pp. 5099-5113, (Nov. 15, 2011).
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).
Dieli et al., "Targeting Human γδ T Cells with Zoledronate and Interleukin-2 for Immunotherapy of Hormone-Refractory Prostate Cancer, " Europe PMC Funders Group, Cancer Research, vol. 67(15), pp. 7450-1451, (Aug. 1, 2007).
GenBank Accession No. S60559 "(long control region) [human papillomavirus, type 16, Genomic, 860 nt]" May 7, 1993 [located online Nov. 21, 2017 at https://ncbi.nlm.nih.gov/nuccore/S60559] entire DNA sequence.
GenBank Accession No. JG619773, MNESC1NG-T3-001_L15_6FEB2009_054 MNESC1NG cell culture from Mahonia nervosa Berberis nervosa cDNA, mRNA sequence, Feb. 13, 2014 (online). [Retrieved on Dec. 5, 2017]. Retrieved from the internet:<URL: https://www.ncbi.nlm.nih.gov/nucest/JG619773 > entire document.
Moser et al., "γd T cells: novel initiators of adaptive immunity," Immunological Reviews, vol. 215, pp. 89-102 (Feb. 2, 2007).
Capietto, A. H. et al., "Stimulated γδ T Cells Increase the in Vivo Efficacy of Trastuzumab in HER-2+ Breast Cancer," J Immunology, vol. 187(2), pp. 1031-1038, (2011).

(56) References Cited

OTHER PUBLICATIONS

Chen, Z. and M. S. Freedman, "CD16+ γδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Couzi, L. et al., "Antibody-Dependent Anti-Cytomegalovirus Activity of Human γδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+ γδT Cells," OncoImmunology, vol. 5(1), pp. e1025194, (2016).
Gertner-Dardenne, J. et al., "Bromohydrin pyrophosphate enhances antibody-dependent cell-mediated cytotoxicity induced by therapeutic antibodies," Blood 113(20): 4875-4884, (2009).
Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Schiller, C. B. et al., "CD19-Specific Triplebody SPM-1 Engages NK and γδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.
Twitty et al., "Retroviral Replicating Vectors Deliver Cytosine Deaminase Leading to Targeted 5-Fluorouracil-Mediated Cytotoxicity in Multiple Human Cancer Types," Human Gene Therapy Methods, 27(1), pp. 17-31, Feb. 1, 2016.
Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).
Fusetti, et al., "Structure of Tetrameric Human Phenylalanine Hydroxylase and Its Implications for Phenylketonuria," J. Bio. Chem., vol. 273, No. 27, pp. 16962-16967 (1998).
Hafid et al., "Phenylketonuria: A Review of Current and Future Treatments," Translational Pediatrics, vol. 4(4), pp. 304-317, (2015).
Blau et al., "Phenylketonuria," The Lancet, vol. 376(9750), pp. 1417-1427, (2010).
Chandler et al., "Vector Design Influences Hepatic Genotoxicity After Adeno-Associated Virus Gene Therapy," Journal of Clinical Investigation, vol. 125(2), pp. 870-880, (2015).
Christophersen et al., "A Technique of Transumbilical Portal Vein Catheterization in Adults," The Archives of Surgery, vol. 95(6), pp. 960-963, (1967). (Abstract Only).
Bartholome, "Genetics and Biochemistry of the Phenylketonuria-Present State," Human Genetics, vol. 51(3), pp. 241-245, (1979).
Donsante et al., "AAV Vector Integration Sites in Mouse Hepatocellular Carcinoma," Science, vol. 317(5837, p. 477, (2007).
Eisensmith et al., "Multiple Origins for Phenylketonuria in Europe," American Journal of Human Genetics, vol. 51(6), pp. 1355-1365, (1992).
Fisher et al., "The Inhibition of Phenylalanine and Tyrosine Hydroxylases by High Oxygen Levels," Journal of Neurochemistry, vol. 19(5), pp. 1359-1365, (1972). (Abstract Only).
Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).
Guldberg et al., "Aberrant Phenylalanine Metabolism in Phenylketonuria Heterozygotes," Journal of Inherited Metabolic Disease, vol. 21(4), pp. 365-372, (1998).
Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).
Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).
Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).
Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).
Nault et al., "Adeno-Associated Virus Type 2 as an Oncogenic Virus in Human Hepatocellular Carcinoma," Molecular & Cellular Oncology, vol. 3(2), p. e1095271, (2016).
Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).
Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).
Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLOS One, vol. 11(8), p. e0160892, (2016).
Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).
Blick et al., "Cyclophosphamide Enhances SB-728-T Engraftment to Levels Associated with HIV-RNA Control," CROI Conference on Retroviruses and Opportunistic Infections, Boston, Massachusetts, p. 141, (2014), (Abstract Only).
De Rose et al., "Safety, Immunogenicity and Efficacy of Peptide-Pulsed Cellular Immunotherapy in Macaques," Journal of Medical Primatology, vol. 27(2), pp. 69-78, (2008).
Smith et al., "Developments in HIV-1 Immunotherapy and therapeutic Vaccination," F1000Prime Reports, vol. 6, p. 42, (2014).
Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).
Nowacki et al., "The PAH Mutation Analysis Consortium Database: Update 1996," Nucleic Acid Research, vol. 25(1), pp. 139-142, (Jan. 1, 1997).

(56) References Cited

OTHER PUBLICATIONS

Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).
Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of Macaca Nemestrina CD4+ T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cytoplasm- or Lysosome-Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).
Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).
GenBank Sequence M65141.1 Retrieved from the Internet <URL: https://www.ncbi.ntm.nih.gov/nuccore/M65141.1. Especially Sequence, nt 301-420, (Retrieved Mar. 31, 2019).
Hee Yeon Kim., "Farnesyl diphosphate synthase is important for the maintenance of glioblastoma stemness," Experimental & Molecular Medicine, (2018).
Hong Wang., "Indirect Stimulation of Human V2V2 Cells Through Alterations in Isoprenoid Metabolism," The Journal of Immunology, (2011).
Z. Li, "Inhibition of farnesyl pyrophosphate synthase prevents angiotensin II-induced cardiac fibrosis in vitro," Clinical & Experimental Immunology, (2014).

Xiaofeng Jiang, "A novel EST-derived RNAi screen reveals a critical role for farnesyl diphosphate in B2-adrenerigic receptor internalization and down-regulation," The FASEB Journal, vol. 26, pp. 1-13(1995).
Jian Yang, "Lentiviral-Mediated Silencing of Farnesyl Pyrophosphate Synthase through RNA Interference in Mice," Biomed Research International, vol. 2015, Article ID 914026, 6 pages, (2015).
Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).
Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report dated Jul. 14, 2017 in Application No. PCT/US2017/013024.
PCT: Written Opinion dated Jul. 14, 2017 in application No. PCT/US2017/013024.
PCT: International Search Report dated May 29, 2018 in Application No. PCT/US2018/012998.
PCT: Written Opinion dated May 29, 2018 in Application No. PCT/US2018/012998.
PCT; International Search Report dated Sep. 24, 2018 in Application No. PCT/US2018/025733.
PCT; Written Opinion dated Sep. 24, 2018 in Application No. PCT/US2018/025733.
PCT; International Search Report dated Nov. 9, 2018 in Application No. PCT/US2018/037924.
PCT; Written Opinion dated Nov. 9, 2018 in Application No. PCT/US2018/037924.
PCT; Invitation to Pay Additional Fees in Application No. PCT/US2018/053919 dated Feb. 22, 2019.

(56) References Cited

OTHER PUBLICATIONS

PCT; Written Opinion dated Apr. 12, 2019 in Application No. PCT/US2018/053919.
PCT; International Search Report dated Apr. 12, 2019 in Application No. PCT/ US2018/053919.
PCT; International Search Report dated Jul. 22, 2019 in the Application No. PCT/US2019/24410.
PCT; Written Opinion of the International Search Report dated Jul. 22, 2019 in the Application No. PCT/US2019/24410.
PCT; International Preliminary Report on Patentability dated Jul. 9, 2019 in the Application No. PCT/US2018/012998.
USPTO; Notice of Allowance dated Oct. 13, 2017 in U.S. Appl. No. 14/706,481.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Feb. 22, 2018 in U.S. Appl. No. 13/333,882.
USPTO; Notice of Allowance dated Mar. 26, 2018 in U.S. Appl. No. 15/668,223.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
USPTO; Non-Final Office Action dated Jun. 15, 2018 in U.S. Appl. No. 15/904,131.
USPTO; Requirement for Restriction dated Jul. 12, 2018 in U.S. Appl. No. 15/736,284.
USPTO; Invitation to Pay Additional Fees and, Where Applicable, Protest Fee dated Jul. 17, 2018 in Application No. PCT/US2018/25733.
USPTO; Requirement for Restriction dated Aug. 3, 2018 in U.S. Appl. No. 16/011,550.
USPTO; Notice of Allowance dated Aug. 10, 2018 in U.S. Appl. No. 15/904,131.
USPTO; Final Office Action dated Aug. 27, 2018 in U.S. Appl. No. 13/333,882.
USPTO; Non-Final Office Action dated Sep. 19, 2018 in U.S. Appl. No. 16/011,550.
USPTO; Invitation to Pay Additional Fees and, Where Applicable, Protest Fee dated Sep. 11, 2018 in Application No. PCT/US2018/37924.
USPTO; Non-Final Office Action dated Oct. 19, 2018 in U.S. Appl. No. 15/736,284.
USPTO; Notice of Allowance dated Oct. 31, 2018 in U.S. Appl. No. 16/011,550.
USPTO; Advisory Action dated Nov. 16, 2018 in U.S. Appl. No. 13/333,882.
USPTO; Non-Final Office Action dated Dec. 31, 2018 in U.S. Appl. No. 16/182,443.
USPTO; Non-Final Office Action dated Apr. 18, 2019 in U.S. Appl. No. 13/333,882.
USPTO; Final Office Action dated May 2, 2019 in U.S. Appl. No. 15/736,284.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Non-Final Office Action dated May 24, 2019 in U.S. Appl. No. 16/218,010.
USPTO; Notice of Allowance dated Jun. 18, 2019 in the U.S. Appl. No. 16/182,443.
USPTO; Notice of Allowance dated Jul. 3, 2019 in U.S. Appl. No. 16/182,443.
USPTO; Restriction Requirement dated Jul. 12, 2019 in the U.S. Appl. No. 15/736,284.
USPTO; Advisory Action dated Jul. 23, 2019 in the U.S. Appl. No. 15/736,284.
USPTO; Notice of Allowance dated Aug. 14, 2019 in the U.S. Appl. No. 16/008,991.
USPTO; Notice of Allowance dated Sep. 25, 2019 in the U.S. Appl. No. 16/218,010.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
EPO; Extended Search Report dated Dec. 12, 2018 in EP Application No. 16808223.8.
EPO; Extended Search Report dated Dec. 11, 2018 in EP Application No. 16822021.8.
EPO; Extended Search Report dated Jun. 6, 2019 in EP Application No. 17739028.3.
EPO; European Search Report dated Aug. 12, 2019 in the EP Application No. 17764128.9.
EPO; Supplementary European Search Report dated Sep. 6, 2019 in the Application No. 17750547.6.
Bergvall et al. "The E1 proteins", Virology 445; p. 35-56, (Year:2013).
McBride, A., "The Papillomavirus E2 proteins", Virology 445: p. 57-79, (Year: 2013).
Chiang C-m et al., "Viral E1 and E2 proteins support replication of homologous and heterologous papillomaviral origins." PNAS 89: p. 5799-5803, (Year: 1992).
Krajinovic et al., "Sequencing data on the long control region of human papillomavirus type 16." Journal of General Virology 72:2573-2576, (Year: 1991).
Seedorg et al., "Human Papillomavirus type 16 DNA sequence." Virology 145: p. 181-185, (Year: 1985).
Jaalouk, et al. "A Self-inactivating retrovector incorporating the IL-2 promoter for activation-induced transgene expression engineered t-cells," Virology Journal: p. 1-12, (Year: 2006).
USPTO; Non-Final Office Action dated Sep. 22, 2020 in the U.S. Appl. No. 16/308,373.
Cronin et al., "Altering the Tropism of Lentiviral Vectors through Pseudotyping", Curr Gene Ther, Aug. 2005, vol. 5(4), pp. 687-398.
Cannon et al., "Pseudotype-Dependent Lentiviral Transduction of Astrocytes or Neurons in the Rat Substantia Nigra", Experimental Neurology, vol. 228, (Year: 2011), pp. 41-52, doi:10.1016/J.expneurol.2010.10.016.
USPTO; Non-Final Office Action dated Nov. 18, 2020 in the U.S. Appl. No. 16/318,345.
USPTO; Restriction Requirement dated Nov. 19, 2020 in the U.S. Appl. No. 16/593,882.
USPTO; Non-Final Office Action dated Nov. 25, 2020 in the U.S. Appl. No. 16/943,800.
USPTO; Notice of Allowance dated Dec. 2, 2020 in the U.S. Appl. No. 16/076,655.
USPTO; Restriction Requirement dated Dec. 8, 2020 in the U.S. Appl. No. 16/563,738.
Lee et al., "Lentiviral delivery of short hairpin RNAs protects CD4 cells from multiple clades and primary isolates of HIV." Blood, 2005, vol. 106(3):818-826. (Year: 2005).
Choi et al., "Multiplexing Seven miRNA-Based shRNAs to Suppress HIV Replication." Molecular Therapy, 2015, vol. 23(2):310-320. Supplementary materials.
Spartevello et al., Development of Lentiviral Vectors Simultaneously Expressing Multiple siRNAs Against CCR5, vif and tat/rev Genes for an HIV-1 Gene Therapy Approach, Molecular Therapy—Nucleic Acids, 2016, vol. 5:1-12.
USPTO; Restriction Requirement dated Jun. 15, 2020 in the U.S. Appl. No. 16/308,373.
USPTO; Restriction Requirement dated Jun. 26, 2020 in the U.S. Appl. No. 16/318,345.
USPTO; Office Action dated Jul. 6, 2020 in the U.S. Appl. No. 16/312,056.

(56) References Cited

OTHER PUBLICATIONS

JP; Japanese Office Action in the Application No. 2019-500475 dated Jun. 12, 2020.
USPTO; Non-Final Office Action dated Oct. 29, 2020 in the U.S. Appl. No. 15/736,284.
JP; Japanese Office Action in the JP Application No. 2018-563892 dated Oct. 14, 2020.
PCT; International Search Report and Written Opinion in the PCT Application No. PCT/US2019/059828 dated Feb. 14, 2020.
PCT International Search Report and Written Opinion in International Application No. PCT/US2020/035584, dated Sep. 4, 2020, 10 pages.
USPTO; Notice of Allowance dated Jul. 10, 2020 in the U.S. Appl. No. 16/530,908.
USPTO; Final Office Action dated Jul. 27, 2020 in the U.S. Appl. No. 16/076,655.
JP; Japanese Office Action in the Application No. 2018-536892 dated Jun. 26, 2020.
Harding et al., "Complete correction of hyperphenylalaninemia following liver-directed, recombinant AAV2/8 vector-medicated gene therapy in murine phenylketonuria", Gene Ther., Mar. 2006, 13(5):457-462.
JP Office Action in Japanese Application No. 2020-518812, dated Aug. 25, 2022, 13 pages (with English translation).
U.S. Restriction Requirement in U.S. Appl. No. 16/652,867, dated Sep. 9, 2022, 9 pages.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
USPTO; Restriction Requirement dated Oct. 22, 2019 in the U.S. Appl. No. 15/580,661.
USPTO; Restriction Requirement dated Nov. 4, 2019 in the U.S. Appl. No. 16/076,655.
USPTO; Notice of Allowance dated Oct. 29, 2019 in the U.S. Appl. No. 13/333,882.
USPTO; Restriction Requirement dated Nov. 7, 2019 in the U.S. Appl. No. 16/083,384.
Wang et al., "HIV Vaccine Research: The Challenge and the Way Forward," Journal of Immunology Research, vol. 2015, Article ID 503978, 5 pages.
Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).
Briz et al., "Validation of Generation 4 Phosphorus-Containing Polycationic Dendrimer for Gene Delivery Against HIV-1," Current Medical Chemistry, vol. 19, p. 5044-5051, (2012).
Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.
JP; Japanese Office Action in the Application No. 2017-567175 dated Jun. 15, 2020.
EPO; Extended European Search Report in the Application No. 18736295.9 dated Aug. 20, 2020.
Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).
USPTO; Non-Final Office Action dated Feb. 21, 2020 in the U.S. Appl. No. 16/076,655.
EPO; Extended European Supplementary Search Report dated Feb. 6, 2020 in the Application No. 17825011.4.
EPO; Extended European Supplementary Search Report dated Feb. 6, 2020 in the Application No. 17824652.6.
CN Office Action in Chinese Application No. 201880077904, dated Feb. 19, 2023, 17 pages (with English translation).
*Homo sapiens* phenylalanine hydroxylase (PAH) mRNA, complete cds, GenBank: U49897.1, Publication [online], Oct. 2, 1997, https://www.ncbi.nlm.nih.gov/nuccore/2462721, 2 pages.
Bancroft et al., "Characterization of the Alu-rich 5'-flanking region of the human prothrombin-encoding gene: identification of a positive cis-acting element that regulates liver-specific expression", Geen, Apr. 1990, 95:253-260.
Chow et al., "Characterization o a Novel Liver-specific Enhancer in the Human Prothrombin Gene", The Journal of Biological Chemistry, Oct. 1991, 266(28):18927-18933.
JP Office Action in Japanese Application No. 2020-518812, dated Feb. 21, 2023, 9 pages (with English translation).
KR Office Action in Korean Application No. 10-2019-7032224, dated Feb. 1, 2023, 14 pages (with English translation).
U.S. Non-Final Office Action in U.S. Appl. No. 16/652,867, dated Feb. 10, 2023, 45 pages.
EP; Supplementary Search Report in the EP Application No. 20814445.1 dated May 9, 2023.
JP Office Action in Japanese Application No. 2019-554397, dated Nov. 21, 2022, 8 pages (with English translation).
CN Office Action dated Sep. 16, 2023 issued in Application No. 201880077904.0.
U.S. Office Action dated Sep. 26, 2023 issued in U.S. Appl. No. 16/652,867.

* cited by examiner

GGCACGAGGTACCTGAGGCCTAAAAAGCCAGAGACCTCACTCCCGGGAGCCAGCATGTCCACTGGGGTCCTGCGGAAAACCAGGCTTGGG
CAGGAAACTCTCTGACTTGGACAGGAAACAAGCTATATTGAAGACAACTGCAATCAAAATGGTGCCATATCACTGATCTTCTCACTCAAAGAA
GAAGTTGGTGCATTGGCCAAAGTATTGCGCTTATTGAGGAGAATGATGTAAACCTGACCCACATTGAATCTAGACCTTCTCGTTTAAAGAAA
GATGAGTATGAATTTTCACCCATTTGGATAAACGTAGCCTGCCTGCTCTGACAAACATCATCAAGAGTCTTGAGGCATGACATTGGTGCCACTG
TCCATGAGCTTTCACGAGATAAGAAAGAAGAAGAGAAAGACACAGTGCCCTGGTTCCCAAGAACCATTCAAGAGCTGGACAGATTTGCCAATCAGATTCTCA
GCTATGGAGCGGAACTGGATGCTGACCACCCTGGTTTAAAGATCCTGTGTACCGTGCAAGACGGAAGCAGTTTGCTGACATTGCCTACAACT
ACCGCCATGGGCAGCCATCCCTCGAGTGGAATACATGGGAAGAAAGAAAACATGGGCACAGTGTTCAAGACTCTGAAGTCCTTGTAT
AAAACCCATGCTGCTATGAGTACACATTTTCCACTTCTTGAAAAGTACTGTGGCTTCCATGGAAGATAACATTCCCCAGCTGGAAGACGT
TTCTCAGTTCCTGCAGACTTGCCACTGGTTTCCGCCTGTTTCCGCCTGTAGCTGCCTGCTGCTTCTCTCGGATTTCTGGGTGGCCTTCCGAG
TCTTCCACTGCACACAGTACATCAGACATGGATCCAAGCCATGTATACCCCGAAGCCCATGTATACCCCGAACCTGCACATCTGCACCTGCGAGCTGTGGGACATGTGCCCTT
GTTTCAGATGCAGCTTTGCCCAGTTTCCCAGGAAATTGGCCTGCCTCTCTGGGTGCACCTGATGAATACATTGAAAAGCTCGCCACAATTT
ACTGGTTTACTGTGGAGTTGGGCTCTGCAAACAAGGAGACTCCATAAAGGAGACTCCATAAAGGCATATGGTGCTGGGCTCCTGTCATCCTTGGTGAATTACAGT
ACTGCTTATCAGAGAAGCCAAAGTCTCTCCCCTGGAGCTGGAAGAAGACAGCCATCCAAAATTACACTGTCACGGAGTTCAGCCTGTATTA
CGTGGCAGAGAGTTTTAATGATGCCAAGGAGAAAGTAAGGAACTTGCTGCCACAATACCTCGGCCCTTCTCAGTTGCTACGACCATACAC
CCAAAGGATTGAGGTCTTGGACAATACCCAGCAGCTTAGAATCTGGCTGATTCATTAACAGTGAATTGGAATCCTTGCAGTGCCCTCCAG
AAAATAAAGTAAAGCCATGGACAGAATGGTCTGTCAGCTGTGAATCTGTGATCTGTGTAACAAGAGAAATGGGAATCACAAAATAAGTCAACTATTTCTTCATCAGAAAAGTCGA
AAAGCAAACCTTAATTGAAATAAGCTTACAAGATCCTTAAATCTTTACAAGATGGAGAAACAACAATAAGTCAAATAATCTGAAATGACAGGATA
TGAGTACATACTCAAGAGCATAAGAGCATAAGATTAATGGTAAATTAAATTTGGGGTCATCTTGATTTGAGAGATGATAATCCCATACTCTCAATTGAGTAAATCAGT
AATCTGTGCATTTCATCAGATGTAAAACCAAGACTGCTTCATCAAGACTTCATTGGGGACCTGCATTCAAGCTTCATTCAGCTTAATATATGCTTTGCAGAGAACTCATAAGGAGCATA
TAAGGCTAAATGTAAAACCAAGACTGTCTATTGTACCTAAGTAAATTTCTTAAGTCAGAAGCCATTAAGTCAGAAGCCATTAAAATAGTACAAGCATTGAACTTCTATCATGAAGTTTATTTTTATTTTAGT
TAACTATGATTCAATTACTACTTGTTATTGTAAGTAAATTTCTTAAGTCAGAAGCCATTAAGTAAATTTCTTAAGTCAGAAGCCATTAAAATAGTACAAGCATTGAACTCT
TTAGTATTATATTATATAAAAACATTTTTGTATGTTTTATTGTAATCATAAAATACTGCTGTATAAGGTAATAAAACTGCACCTAATCCCA
TAACTTCCAGTATCATTTCCAATTAATTATCAAGTCTGTTTGGGAAACACTTGAGGACATTTATGATGCAGAGATGTTGACTAAAGGCT
TGGTTGGTAGATATTCAGGAAATGTTCACTGAAATGTTCACTGAATAAATAAGTAAATACATTATTGAAAAGCAAATCTGTATAAATGTGAAATTTATTTGT
ATTAGTAATAAAACATTAGTAGTTTAAACAAAAAAAAAAAAAAAAAAAAAAAAACTGACTCTAGATT

Figure 5

```
GGCACGAGGTACCTGAGGCCCTAAAAAGCCAGAGACCTCACTCCCGGGGAGCCAGCATGTCCACTGCGGTCTGGAAAACCC
AGGCTTGGGCAGGAGAAACTCTCTGACTTTGGACAGGAGAAACAAGCTATATTGAAGACAACTGCAATCAAAATGGTGCCATATCACT
GATCTTCTCACTCAAGAAGAAGAAGTTGGTGCATTGGCCAAAGTATTGCGCTTATTTGAGGAGAATGATGTAAACCTGACCACAT
TGAATCTAGACCTTCTCGTTAAAGAAGATGAGTAGTATGAATTTTTCACCCATTTGGATAAACGTAGCCTGCCTGCTCTGACAAAC
ATCATCAAGATCTTGAGGCATGACATTGGTGCCACTGTCCATGAGCTTTCACGAGATAAGAAGAAAGACACAGTGCCCTGGTTC
CCAAGAACCATTCAAGAGCTGGACAGATTTGCCAATCAGATTCTCAGCTATGGAGCGGAACTGGATGCTGACCACCCTGGTTT
AAAGATCCTGTGTGACCGTGCAAGACGGAAGCAGTTTGCTGACATTGCCTACAACTACCGCCATGGGCAGCCATCCCTGAGTG
GAATACATGGAGGAAGAAAAGAAAACATGGGGCACAGTTCAAGACTGTTCAAGATCTGAAGTCCTTGTATAAACCATGCTGTATGA
GTACAATCACATTTTCCACTTCTTGAAAAGTACTGTGGCTTCCATGAAGATAACATTCCCAGCTGGAAGACGTTTCTCAGTTCC
TGCAGACTTGCACTGGTTTCCGCCTCCGACCTGTAGCTGGCCTGGCCTGCTTTCCTCTCGGGATTTCTTGGGTGGCCTGGCCTTCCGAGT
CTTCCACTGCACACAGTACATCAGACATGGATCCAAGCCCATGTATACCCCGAACCTGACATCTGCCATGAGCTGTTGGGACAT
GTGCCCTGTTTCAGATCGCAGCTTTGCCCAGTTTGCCCAGTTTCCCAGGAAATTGGCCTTGCCTCTCGGGTGCACCTGATGAATACATTGA
AAAGCTCGCCACAATTTACTGGTTTACTGTGGAGTTTGGGCTCTGCAAACAAGGAGAGACTCCATAAAGGACATATGGTGCTGGGCT
CCTGTCATCCTTGGTGAATTACAGTACTGCTTATCAGAGAAGCCAAAGCTTCTCCCCTGGAGCTGGAGAAGACAGCCATCCAA
AATTACACTGTCACGGAGTTCCAGCCCCTCTCCAGTTCGCTACGACCCATACACCCAAAGGATTGAGGTCTTGGACAATACCCAGCAGCTTAAGA
GCCACAATACCTCGGCCTTCCATTAACAGTGAAATTGGAATCCTTGCAGTGCCCTGCCCTCCAGAAAATAAAGTAAAGCCATGACAGAATGTGG
TTTGGCTGATTCCATTAACAGTGAAATCCTTTACAAGATGTGTTGATGGAGATCCAACTATTCTTTCATCAGAAAAAGTCCGAAAAGCAAACCTTAATTGAAATA
ACAGCCTTAAATCCTTACAAGATGGAGAAACAACAACAAGAAATAAGTCAAAATAATCTGAAATGACAGGATATGAGTACATACTCA
AGAGCATAATGGTAAATCTTTGGGGGTCATCTTTGATTTAGAGATGATAATCCCATACTCTCAATTGAGTTAAATCAGTAATCT
GTCGCATTTCATCAAGATTA
```

Figure 6

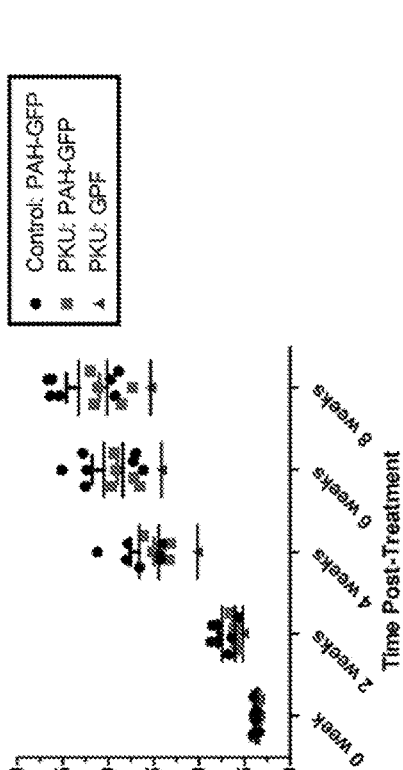
Figure 14B
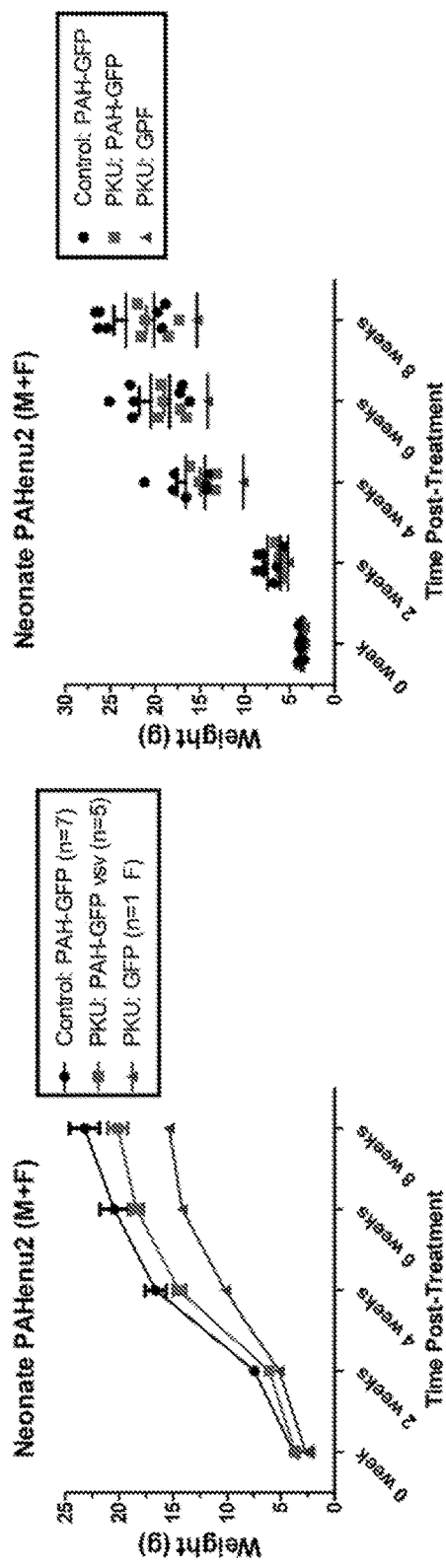
Figure 14A
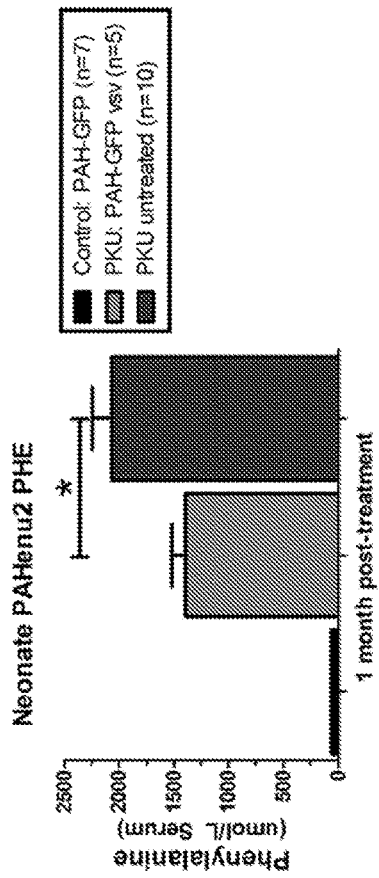
Figure 14D
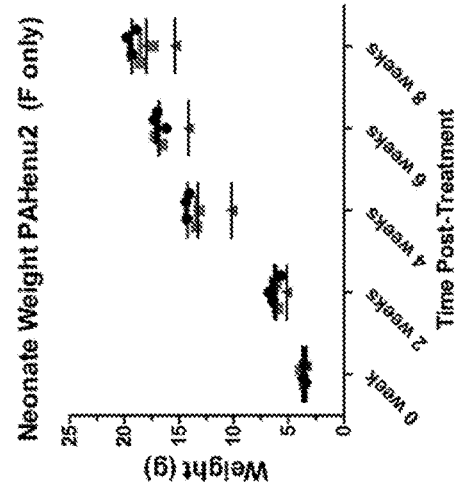
Figure 14C
Figure 14

SEQUENCE LISTING

<160> NUMBER OF SEQ ID NOS: 58

<210> SEQ ID NO 1
<211> LENGTH: 1359
<212> TYPE: DNA
<213> ORGANISM: Artificial Sequence
<220> FEATURE:
<223> OTHER INFORMATION: PAH

<400> SEQUENCE: 1

```
atgtccactg cggtcctgga aacccaggc ttgggcagga aactctctga ctttggacag      60
gaaacaagct atattgaaga caactgcaat caaaatggtg ccatatcact gatcttctca     120
ctcaaagaag aagttggtgc attggccaaa gtattcgcgt tatttgagga gaatgatgta     180
aacctgaccc acattgaatc tagaccttct cgtttaaaga agatgagta tgaatttttc     240 acccatttgg ataaacgtag cctgcctgct ctgacaaaca tcatcaagat cttgaggcat     300
gacattggtg ccactgtcca tgagctttca cgagataaga gaaagacac agtgccctgg     360 ttcccaagaa ccattcaaga gctggacaga tttgccaatc agattctcag ctatggagcg     420
gaactggatg ctgaccaccc tggttttaaa gatcctgtgt accgtgcaag acggaagcag     480
tttgctgaca ttgcctacaa ctaccgccat gggcagccca tccctcgagt ggaatacatg     540
gaggaagaaa agaaaacatg gggcacagtg ttcaagactc tgaagtcctt gtataaaacc     600
catgcttgct atgagtacaa tcacattttt ccacttcttg aaaagtactg tggcttccat     660
gaagataaca ttccccagct ggaagacgtt tctcaattcc tgcagacttg cactggtttc     720
cgcctccgac ctgtggctgg cctgctttcc tctcgggatt tcttgggtgg cctggccttc     780
cgagtcttcc actgcacaca gtacatcaga catggatcca agcccatgta taccccgaa      840 cctgacatct gccatgagct gttgggacat gtgcccttgt tttcagatcg cagctttgcc     900 cagtttccc aggaaattgg ccttgcctct ctgggtgcac tgatgaata cattgaaaag     960 ctcgccacaa tttactggtt tactgtggag tttgggctct gcaaacaagg agactccata    1020
aaggcatatg gtgctgggct cctgtcatcc tttggtgaat acagtactg cttatcagag    1080 aagccaaagc ttctccccct ggagctggag aagacagcca tccaaaatta cactgtcacg    1140
gagttccagc ccctgtatta cgtggcagag agttttaatg atgccaagga gaaagtaagg    1200
aactttgctg ccacaatacc tcggcccttc tcagttcgct acgacccata cacccaaagg    1260
```

```
attgaggtct tggacaatac ccagcagctt aagatttttgg ctgattccat taacagtgaa    1320
attggaatcc tttgcagtgc cctccagaaa ataaagtaa                           1359

<210> SEQ ID NO 2
<211> LENGTH: 1359
<212> TYPE: DNA
<213> ORGANISM: Artificial Sequence
<220> FEATURE:
<223> OTHER INFORMATION: Codon optimized PAH

<400> SEQUENCE: 2
atgagcacag ctgtgttgga aaatcctggg ctgggccgta agctttccga tttcggccag      60
gagacttcat acattgagga caactgcaac cagaatgggg ccatttcttt gatcttcagt    120
ctcaaagaag aggtaggcgc tctggctaag gtcctgaggc tgtttgagga aaatgacgtg    180
aatctgacac acattgagtc taggccttcc cgacttaaga aggatgagta tgagttcttc    240
acacacctgg acaaacgatc tctcccagca ctgaccaata tcatcaagat tctcaggcat    300
gatatcggtg ccacggtcca cgaactttca cgcgataaga agaaagacac agttccctgg    360
ttcccgagaa ccattcagga actggatagg tttgccaatc agattctgag ctatggggca    420
gagttggatg ccgaccatcc aggcttcaaa gaccccgtat atcgggctcg agaaaagcag    480
tttgcagaca tcgcttacaa ttacaggcat ggacagccca tccctagagt ggagtacatg    540
gaagaaggca agaaaacctg ggaacggtg tttaagaccc tcaaaagcct gtataagacc    600
cacgcgtgtt atgagtacaa ccacattttc ccattgctgg agaagtactg tggctttcac    660
gaggacaaca tccctcaact ggaggatgtt tcacagttcc ttcagacttg cactggtttc    720
cgccttcgac ctgtggctgg gctgcttagc tcacgggact tcctgggagg cctggccttc    780
agagtctttc actgcactca gtacattcgg catggctcta agccaatgta caccccctga    840
ccggatatat gccacgagct gttgggacat gtgcccctgt tttctgatcg cagcttttgcc    900 cagttttccc aggagattgg cctggcaagt cttggtgcgc ctgatgagta catcgagaag    960
ctcgcgacaa tctactggtt caccgtggaa tttggactct gcaaacaagg ggactctatc   1020
aaagcctacg gagcaggact cctctccagc ttcgtgaac tgcagtattg tctgtccgag   1080
aaacccaaac tcttgcccct ggaactggaa aagactgcca tccaaaacta tactgtcacg   1140
gaatttcagc cactgtatta tgtggctgaa tcctttaacg atgccaagga aaggtccgt    1200 aattttgctg ccacaatacc cgccccttc agcgtgagat acgacccgta tacacaacgg   1260
atagaggttc tggacaacac ccagcaactg aaaattctgg cagacagtat aaacagcgaa   1320
atagggatcc tctgtagtgc cctgcagaaa atcaaatga                           1359

<210> SEQ ID NO 3
<211> LENGTH: 897
<212> TYPE: DNA
<213> ORGANISM: Artificial Sequence
<220> FEATURE:
<223> OTHER INFORMATION: PAH 3'UTR sequence (897 nucleotides)

<400> SEQUENCE: 3
agccatggac agaatgtggt ctgtcagctg tgaatctgtt gatggagatc caactatttc      60
tttcatcaga aaagtccga aaagcaaacc ttaatttgaa ataacagcct taaatccttt    120
acaagatgga gaacaacaa ataagtcaaa ataatctgaa atgacaggat atgagtacat    180
actcaagagc ataatggtaa atcttttggg gtcatctttg atttagagat gataatccca    240
tactctcaat tgagttaaat cagtaatctg tcgcatttca tcaagattaa ttaaaatttg    300
```

```
ggacctgctt cattcaagct tcatatatgc tttgcagaga actcataaag gagcatataa    360
ggctaaatgt aaaacccaag actgtcatta gaattgaatt attgggctta atataaatcg    420
taacctatga agtttatttt ttattttagt taactatgat tccaattact actttgttat    480
tgtacctaag taaattttct ttaagtcaga agcccattaa aatagttaca agcattgaac    540
ttctttagta ttatattaat ataaaaacat ttttgtatgt tttattgtaa tcataaatac    600
tgctgtataa ggtaataaaa ctctgcacct aatccccata acttccagta tcattttcca    660
attaattatc aagtctgttt tgggaaacac tttgaggaca tttatgatgc agcagatgtt    720
gactaaaggc ttggttggta gatattcagg aaatgttcac tgaataaata agtaaataca    780
ttattgaaaa gcaaatctgt ataaatgtga aattttttatt tgtattagta ataaaacatt    840
agtagtttaa acaaaaaaaa aaaaaaaaaa aaaaaaaaa aaactcgact ctagatt       897
```

<210> SEQ ID NO 4
<211> LENGTH: 289
<212> TYPE: DNA
<213> ORGANISM: Artificial Sequence
<220> FEATURE:
<223> OTHER INFORMATION: PAH 3'UTR sequence (289 nucleotides)

<400> SEQUENCE: 4

```
agccatggac agaatgtggt ctgtcagctg tgaatctgtt gatggagatc caactatttc     60
tttcatcaga aaaagtccga aaagcaaacc ttaatttgaa ataacagcct taaatccttt    120
acaagatgga gaaacaacaa ataagtcaaa ataatctgaa atgacaggat atgagtacat    180
actcaagagc ataatggtaa atcttttggg gtcatctttg atttagagat gataatccca    240
tactctcaat tgagttaaat cagtaatctg tcgcatttca tcaagatta                289
```

<210> SEQ ID NO 5
<211> LENGTH: 53
<212> TYPE: DNA
<213> ORGANISM: Artificial Sequence
<220> FEATURE:
<223> OTHER INFORMATION: PAH shRNA sequence #1

<400> SEQUENCE: 5

```
tcgcatttca tcaagattaa tctcgagatt aatcttgatg aaatgcgatt ttt             53
```

<210> SEQ ID NO 6
<211> LENGTH: 53
<212> TYPE: DNA
<213> ORGANISM: Artificial Sequence
<220> FEATURE:
<223> OTHER INFORMATION: PAH shRNA sequence #2

<400> SEQUENCE: 6

```
actcataaag gagcatataa gctcgagctt atatgctcct ttatgagttt ttt             53
```

<210> SEQ ID NO 7
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 7

```
gtagtcttat gcaatactct tgtagtcttg caacatggta acgatgagtt agcaacatgc     60
cttacaagga gagaaaaagc accgtgcatg ccgattggtg gaagtaaggt ggtacgatcg    120
```

```
tgccttatta ggaaggcaac agacgggtct gacatggatt ggacgaacca ctgaattgcc      180
gcattgcaga gatattgtat ttaagtgcct agctcgatac aataaacg                  228

<210> SEQ ID NO 8
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 8
ggtctctctg gttagaccag atctgagcct gggagctctc tggctaacta gggaacccac      60
tgcttaagcc tcaataaagc ttgccttgag tgcttcaagt agtgtgtgcc cgtctgttgt     120
gtgactctgg taactagaga tccctcagac ccttttagtc agtgtggaaa atctctagca     180

<210> SEQ ID NO 9
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 9
tacgccaaaa attttgacta gcggaggcta aaggagaga g                           41

<210> SEQ ID NO 10
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 10
aggagctttg ttccttgggt tcttgggagc agcaggaagc actatgggcg cagcctcaat      60
gacgctgacg gtacaggcca gacaattatt gtctggtata gtgcagcagc agaacaattt     120
gctgagggct attgaggcgc aacagcatct gttgcaactc acagtctggg gcatcaagca     180
gctccaggca agaatcctgg ctgtggaaag atacctaaag gatcaacagc tcc            233

<210> SEQ ID NO 11
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 11
ttttaaaaga aaagggggga ttggggggta cagtgcaggg gaaagaatag tagacataat      60
agcaacagac atacaaacta agaattaca aaaacaaatt acaaaattca aaatttta       118

<210> SEQ ID NO 12
<211> LENGTH: 397
<212> TYPE: DNA
<213> ORGANISM: Artificial Sequence
<220> FEATURE:
<223> OTHER INFORMATION: Human alpha-1 antitrypsin promoter (hAAT)

<400> SEQUENCE: 12
gatcttgcta ccagtggaac agccactaag gattctgcag tgagagcaga gggccagcta      60
agtggtactc tcccagagac tgtctgactc acgccacccc ctccaccttg gacacaggac     120
gctgtggttt ctgagccagg tacaatgact cctttcggta agtgcagtgg aagctgtaca     180
```

```
ctgcccaggc aaagcgtccg ggcagcgtag gcgggcgact cagatcccag ccagtggact    240
tagcccctgt ttgctcctcc gataactggg gtgaccttgg ttaatattca ccagcagcct    300
cccccgttgc ccctctggat ccactgctta aatacggacg aggacagggc cctgtctcct    360
cagcttcagg caccaccact gacctgggac agtgaat                             397

<210> SEQ ID NO 13
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 13
aatcaacctc tgattacaaa atttgtgaaa gattgactgg tattcttaac tatgttgctc     60
cttttacgct atgtggatac gctgctttaa tgcctttgta tcatgctatt gcttcccgta    120
tggctttcat tttctcctcc ttgtataaat cctggttgct gtctctttat gaggagttgt    180
ggcccgttgt caggcaacgt ggcgtggtgt gcactgtgtt tgctgacgca acccccactg    240
gttggggcat tgccaccacc tgtcagctcc tttccgggac tttcgctttc cccctcccta    300
ttgccacggc ggaactcatc gccgcctgcc ttgcccgctg ctggacaggg gctcggctgt    360
tgggcactga caattccgtg gtgttgtcgg ggaaatcatc gtcctttcct ggctgctcg    420 cctgtgttgc cacctggatt ctgcgcggga cgtccttctg ctacgtccct tcggccctca    480
atccagcgga ccttccttcc gcggcctgc tgccggctct gcggcctctt ccgcgtcttc     540
gccttcgccc tcagacgagt cggatctccc tttgggccgc ctccccgcct    590

<210> SEQ ID NO 14
<211> LENGTH: 250
<212> TYPE: DNA
<213> ORGANISM: Artificial Sequence
<220> FEATURE:
<223> OTHER INFORMATION: 3' delta LTR

<400> SEQUENCE: 14
tggaagggct aattcactcc caacgaagat aagatctgct ttttgcttgt actgggtctc     60
tctggttaga ccagatctga gcctgggagc tctctggcta actagggaac ccactgctta    120
agcctcaata aagcttgcct tgagtgcttc aagtagtgtg tgcccgtctg ttgtgtgact    180
ctggtaacta gagatccctc agaccctttt agtcagtgtg aaaatctct agcagtagta    240 gttcatgtca                                                           250

<210> SEQ ID NO 15
<211> LENGTH: 217
<212> TYPE: DNA
<213> ORGANISM: Artificial Sequence
<220> FEATURE:
<223> OTHER INFORMATION: H1 Promoter

<400> SEQUENCE: 15
gaacgctgac gtcatcaacc cgctccaagg aatcgcgggc ccagtgtcac taggcgggaa     60
cacccagcgc gcgtgcgccc tggcaggaag atggctgtga gggacagggg agtggcgccc    120
tgcaatattt gcatgtcgct atgtgttctg ggaaatcacc ataaacgtga aatgtctttg    180
gatttgggaa tcttataagt tctgtatgag accactt                             217

<210> SEQ ID NO 16
```

<211> LENGTH: 642
<212> TYPE: DNA
<213> ORGANISM: Artificial Sequence
<220> FEATURE:
<223> OTHER INFORMATION: CAG promoter

<400> SEQUENCE: 16

| | | | | | | |
|---|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggac | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catgggtcga | ggtgagcccc | acgttctgct | tcactctccc | catctccccc | cctccccac | 420 |
| ccccaatttt | gtatttattt | attttttaat | tattttgtgc | agcgatgggg | gcggggggg | 480 |
| ggggggcgcg | cgccaggcgg | ggcggggcgg | ggcgagggggg | gggggcggggc | gaggcggaga | 540 |
| ggtgcggcgg | cagccaatca | gagcggcgcg | ctccgaaagt | ttcctttat | ggcgaggcgg | 600 |
| cggcggcggc | ggccctataa | aaagcgaagc | gcgcggcggg | cg | | 642 |

<210> SEQ ID NO 17
<211> LENGTH: 1503
<212> TYPE: DNA
<213> ORGANISM: Artificial Sequence
<220> FEATURE:
<223> OTHER INFORMATION: HIV Gag

<400> SEQUENCE: 17

| | | | | | | |
|---|---|---|---|---|---|---|
| atgggtgcga | gagcgtcagt | attaagcggg | ggagaattag | atcgatggga | aaaaattcgg | 60 |
| ttaaggccag | ggggaaagaa | aaaatataaa | ttaaaacata | tagtatgggc | aagcagggag | 120 |
| ctagaacgat | tcgcagttaa | tcctggcctg | ttagaaacat | cagaaggctg | tagacaaata | 180 |
| ctgggacagc | tacaaccatc | ccttcagaca | ggatcagaag | aacttagatc | attatataat | 240 |
| acagtagcaa | ccctctattg | tgtgcatcaa | aggatagaga | taaaagacac | caaggaagct | 300 |
| ttagacaaga | tagaggaaga | gcaaaacaaa | agtaagaaaa | aagcacagca | agcagcagct | 360 |
| gacacaggac | acagcaatca | ggtcagccaa | aattacccta | tagtgcagaa | catccagggg | 420 |
| caaatggtac | atcaggccat | atcacctaga | actttaaatg | catgggtaaa | agtagtagaa | 480 |
| gagaaggctt | tcagcccaga | agtgataccc | atgttttcag | cattatcaga | aggagccacc | 540 |
| ccacaagatt | taaacaccat | gctaaacaca | gtggggggac | atcaagcagc | catgcaaatg | 600 |
| ttaaaagaga | ccatcaatga | ggaagctgca | gaatgggata | gagtgcatcc | agtgcatgca | 660 |
| gggcctattg | caccaggcca | gatgagagaa | ccaagggggaa | gtgacatagc | aggaactact | 720 |
| agtacccttc | aggaacaaat | aggatggatg | acacataatc | cacctatccc | agtaggagaa | 780 |
| atctataaaa | gatggataat | cctgggatta | aataaaatag | taagaatgta | tagccctacc | 840 |
| agcattctgg | acataagaca | aggaccaaag | gaacccttta | gagactatgt | agaccgattc | 900 |
| tataaaactc | taagagccga | gcaagcttca | caagaggtaa | aaaattggat | gacagaaacc | 960 |
| ttgttggtcc | aaaatgcgaa | cccagattgt | aagactattt | taaaagcatt | gggaccagga | 1020 |
| gcgacactag | aagaaatgat | gacagcatgt | cagggagtgg | ggggacccgg | ccataaagca | 1080 |
| agagttttgg | ctgaagcaat | gagccaagta | acaaatccag | ctaccataat | gatacagaaa | 1140 |
| ggcaatttta | ggaaccaaag | aaagactgtt | aagtgtttca | attgtggcaa | agaagggcac | 1200 |

```
atagccaaaa attgcagggc ccctaggaaa aagggctgtt ggaaatgtgg aaaggaagga    1260
caccaaatga aagattgtac tgagagacag gctaattttt tagggaagat ctggccttcc    1320
cacaagggaa ggccagggaa ttttcttcag agcagaccag agccaacagc cccaccagaa    1380
gagagcttca ggtttgggga agagacaaca actccctctc agaagcagga gccgatagac    1440
aaggaactgt atcctttagc ttccctcaga tcactctttg gcagcgaccc ctcgtcacaa    1500
taa                                                                  1503

<210> SEQ ID NO 18
<211> LENGTH: 1872
<212> TYPE: DNA
<213> ORGANISM: Artificial Sequence
<220> FEATURE:
<223> OTHER INFORMATION: HIV Pol

<400> SEQUENCE: 18
atgaatttgc caggaagatg aaaccaaaa atgatagggg gaattggagg ttttatcaaa      60
gtaggacagt atgatcagat actcatagaa atctgcggac ataaagctat aggtacagta    120
ttagtaggac ctacacctgt caacataatt ggaagaaatc tgttgactca gattggctgc    180
actttaaatt ttcccattag tcctattgag actgtaccag taaaattaaa gccaggaatg    240
gatggcccaa aagttaaaca atggccattg acagaagaaa aaataaaagc attagtagaa    300
atttgtacag aaatggaaaa ggaaggaaaa atttcaaaaa ttgggcctga aaatccatac    360
aatactccag tatttgccat aaagaaaaaa gacagtacta atggagaaaa attagtagat    420
ttcagagaac ttaataagag aactcaagat ttctgggaag ttcaattagg aataccacat    480
cctgcagggt taaaacagaa aaaatcagta acagtactgg atgtgggcga tgcatatttt    540
tcagttccct tagataaaga cttcaggaag tatactgcat ttaccatacc tagtataaac    600
aatgagacac cagggattag atatcagtac aatgtgcttc cacagggatg aaaggatca    660 ccagcaatat tccagtgtag catgacaaaa atcttagagc cttttagaaa acaaaatcca    720
gacatagtca tctatcaata catggatgat ttgtatgtag gatctgactt agaaataggg    780
cagcatagaa caaaaataga ggaactgaga caacatctgt tgaggtgggg atttaccaca    840
ccagacaaaa aacatcagaa agaacctcca ttcctttgga tgggttatga actccatcct    900
gataaatgga cagtacagcc tatagtgctg ccagaaaagg acagctggac tgtcaatgac    960
atacagaaat tagtgggaaa attgaattgg gcaagtcaga tttatgcagg gattaaagta   1020
aggcaattat gtaaacttct tagggggaacc aaagcactaa cagaagtagt accactaaca   1080
gaagaagcag agctagaact ggcagaaaac agggagattc taaaagaacc ggtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
atgaagggtg cccacactaa tgatgtgaaa caattaacag aggcagtaca aaaaatagcc   1320
acagaaagca tagtaatatg gggaaagact cctaaattta aattacccat acaaaaggaa   1380
acatgggaag catggtggac agagtattgg caagccacct ggattcctga gtgggagttt   1440
gtcaataccc ctcccttagt gaagttatgg taccagttag agaaagaacc cataatagga   1500
gcagaaactt tctatgtaga tggggcagcc aatagggaaa ctaaattagg aaaagcagga   1560
tatgtaactg acagaggaag acaaaaagtt gtccccctaa cggacacaac aaatcagaag   1620
actgagttac aagcaattca tctagctttg caggattcgg gattagaagt aaacatagtg   1680
```

```
acagactcac aatatgcatt gggaatcatt caagcacaac cagataagag tgaatcagag   1740
ttagtcagtc aaataataga gcagttaata aaaaaggaaa aagtctacct ggcatgggta   1800
ccagcacaca aaggaattgg aggaaatgaa caagtagatg ggttggtcag tgctggaatc   1860
aggaaagtac ta                                                      1872

<210> SEQ ID NO 19
<211> LENGTH: 867
<212> TYPE: DNA
<213> ORGANISM: Artificial Sequence
<220> FEATURE:
<223> OTHER INFORMATION: HIV Int

<400> SEQUENCE: 19
tttttagatg gaatagataa ggcccaagaa gaacatgaga aatatcacag taattggaga     60
gcaatggcta gtgattttaa cctaccacct gtagtagcaa aagaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
agtggatata tagaagcaga agtaattcca gcagagacag ggcaagaaac agcatacttc    300
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaagaaaa    480
attataggac aggtaagaga tcaggctgaa catcttaaga cagcagtaca aatggcagta    540
ttcatccaca atttaaaag aaaaggggg attgggggt acagtgcagg ggaaagaata    540
```

```
agaagaagaa ggtggagaga gagacagaga cagatccatt cgattagtga acgatccttt    180
agcacttatc tgggacgatc tgcggagcct gtgcctcttc agctaccacc gcttgagaga    240
cttactcttg attgtaacga ggattgtgga acttctggga cgcagggggt gggaagccct    300
caaatattgg tggaatctcc tacaatattg gagtcaggag ctaaagaata g             351

<210> SEQ ID NO 22
<211> LENGTH: 577
<212> TYPE: DNA
<213> ORGANISM: Artificial Sequence
<220> FEATURE:
<223> OTHER INFORMATION: CMV Promoter

<400> SEQUENCE: 22
acattgatta ttgactagtt attaatagta atcaattacg gggtcattag ttcatagccc     60
atatatggag ttccgcgtta cataacttac ggtaaatggc ccgcctggct gaccgcccaa    120
cgacccccgc ccattgacgt caataatgac gtatgttccc atagtaacgc caatagggac    180
tttccattga cgtcaatggg tggagtattt acggtaaact gcccacttgg cagtacatca    240
agtgtatcat atgccaagta cgccccctat tgacgtcaat gacggtaaat ggcccgcctg    300
gcattatgcc cagtacatga ccttatggga ctttcctact tggcagtaca tctacgtatt    360
agtcatcgct attaccatgg tgatgcggtt ttggcagtac atcaatgggc gtggatagcg    420
gtttgactca cggggatttc caagtctcca ccccattgac gtcaatggga gtttgttttg    480
gcaccaaaat caacgggact ttccaaaatg tcgtaacaac tccgccccat tgacgcaaat    540
gggcggtagg cgtgtacggt gggaggtcta tataagc                             577

<210> SEQ ID NO 23
<211> LENGTH: 1531
<212> TYPE: DNA
<213> ORGANISM: Artificial Sequence
<220> FEATURE:
<223> OTHER INFORMATION: VSV-G / DNA fragment containing VSV-G /
      Envelope Glycoprotein

<400> SEQUENCE: 23
gaattcatga agtgcctttt gtacttagcc tttttattca ttggggtgaa ttgcaagttc     60
accatagttt ttccacacaa ccaaaaagga aactggaaaa atgttccttc taattaccat    120
tattgcccgt caagctcaga tttaaattgg cataatgact aataggcac agccttacaa     180 gtcaaaatgc ccaagagtca caaggctatt caagcagacg gttggatgtg tcatgcttcc    240
aaatgggtca ctacttgtga tttccgctgg tatggaccga agtatataac acattccatc    300
cgatccttca ctccatctgt agaacaatgc aaggaaagca ttgaacaaac gaaacaagga    360
acttggctga atccaggctt ccctcctcaa agttgtggat atgcaactgt gacggatgcc    420
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggagggc    660
acagggttca gaagtaacta ctttgcttat gaaactggag gcaaggcctg caaaatgcaa    720
tactgcaagc attggggagt cagactccca tcaggtgtct ggttcgagat ggctgataag    780
gatctctttg ctgcagccag attccctgaa tgcccagaag ggtcaagtat ctctgctcca    840
tctcagacct cagtggatgt aagtctaatt caggacgttg agaggatctt ggattattcc    900
```

```
ctctgccaag aaacctggag caaaatcaga gcgggtcttc caatctctcc agtggatctc    960
agctatcttg ctcctaaaaa cccaggaacc ggtcctgctt tcaccataat caatggtacc   1020
ctaaaatact ttgagaccag atacatcaga gtcgatattg ctgctccaat cctctcaaga   1080
atggtcggaa tgatcagtgg aactaccaca gaaagggaac tgtgggatga ctgggcacca   1140
tatgaagacg tggaaattgg acccaatgga gttctgagga ccagttcagg atataagttt   1200
cctttataca tgattggaca tggtatgttg gactccgatc ttcatcttag ctcaaaggct   1260
caggtgttcg aacatcctca cattcaagac gctgcttcgc aacttcctga tgatgagagt   1320
ttattttttg gtgatactgg gctatccaaa aatccaatcg agcttgtaga aggttggttc   1380
agtagttgga aaagctctat tgcctctttt tctttatca tagggttaat cattggacta   1440
ttcttggttc tccgagttgg tatccatctt tgcattaaat aaagcacac caagaaaaga   1500 cagatttata cagacataga gatgagaatt c                                 1531

<210> SEQ ID NO 24
<211> LENGTH: 352
<212> TYPE: DNA
<213> ORGANISM: Artificial Sequence
<220> FEATURE:
<223> OTHER INFORMATION: CAG enhancer

<400> SEQUENCE: 24
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggac tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tc           352

<210> SEQ ID NO 25
<211> LENGTH: 960
<212> TYPE: DNA
<213> ORGANISM: Artificial Sequence
<220> FEATURE:
<223> OTHER INFORMATION: Chicken beta actin intron

<400> SEQUENCE: 25
ggagtcgctg cgttgccttc gccccgtgcc ccgctccgcg ccgcctcgcg ccgcccgccc     60
cggctctgac tgaccgcgtt actcccacag gtgagcgggc gggacggccc ttctcctccg    120
ggctgtaatt agcgcttggt ttaatgacgg ctcgtttctt ttctgtggct gcgtgaaagc    180
cttaaagggc tccgggaggg ccctttgtgc gggggggagc ggctcggggg gtgcgtgcgt    240
gtgtgtgtgc gtggggagcg ccgcgtgcgg cccgcgctgc ccggcggctg tgagcgctgc    300
gggcgcggcg cggggctttg tgcgctccgc gtgtgcgcga gggagcgcgg ccggggggcg    360
gtgccccgcg gtgcgggggg gctgcgaggg gaacaaaggc tgcgtgcggg gtgtgtgcgt    420 ggggggggtga gcaggggtg tgggcgcggc ggtcgggctg taaccccccc ctgcaccccc    480
ctccccgagt tgctgagcac ggcccggctt cgggtgcggg gctccgtgcg gggcgtggcg    540
cggggctcgc cgtgccgggc gggggtggc ggcaggtggg ggtgccgggc ggggcggggc    600
cgcctcgggc cggggagggc tcggggggagg ggcgcggcgg ccccgagcg ccggcggctg    660 tcgaggcgcg gcgagccgca gccattgcct tttatggtaa tcgtgcgaga gggcgcaggg    720
```

| | |
|---|---|
| acttcctttg tcccaaatct ggcggagccg aaatctggga ggcgccgccg cacccctct | 780 |
| agcgggcgcg ggcgaagcgg tgcggcgccg gcaggaagga aatgggcggg gagggccttc | 840 |
| gtgcgtcgcc gcgccgccgt ccccttctcc atctccagcc tcgggctgc cgcagggga | 900 |
| cggctgcctt cgggggggac ggggcagggc ggggttcggc ttctggcgtg tgaccggcgg | 960 |

<210> SEQ ID NO 26
<211> LENGTH: 448
<212> TYPE: DNA
<213> ORGANISM: Artificial Sequence
<220> FEATURE:
<223> OTHER INFORMATION: Rabbit beta globin poly A

<400> SEQUENCE: 26

| | |
|---|---|
| agatctttt ccctctgcca aaaattatgg ggacatcatg aagccccttg agcatctgac | 60 |
| ttctggctaa taaaggaaat ttattttcat tgcaatagtg tgttggaatt ttttgtgtct | 120 |
| ctcactcgga aggacatatg ggagggcaaa tcatttaaaa catcagaatg agtatttggt | 180 |
| ttagagtttg gcaacatatg ccatatgctg gctgccatga acaaaggtgg ctataaagag | 240 |
| gtcatcagta tatgaaacag ccccctgctg tccattcctt attccataga aaagccttga | 300 |
| cttgaggtta gattttttt atattttgtt ttgtgttatt tttttcttta acatccctaa | 360 |
| aattttcctt acatgtttta ctagccagat ttttcctcct ctcctgacta ctcccagtca | 420 |
| tagctgtccc tcttctctta tgaagatc | 448 |

<210> SEQ ID NO 27
<211> LENGTH: 573
<212> TYPE: DNA
<213> ORGANISM: Artificial Sequence
<220> FEATURE:
<223> OTHER INFORMATION: Beta globin intron

<400> SEQUENCE: 27

| | |
|---|---|
| gtgagtttgg ggacccttga ttgttctttc ttttcgcta ttgtaaaatt catgttatat | 60 |
| ggaggggca agttttcag ggtgttgttt agaatgggaa gatgtcccct gtatcaccat | 120 |
| ggaccctcat gataatttg tttctttcac tttctactct gttgacaacc attgtctcct | 180 |
| cttattttct tttcattttc tgtaacttttt tcgttaaact ttagcttgca tttgtaacga | 240 |
| atttttaaat tcacttttgt ttatttgtca gattgtaagt actttctcta atcacttttt | 300 |
| tttcaaggca atcagggtat attatattgt acttcagcac agttttagag aacaattgtt | 360 |
| ataattaaat gataaggtag aatatttctg catataaatt ctggctggcg tggaaatatt | 420 |
| cttattggta gaaacaacta cacccctggtc atcatcctgc ctttctcttt atggttacaa | 480 |
| tgatatacac tgtttgagat gaggataaaa tactctgagt ccaaaccggg cccctctgct | 540 |
| aaccatgttc atgccttctt ctctttccta cag | 573 |

<210> SEQ ID NO 28
<211> LENGTH: 31
<212> TYPE: DNA
<213> ORGANISM: Artificial Sequence
<220> FEATURE:
<223> OTHER INFORMATION: Primer

<400> SEQUENCE: 28

| | |
|---|---|
| taagcagaat tcatgaattt gccaggaaga t | 31 |

<210> SEQ ID NO 29
<211> LENGTH: 36

```
<212> TYPE: DNA
<213> ORGANISM: Artificial Sequence
<220> FEATURE:
<223> OTHER INFORMATION: Primer

<400> SEQUENCE: 29
ccatacaatg aatggacact aggcggccgc acgaat                                   36

<210> SEQ ID NO 30
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 30
gaattcatga atttgccagg aagatggaaa ccaaaaatga tagggggaat tggaggtttt         60
atcaaagtaa gacagtatga tcagatactc atagaaatct gcggacataa agctataggt        120
acagtattag taggacctac acctgtcaac ataattggaa gaaatctgtt gactcagatt        180
ggctgcactt taaattttcc cattagtcct attgagactg taccagtaaa attaaagcca        240
ggaatggatg gcccaaaagt taaacaatgg ccattgacag aagaaaaaat aaaagcatta        300
gtagaaattt gtacagaaat ggaaaaggaa ggaaaaattt caaaaattgg gcctgaaaat        360
ccatacaata ctccagtatt tgccataaag aaaaaagaca gtactaaatg gagaaaatta        420
gtagatttca gagaacttaa taagagaact caagatttct gggaagttca attaggaata        480
ccacatcctg cagggttaaa acagaaaaaa tcagtaacag tactggatgt gggcgatgca        540
tatttttcag ttcccttaga taaagacttc aggaagtata ctgcatttac catacctagt        600
ataaacaatg agacaccagg gattagatat cagtacaatg tgcttccaca gggatggaaa        660
ggatcaccag caatattcca gtgtagcatg acaaaaatct tagagccttt tagaaaacaa        720
aatccagaca tagtcatcta tcaatacatg gatgatttgt atgtaggatc tgacttagaa        780
atagggcagc atagaacaaa aatagaggaa ctgagacaac atctgttgag gtggggattt        840
accacaccag acaaaaaaca tcagaaagaa cctccattcc tttggatggg ttatgaactc        900
catcctgata atggacagt acagcctata gtgctgccag aaaaggacag ctggactgtc         960
aatgacatac agaaattagt gggaaaattg aattgggcaa gtcagattta tgcagggatt       1020
aaagtaaggc aattatgtaa acttcttagg ggaaccaaag cactaacaga agtagtacca       1080
ctaacagaag aagcagagct agaactggca gaaaacaggg agattctaaa agaaccggta       1140
catggagtgt attatgaccc atcaaaagac ttaatagcag aaatacagaa gcaggggcaa       1200
ggccaatgga catatcaaat ttatcaagag ccatttaaaa atctgaaaac aggaaagtat       1260
gcaagaatga agggtgccca cactaatgat gtgaaacaat taacagaggc agtacaaaaa       1320
atagccacag aaagcatagt aatatgggga aagactccta aatttaaatt acccatacaa       1380
aaggaaacat gggaagcatg gtggacagag tattggcaag ccacctggat tcctgagtgg       1440
gagtttgtca atacccctcc cttagtgaag ttatggtacc agttagagaa agaacccata       1500
ataggagcag aaactttcta tgtagatggg gcagccaata gggaaactaa attaggaaaa       1560
gcaggatatg taactgacag aggaagacaa aaagttgtcc ccctaacgga cacaacaaat       1620
cagaagactg agttacaagc aattcatcta gctttgcagg attcgggatt agaagtaaac       1680
atagtgacag actcacaata tgcattggga atcattcaag cacaaccaga taagagtgaa       1740
tcagagttag tcagtcaaat aatagagcag ttaataaaaa aggaaaaagt ctacctggca       1800
```

-continued

| | |
|---|---|
| tgggtaccag cacacaaagg aattggagga aatgaacaag tagataaatt ggtcagtgct | 1860 |
| ggaatcagga agtactatt tttagatgga atagataagg cccaagaaga acatgagaaa | 1920 |
| tatcacagta attggagagc aatggctagt gattttaacc taccacctgt agtagcaaaa | 1980 |
| gaaatagtag ccagctgtga taaatgtcag ctaaaagggg aagccatgca tggacaagta | 2040 |
| gactgtagcc caggaatatg gcagctagat tgtacacatt tagaaggaaa agttatcttg | 2100 |
| gtagcagttc atgtagccag tggatatata gaagcagaag taattccagc agagacaggg | 2160 |
| caagaaacag catacttcct cttaaaatta gcaggaagat ggccagtaaa aacagtacat | 2220 |
| acagacaatg gcagcaattt caccagtact acagttaagg ccgcctgttg gtgggcgggg | 2280 |
| atcaagcagg aatttggcat tccctacaat ccccaaagtc aaggagtaat agaatctatg | 2340 |
| aataaagaat taagaaaat tataggacag gtaagagatc aggctgaaca tcttaagaca | 2400 |
| gcagtacaaa tggcagtatt catccacaat tttaaaagaa aaggggggat tggggggtac | 2460 |
| agtgcagggg aaagaatagt agacataata gcaacagaca tacaaactaa agaattacaa | 2520 |
| aaacaaatta caaaaattca aaattttcgg gtttattaca gggacagcag agatccagtt | 2580 |
| tggaaaggac cagcaaagct cctctggaaa ggtgaagggg cagtagtaat acaagataat | 2640 |
| agtgacataa aagtagtgcc aagaagaaaa gcaaagatca tcagggatta tggaaaacag | 2700 |
| atggcaggtg atgattgtgt ggcaagtaga caggatgagg attaa | 2745 |

<210> SEQ ID NO 31
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 31

| | |
|---|---|
| tctagaatgg caggaagaag cggagacagc gacgaagagc tcatcagaac agtcagactc | 60 |
| atcaagcttc tctatcaaag caacccacct cccaatcccg aggggacccg acaggcccga | 120 |
| aggaatagaa gaagaaggtg gagagagaga cagagacaga tccattcgat tagtgaacgg | 180 |
| atccttggca cttatctggg acgatctgcg gagcctgtgc ctcttcagct accaccgctt | 240 |
| gagagactta ctcttgattg taacgaggat tgtggaactt ctgggacgca ggggtggga | 300 |
| agcccctcaaa tattggtgga atctcctaca atattggagt caggagctaa agaatagagg | 360 |
| agctttgttc cttgggttct tgggagcagc aggaagcact atgggcgcag cgtcaatgac | 420 |
| gctgacggta caggccagac aattattgtc tggtatagtg cagcagcaga acaatttgct | 480 |
| gagggctatt gaggcgcaac agcatctgtt gcaactcaca gtctggggca tcaagcagct | 540 |
| ccaggcaaga atcctggctg tggaaagata cctaaaggat caacagctcc tagatctttt | 600 |
| tccctctgcc aaaaattatg gggacatcat gaagccccct gagcatctga cttctggcta | 660 |
| ataaggaaa tttattttca ttgcaatagt gtgttggaat ttttgtgtc tctcactcgg | 720 |
| aaggacatat gggagggcaa tcatttaaaa acatcagaat gagtatttgg tttagagttt | 780 |
| ggcaacatat gccatatgct ggctgccatg aacaaaggtg gctataaaga ggtcatcagt | 840 |
| atatgaaaca gccccctgct gtccattcct tattccatag aaaagccttg acttgaggtt | 900 |
| agatttttt tatattttgt tttgtgttat ttttttcttt aacatcccta aaattttcct | 960 |
| tacatgtttt actagccaga ttttttcctcc tctcctgact actcccagtc atagctgtcc | 1020 |
| ctcttctctt atgaagatcc ctcgacctgc agcccaagct tggcgtaatc atggtcatag | 1080 |

| | |
|---|---|
| ctgtttcctg tgtgaaattg ttatccgctc acaattccac acaacatacg agccggaagc | 1140 |
| ataaagtgta aagcctgggg tgcctaatga gtgagctaac tcacattaat tgcgttgcgc | 1200 |
| tcactgcccg ctttccagtc gggaaacctg tcgtgccagc ggatccgcat ctcaattagt | 1260 |
| cagcaaccat agtcccgccc ctaactccgc ccatcccgcc cctaactccg cccagttccg | 1320 |
| cccattctcc gccccatggc tgactaattt tttttattta tgcagaggcc gaggccgcct | 1380 |
| cggcctctga gctattccag aagtagtgag gaggcttttt tggaggccta ggcttttgca | 1440 |
| aaaagctaac ttgtttattg cagcttataa tggttacaaa taaagcaata gcatcacaaa | 1500 |
| tttcacaaat aaagcatttt tttcactgca ttctagttgt ggtttgtcca aactcatcaa | 1560 |
| tgtatcttat cagcggccgc cccggg | 1586 |

<210> SEQ ID NO 32
<211> LENGTH: 1614
<212> TYPE: DNA
<213> ORGANISM: Artificial Sequence
<220> FEATURE:
<223> OTHER INFORMATION: DNA fragment containing the CAG
      enhancer/promoter/intron sequence

<400> SEQUENCE: 32

| | |
|---|---|
| acgcgttagt tattaatagt aatcaattac ggggtcatta gttcatagcc catatatgga | 60 |
| gttccgcgtt acataactta cggtaaatgg cccgcctggc tgaccgccca acgacccccg | 120 |
| cccattgacg tcaataatga cgtatgttcc catagtaacg ccaataggga ctttccattg | 180 |
| acgtcaatgg gtggactatt tacggtaaac tgcccacttg gcagtacatc aagtgtatca | 240 |
| tatgccaagt acgcccccta ttgacgtcaa tgacggtaaa tggcccgcct ggcattatgc | 300 |
| ccagtacatg accttatggg actttcctac ttggcagtac atctacgtat tagtcatcgc | 360 |
| tattaccatg gtcgaggtg agccccacgt tctgcttcac tctccccatc tcccccccct | 420 |
| ccccaccccc aattttgtat ttatttattt tttaattatt ttgtgcagcg atggggcgg | 480 |
| ggggggggg ggcgcgcgcc aggcggggcg gggcggggcg aggggcgggg cggggcgagg | 540 |
| cggagaggtg cggcggcagc caatcagagc ggcgcgctcc gaaagtttcc ttttatggcg | 600 |
| aggcggcggc ggcggcggcc ctataaaaag cgaagcgcgc ggcgggcggg agtcgctgcg | 660 |
| ttgccttcgc cccgtgcccc gctccgcgcc gcctcgcgcc gcccgccccg gctctgactg | 720 |
| accgcgttac tcccacaggt gagcgggcgg gacggccctt ctcctccggg ctgtaattag | 780 |
| cgcttggttt aatgacggct cgtttctttt ctgtggctgc gtgaaagcct taaagggctc | 840 |
| cgggagggcc ctttgtgcgg gggggagcgg ctcgggggt gcgtgcgtgt gtgtgtgcgt | 900 |
| ggggagcgcc gcgtgcggcc cgcgctgccc ggcggctgtg agcgctgcgg cgcggcgcg | 960 |
| gggctttgtg cgctccgcgt gtgcgcgagg ggagcgcggc cggggcggt gccccgcggt | 1020 |
| gcggggggc tgcgagggga acaaaggctg cgtgcgggt gtgtgcgtgg ggggtgagc | 1080 |
| agggggtgtg ggcgcggcgg tcgggctgta acccccccct gcacccccct ccccgagttg | 1140 |
| ctgagcacgg cccggcttcg ggtgcggggc tccgtgcggg gcgtggcgcg ggctcgccg | 1200 |
| tgccgggcgg ggggtggcgg caggtggggg tgccgggcgg ggcggggccg cctcgggccg | 1260 |
| gggagggctc ggggggagggg gcgcggcggcc ccggagcgcc ggcggctgtc gaggcgcggc | 1320 |
| gagccgcagc cattgccttt tatggtaatc gtgcgagagg gcgcagggac ttcctttgtc | 1380 |
| ccaaatctgg cggagccgaa atctgggagg cgccgccgca ccccctctag cgggcgcggg | 1440 |
| cgaagcggt cggcgccggc aggaaggaaa tgggcgggga gggccttcgt gcgtcgccgc | 1500 |

```
gccgccgtcc ccttctccat ctccagcctc ggggctgccg caggggggacg gctgccttcg    1560 gggggggacgg ggcagggcgg ggttcggctt ctggcgtgtg accggcggga attc          1614
```

<210> SEQ ID NO 33
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 33

```
caattgcgat gtacgggcca gatatacgcg tatctgaggg gactagggtg tgtttaggcg      60
aaaagcgggg cttcggttgt acgcggttag gagtcccctc aggatatagt agtttcgctt     120
ttgcataggg aggggggaaat gtagtcttat gcaatacact tgtagtcttg caacatggta     180
acgatgagtt agcaacatgc cttacaagga gagaaaaagc accgtgcatg ccgattggtg     240
gaagtaaggt ggtacgatcg tgccttatta ggaaggcaac agacaggtct gacatggatt     300
ggacgaacca ctgaattccg cattgcagag ataattgtat ttaagtgcct agctcgatac     360
aataaacgcc atttgaccat tcaccacatt ggtgtgcacc tccaagctcg agctcgttta     420
gtgaaccgtc agatcgcctg gagacgccat ccacgctgtt ttgacctcca tagaagacac     480
cgggaccgat ccagcctccc ctcgaagcta gcgattaggc atctcctatg gcaggaagaa     540
gcggagacag cgacgaagaa ctcctcaagg cagtcagact catcaagttt ctctatcaaa     600
gcaacccacc tcccaatccc gaggggaccc gacaggcccg aaggaataga agaagaaggt     660
ggagagagag acagagacag atccattcga ttagtgaacg gatccttagc acttatctgg     720
gacgatctgc ggagcctgtg cctcttcagc taccaccgct tgagagactt actcttgatt     780
gtaacgagga ttgtggaact tctgggacgc aggggtggg aagccctcaa atattggtgg     840
aatctcctac aatattggag tcaggagcta agaatagtc taga                       884
```

<210> SEQ ID NO 34
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 34

```
ccggtgccta gagaaggtgg cgcggggtaa actgggaaag tgatgtcgtg tactggctcc      60 gccttttttcc cgagggtggg ggagaaccgt atataagtgc agtagtcgcc gtgaacgttc    120
tttttcgcaa cgggtttgcc gccagaacac aggtaagtgc cgtgtgtggt tcccgcgggc    180
ctggcctctt tacgggttat ggcccttgcg tgccttgaat tacttccacg cccctggctg    240
cagtacgtga ttcttgatcc cgagcttcgg gttggaagtg ggtgggagag ttcgaggcct    300
tgcgcttaag gagccccttc gcctcgtgct tgagttgagg cctggcctgg gcgctggggc    360
cgccgcgtgc gaatctggtg gcaccttcgc gcctgtctcg ctgctttcga taagtctcta    420
gccatttaaa attttttgatg acctgctgcg acgcttttttt tctggcaaga tagtcttgta    480
aatgcgggcc aagatctgca cactggtatt tcggttttttg gggccgcggg cggcgacggg    540
gcccgtgcgt cccagcgcac atgttcggcg aggcggggcc tgcgagcgcg ccaccgaga    600 atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg gcgctcggga    780
```

```
gagcgggcgg gtgagtcacc cacacaaagg aaaagggcct ttccgtcctc agccgtcgct     840
tcatgtgact ccacggagta ccgggcgccg tccaggcacc tcgattagtt ctcgagcttt     900
tggagtacgt cgtctttagg ttgggggggag gggttttatg cgatggagtt tccccacact    960
gagtgggtgg agactgaagt taggccagct tggcacttga tgtaattctc cttggaattt    1020 gcccttttg agtttggatc ttggttcatt ctcaagcctc agacagtggt tcaaagtttt    1080
tttcttccat ttcaggtgtc gtga                                          1104
```

<210> SEQ ID NO 35
<211> LENGTH: 511
<212> TYPE: DNA
<213> ORGANISM: Artificial Sequence
<220> FEATURE:
<223> OTHER INFORMATION: Promoter-PGK

<400> SEQUENCE: 35

```
ggggttgggg ttgcgccttt tccaaggcag ccctgggttt gcgcagggac gcggctgctc      60
tgggcgtggt tccgggaaac gcagcggcgc cgaccctggg tctcgcacat tcttcacgtc     120
cgttcgcagc gtcacccgga tcttcgccgc tacccttgtg ggcccccggg cgacgcttcc     180
tgctccgccc ctaagtcggg aaggttcctt gcggttcgcg gcgtgccgga cgtgacaaac     240
ggaagccgca cgtctcacta gtaccctcgc agacggacag cgccagggag caatggcagc     300
gcgccgaccg cgatgggctg tggccaatag cggctgctca gcagggcgcg ccgagagcag     360
cggccgggaa ggggcggtgc gggaggcggg gtgtggggcg gtagtgtggg ccctgttcct     420
gcccgcgcgg tgttccgcat tctgcaagcc tccggagcgc acgtcggcag tcggctccct     480
cgttgaccga atcaccgacc tctctcccca g                                   511
```

<210> SEQ ID NO 36
<211> LENGTH: 1162
<212> TYPE: DNA
<213> ORGANISM: Artificial Sequence
<220> FEATURE:
<223> OTHER INFORMATION: Promoter-UbC

<400> SEQUENCE: 36

```
gcgccgggtt ttggcgcctc ccgcgggcgc cccctcctc acggcgagcg ctgccacgtc       60
agacgaaggg cgcaggagcg ttcctgatcc ttccgcccgg acgctcagga cagcggcccg     120
ctgctcataa gactcggcct tagaacccca gtatcagcag aaggacattt taggacggga     180
cttgggtgac tctagggcac tggttttctt tccagagagc ggaacaggcg aggaaaagta     240
gtcccttctc ggcgattctg cggagggatc tccgtggggc ggtgaacgcc gatgattata     300
taaggacgcg ccgggtgtgg cacagctagt tccgtcgcag ccgggatttg gtcgcggtt     360 cttgtttgtg gatcgctgtg atcgtcactt ggtgagttgc gggctgctgg gctggccggg     420
gctttcgtgg ccgccgggcc gctcggtggg acgaagcgt gtggagagac cgccaagggc     480
tgtagtctgg gtccgcgagc aaggttgccc tgaactgggg gttgggggga gcgcacaaaa     540
tggcggctgt tcccgagtct tgaatggaag acgcttgtaa ggcgggctgt gaggtcgttg     600
aaacaaggtg gggggcatgg tgggcggcaa gaacccaagg tcttgaggcc ttcgctaatg     660
cgggaaagct cttattcggg tgagatgggc tggggcacca tctgggacc ctgacgtgaa     720 gtttgtcact gactggagaa ctcgggtttg tcgtctggtt gcggggcgg cagttatgcg     780 gtgccgttgg gcagtgcacc cgtacctttg ggagcgcgcg cctcgtcgtg tcgtgacgtc     840
```

```
acccgttctg ttggcttata atgcagggtg gggccacctg ccggtaggtg tgcggtaggc    900
ttttctccgt cgcaggacgc agggttcggg cctagggtag gctctcctga atcgacaggc    960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcacctt tgaaatgtaa tcatttgggt caatatgtaa    1140
ttttcagtgt tagactagta aa                                           1162

<210> SEQ ID NO 37
<211> LENGTH: 120
<212> TYPE: DNA
<213> ORGANISM: Artificial Sequence
<220> FEATURE:
<223> OTHER INFORMATION: Poly A-SV40

<400> SEQUENCE: 37
gtttattgca gcttataatg gttacaaata agcaatagc atcacaaatt tcacaaataa    60 agcattttt tcactgcatt ctagttgtgg tttgtccaaa ctcatcaatg tatcttatca   120

<210> SEQ ID NO 38
<211> LENGTH: 227
<212> TYPE: DNA
<213> ORGANISM: Artificial Sequence
<220> FEATURE:
<223> OTHER INFORMATION: Poly A-bGH

<400> SEQUENCE: 38
gactgtgcct tctagttgcc agccatctgt tgtttgcccc tccccgtgc cttccttgac     60 cctggaaggt gccactccca ctgtcctttc ctaataaaat gaggaaattg catcgcattg   120
tctgagtagg tgtcattcta ttctgggggg tggggtgggg caggacagca agggggagga   180
ttgggaagac aatagcaggc atgctgggga tgcggtgggc tctatgg                 227

<210> SEQ ID NO 39
<211> LENGTH: 1695
<212> TYPE: DNA
<213> ORGANISM: Artificial Sequence
<220> FEATURE:
<223> OTHER INFORMATION: Envelope-RD114

<400> SEQUENCE: 39
atgaaactcc caacaggaat ggtcatttta tgtagcctaa taatagttcg gcagggttt     60 gacgaccccc gcaaggctat cgcattagta caaaaacaac atggtaaacc atgcgaatgc   120
agcggagggc aggtatccga ggccccaccg aactccatcc aacaggtaac ttgcccaggc   180
aagacggcct acttaatgac caaccaaaaa tggaaatgca gagtcactcc aaaaaatctc   240 accccctagcg ggggagaact ccagaactgc ccctgtaaca ctttccagga ctcgatgcac   300
agttcttgtt atactgaata ccggcaatgc agggcgaata taagacata ctacacggcc   360 accttgctta aaatacggtc tgggagcctc aacgaggtac agatattaca aaaccccaat   420
cagctcctac agtccccttg taggggctct ataaatcagc ccgtttgctg gagtgccaca   480
gcccccatcc atatctccga tggtggaggg ccctcgata ctaagagagt gtggacagtc   540
caaaaaaggc tagaacaaat tcataaggct atgcatcctg aacttcaata ccacccctta   600
gccctgccca agtcagaga tgaccttagc cttgatgcac ggactttga tatccctgaat   660 accacttta ggttactcca gatgtccaat tttagccttg cccaagattg ttggctctgt   720
ttaaaactag gtaccccta ccctcttgcg atacccact cctctttaac ctactcccta   780
```

```
gcagactccc tagcgaatgc ctcctgtcag attatacctc ccctcttggt tcaaccgatg    840
cagttctcca actcgtcctg tttatcttcc cctttcatta acgatacgga acaaatagac    900
ttaggtgcag tcacctttac taactgcacc tctgtagcca atgtcagtag tcctttatgt    960
gccctaaacg ggtcagtctt cctctgtgga ataacatgg catacaccta tttaccccaa    1020
aactggacag gactttgcgt ccaagcctcc ctcctccccg acattgacat catcccgggg   1080
gatgagccag tccccattcc tgccattgat cattatatac atagacctaa acgagctgta   1140
cagttcatcc ctttactagc tggactggga atcaccgcag cattcaccac cggagctaca   1200
ggcctaggtg tctccgtcac ccagtataca aaattatccc atcagttaat atctgatgtc   1260
caagtcttat ccggtaccat acaagattta caagaccagg tagactcgtt agctgaagta   1320
gttctccaaa ataggagggg actggaccta ctaacggcag aacaaggagg aatttgttta   1380
gccttacaag aaaaatgctg tttttatgct aacaagtcag gaattgtgag aaacaaaata   1440
agaaccctac aagaagaatt acaaaaacgc agggaaagcc tggcatccaa ccctctctgg   1500
accgggctgc agggctttct tccgtacctc ctacctctcc tgggacccct actcaccctc   1560
ctactcatac taaccattgg gccatgcgtt ttcaatcgat tggtccaatt tgttaaagac   1620
aggatctcag tggtccaggc tctggttttg actcagcaat atcaccagct aaaacccata   1680
gagtacgagc catga                                                   1695

<210> SEQ ID NO 40
<211> LENGTH: 2013
<212> TYPE: DNA
<213> ORGANISM: Artificial Sequence
<220> FEATURE:
<223> OTHER INFORMATION: Envelope-GALV

<400> SEQUENCE: 40
atgcttctca cctcaagccc gcaccacctt cggcaccaga tgagtcctgg gagctggaaa    60
agactgatca tcctcttaag ctgcgtattc ggagacggca aaacgagtct gcagaataag   120
aacccccacc agcctgtgac cctcacctgg caggtactgt cccaaactgg ggacgttgtc   180
tgggacaaaa aggcagtcca gccccttttgg acttggtggc cctctcttac acctgatgta   240
tgtgccctgg cggccggtct tgagtcctgg gatatcccgg gatccgatgt atcgtcctct   300
aaaagagtta gacctcctga ttcagactat actgccgctt ataagcaaat cacctgggga   360
gccatagggt gcagctaccc tcgggctagg accaggatgg caaattcccc cttctacgtg   420
tgtccccgag ctggccgaac ccattcagaa gctaggaggt gtggggggct agaatcccta   480
tactgtaaag aatggagttg tgagaccacg ggtaccgttt attggcaacc caagtcctca   540
tgggacctca taactgtaaa atgggaccaa aatgtgaaat gggagcaaaa atttcaaaag   600
tgtgaacaaa ccggctggtg taaccccctc aagatagact tcacagaaaa aggaaaactc   660
tccagagatt ggataacgga aaaacctggt gaattaaggt tctatgtata tggacaccca   720
ggcatacagt tgactatccg cttagaggtc actaacatgc cggttgtggc agtgggccca   780
gaccctgtcc ttgcggaaca gggacctcct agcaagcccc tcactctccc tctctcccca   840
cggaaagcgc cgcccacccc tctaccccg gcggctagtg agcaaacccc tgcggtgcat   900
ggagaaactg ttaccctaaa ctctccgcct cccaccagtg gcgaccgact ctttggcctt   960
gtgcaggggg cctcctaac cttgaatgct accaacccag gggccactaa gtcttgctgg   1020
ctctgtttgg gcatgagccc ccccttattat gaagggatag cctcttcagg agaggtcgct   1080
```

| | | | | |
|---|---|---|---|---|
| tatacctcca | accatacccg | atgccactgg | ggggcccaag | gaaagcttac | cctcactgag | 1140 |
| gtctccggac | tcgggtcatg | catagggaag | gtgcctctta | cccatcaaca | tctttgcaac | 1200 |
| cagaccttac | ccatcaattc | ctctaaaaac | catcagtatc | tgctcccctc | aaaccatagc | 1260 |
| tggtgggcct | gcagcactgg | cctcaccccc | tgcctctcca | cctcagtttt | taatcagtct | 1320 |
| aaagacttct | gtgtccaggt | ccagctgatc | ccccgcatct | attaccattc | tgaagaaacc | 1380 |
| ttgttacaag | cctatgacaa | atcacccccc | aggtttaaaa | gagagcctgc | ctcacttacc | 1440 |
| ctagctgtct | tcctggggtt | agggattgcg | gcaggtatag | gtactggctc | aaccgcccta | 1500 |
| attaaagggc | ccatagacct | ccagcaaggc | ctaaccagcc | tccaaatcgc | cattgacgct | 1560 |
| gacctccggg | cccttcagga | ctcaatcagc | aagctagagg | actcactgac | ttccctatct | 1620 |
| gaggtagtac | tccaaaatag | gagaggcctt | gacttactat | tccttaaaga | aggaggcctc | 1680 |
| tgcgcggccc | taaaagaaga | gtgctgtttt | tatgtagacc | actcaggtgc | agtacgagac | 1740 |
| tccatgaaaa | aacttaaaga | aagactagat | aaaagacagt | tagagcgcca | gaaaaaccaa | 1800 |
| aactggtatg | aagggtggtt | caataactcc | ccttggttta | ctaccctact | atcaaccatc | 1860 |
| gctgggcccc | tattgctcct | cctttttgtta | ctcactcttg | ggccctgcat | catcaataaa | 1920 |
| ttaatccaat | tcatcaatga | taggataagt | gcagtcaaaa | ttttagtcct | tagacagaaa | 1980 |
| tatcagaccc | tagataacga | ggaaaaacctt | taa | | | 2013 |

<210> SEQ ID NO 41
<211> LENGTH: 1530
<212> TYPE: DNA
<213> ORGANISM: Artificial Sequence
<220> FEATURE:
<223> OTHER INFORMATION: Envelope-FUG

<400> SEQUENCE: 41

| | | | | | | |
|---|---|---|---|---|---|---|
| atggttccgc | aggttctttt | gtttgtactc | cttctgggtt | tttcgttgtg | tttcgggaag | 60 |
| ttccccattt | acacgatacc | agacgaactt | ggtccctgga | gccctattga | catacaccat | 120 |
| ctcagctgtc | caaataacct | ggttgtggag | gatgaaggat | gtaccaacct | gtccgagttc | 180 |
| tcctacatgg | aactcaaagt | gggatacatc | tcagccatca | aagtgaacgg | gttcacttgc | 240 |
| acaggtgttg | tgacagaggc | agagacctac | accaactttg | ttggttatgt | cacaaccaca | 300 |
| ttcaagagaa | agcatttccg | ccccacccca | gacgcatgta | gagccgcgta | taactggaag | 360 |
| atggccggtg | accccagata | tgaagagtcc | ctacacaatc | catccccga | ctaccactgg | 420 |
| cttcgaactg | taagaaccac | caaagagtcc | ctcattatca | tatccccaag | tgtgacagat | 480 |
| ttggacccat | atgacaaatc | ccttcactca | agggtcttcc | ctggcggaaa | gtgctcagga | 540 |
| ataacggtgt | cctctaccta | ctgctcaact | aaccatgatt | acaccatttg | gatgcccgag | 600 |
| aatccgagac | caaggacacc | ttgtgacatt | tttaccaata | gcagagggaa | gagagcatcc | 660 |
| aacgggaaca | agacttgcgg | ctttgtggat | gaaagaggcc | tgtataagtc | tctaaaagga | 720 |
| gcatgcaggc | tcaagttatg | tggagttctt | ggacttagac | ttatggatgg | aacatgggtc | 780 |
| gcgatgcaaa | catcagatga | gaccaaatgg | tgccctccag | atcagttggt | gaatttgcac | 840 |
| gactttcgct | cagacgagat | cgagcatctc | gttgtggagg | agttagttaa | gaaaagagag | 900 |
| gaatgtctgg | atgcattaga | gtccatcatg | accaccaagt | cagtaagttt | cagacgtctc | 960 |
| agtcacctga | gaaacttgt | cccagggttt | ggaaaagcat | ataccatatt | caacaaaacc | 1020 |
| ttgatggagg | ctgatgctca | ctacaagtca | gtccggacct | ggaatgagat | catcccctca | 1080 |
| aaagggtgtt | tgaaagttgg | aggaaggtgc | catcctcatg | tgaacgggt | gttttttcaat | 1140 |

```
ggtataatat tagggcctga cgaccatgtc ctaatcccag agatgcaatc atccctcctc    1200
cagcaacata tggagttgtt ggaatcttca gttatccccc tgatgcaccc cctggcagac    1260
ccttctacag ttttcaaaga aggtgatgag gctgaggatt tgttgaagt tcacctcccc    1320 gatgtgtaca aacagatctc aggggttgac ctgggtctcc cgaactgggg aaagtatgta    1380
ttgatgactg caggggccat gattggcctg tgttgatat tttccctaat gacatggtgc    1440
agagttggta tccatctttg cattaaatta aagcacacca agaaaagaca gatttataca    1500
gacatagaga tgaaccgact tggaaagtaa                                    1530
```

<210> SEQ ID NO 42
<211> LENGTH: 1497
<212> TYPE: DNA
<213> ORGANISM: Artificial Sequence
<220> FEATURE:
<223> OTHER INFORMATION: Envelope-LCMV

<400> SEQUENCE: 42

```
atgggtcaga ttgtgacaat gtttgaggct ctgcctcaca tcatcgatga ggtgatcaac      60
attgtcatta ttgtgcttat cgtgatcacg ggtatcaagg ctgtctacaa ttttgccacc     120
tgtgggatat tcgcattgat cagtttccta cttctggctg gcaggtcctg tggcatgtac     180
ggtcttaagg acccgacat ttacaaagga gtttaccaat ttaagtcagt ggagtttgat     240
atgtcacatc tgaacctgac catgcccaac gcatgttcag ccaacaactc ccaccattac     300
atcagtatgg ggacttctgg actagaattg accttcacca atgattccat catcagtcac     360
aacttttgca atctgaccct tgccttcaac aaaaagacct tgaccacac actcatgagt     420 atagtttcga gcctacacct cagtatcaga gggaactcca actataaggc agtatcctgc     480
gacttcaaca atggcataac catccaatac aacttgacat tctcagatcg acaaagtgct     540
cagagccagt gtagaacctt cagaggtaga gtcctagata tgtttagaac tgccttcggg     600
gggaaataca tgaggagtgg ctggggctgg acaggctcag atggcaagac cacctggtgt     660
agccagacga gttaccaata cctgattata caaatagaa cctgggaaaa ccactgcaca     720
tatgcaggtc cttttgggat gtccaggatt ctcctttccc aagagaagac taagttcttc     780
actaggagac tagcgggcac attcacctgg actttgtcag actcttcagg ggtggagaat     840
ccaggtggtt attgcctgac caaatggatg attcttgctg cagagcttaa gtgtttcggg     900
aacacagcag ttgcgaaatg caatgtaaat catgatgccg aattctgtga catgctgcga     960
ctaattgact acaacaaggc tgctttgagt aagttcaaag aggacgtaga atctgccttg    1020
cacttattca aaacaacagt gaattctttg atttcagatc aactactgat gaggaaccac    1080
ttgagagatc tgatggggt gccatattgc aattactcaa agttttggta cctagaacat    1140
gcaaagaccg gcgaaactag tgtccccaag tgctggcttg tcaccaatgg ttcttactta    1200
aatgagaccc acttcagtga tcaaatcgaa caggaagccg ataacatgat tacagagatg    1260
ttgaggaagg attacataaa gaggcagggg agtaccccc tagcattgat ggaccttctg    1320
atgttttcca catctgcata tctagtcagc atccttcctg accttgtcaa aataccaaca    1380
cacaggcaca taaaggtgg ctcatgtcca aagccacacc gattaaccaa caaaggaatt    1440
tgtagttgtg gtgcatttaa ggtgcctggt gtaaaaaccg tctggaaaag acgctga      1497
```

<210> SEQ ID NO 43
<211> LENGTH: 1692
<212> TYPE: DNA

<213> ORGANISM: Artificial Sequence
<220> FEATURE:
<223> OTHER INFORMATION: Envelope-FPV

<400> SEQUENCE: 43
atgaacactc aaatcctggt tttcgccctt gtggcagtca tccccacaaa tgcagacaaa 60
atttgtcttg gacatcatgc tgtatcaaat ggcaccaaag taaacacact cactgagaga 120
ggagtagaag ttgtcaatgc aacggaaaca gtggagcgga caaacatccc caaaatttgc 180
tcaaaaggga aaagaaccac tgatcttggc caatgcggac tgttagggac cattaccgga 240
ccacctcaat gcgaccaatt tctagaattt tcagctgatc taataatcga gagacgagaa 300
ggaaatgatg tttgttaccc ggggaagttt gttaatgaag aggcattgcg acaaatcctc 360
agaggatcag gtgggattga caaagaaaca atgggattca catatagtgg aataaggacc 420
aacggaacaa ctagtgcatg tagaagatca gggtcttcat tctatgcaga aatggagtgg 480
ctcctgtcaa atacagacaa tgctgctttc ccacaaatga caaaatcata caaaaacaca 540
aggagagaat cagctctgat agtctgggga atccaccatt caggatcaac caccgaacag 600
accaaactat atgggagtgg aaataaactg ataacagtcg ggagttccaa atatcatcaa 660
tcttttgtgc cgagtccagg aacacgaccg cagataaatg gccagtccgg acggattgat 720
tttcattggt tgatcttgga tcccaatgat acagttactt ttagtttcaa tggggctttc 780
atagctccaa atcgtgccag cttcttgagg ggaaagtcca tggggatcca gagcgatgtg 840
caggttgatg ccaattgcga aggggaatgc taccacagtg gagggactat aacaagcaga 900
ttgccttttc aaaacatcaa tagcagagca gttggcaaat gcccaagata tgtaaaacag 960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggtttcag gcatcagaat gcacaaggag aaggaactgc agcagactac 1140
aaaagcaccc aatcggcaat tgatcagata accggaaagt taaatagact cattgagaaa 1200
accaaccagc aatttgagct aatagataat gaattcactg aggtggaaaa gcagattggc 1260
aatttaatta actggaccaa agactccatc acagaagtat ggtcttacaa tgctgaactt 1320
cttgtggcaa tggaaaacca gcacactatt gatttggctg attcagagat gaacaagctg 1380
tatgagcgag tgaggaaaca attaagggaa aatgctgaag aggatggcac tggttgcttt 1440
gaaatttttc ataaatgtga cgatgattgt atggctagta taaggaacaa tacttatgat 1500
cacagcaaat acagagaaga agcgatgcaa aatagaatac aaattgaccc agtcaaattg 1560
agtagtggct acaaagatgt gatactttgg tttagcttcg gggcatcatg ctttttgctt 1620
cttgccattg caatgggcct tgttttcata tgtgtgaaga acggaaacat gcggtgcact 1680
atttgtatat aa 1692

<210> SEQ ID NO 44
<211> LENGTH: 1266
<212> TYPE: DNA
<213> ORGANISM: Artificial Sequence
<220> FEATURE:
<223> OTHER INFORMATION: Envelope-RRV

<400> SEQUENCE: 44
agtgtaacag agcactttaa tgtgtataag gctactagac catacctagc acattgcgcc 60
gattgcgggg acgggtactt ctgctatagc ccagttgcta tcgaggagat ccgagatgag 120
gcgtctgatg gcatgcttaa gatccaagtc tccgcccaaa taggtctgga caaggcaggc 180

| | |
|---|---|
| acccacgccc acacgaagct ccgatatatg gctggtcatg atgttcagga atctaagaga | 240 |
| gattccttga gggtgtacac gtccgcagcg tgctccatac atgggacgat gggacacttc | 300 |
| atcgtcgcac actgtccacc aggcgactac ctcaaggttt cgttcgagga cgcagattcg | 360 |
| cacgtgaagg catgtaaggt ccaatacaag cacaatccat tgccggtggg tagagagaag | 420 |
| ttcgtggtta gaccacactt tggcgtagag ctgccatgca cctcatacca gctgacaacg | 480 |
| gctcccaccg acgaggagat tgacatgcat acaccgccag atataccgga tcgcaccctg | 540 |
| ctatcacaga cggcgggcaa cgtcaaaata acagcaggcg gcaggactat caggtacaac | 600 |
| tgtacctgcg gccgtgacaa cgtaggcact accagtactg acaagaccat caacacatgc | 660 |
| aagattgacc aatgccatgc tgccgtcacc agccatgaca aatggcaatt tacctctcca | 720 |
| tttgttccca gggctgatca gacagctagg aaaggcaagg tacacgttcc gttccctctg | 780 |
| actaacgtca cctgccgagt gccgttggct cgagcgccgg atgccaccta tggtaagaag | 840 |
| gaggtgaccc tgagattaca cccagatcat ccgacgctct tctcctatag gagtttagga | 900 |
| gccgaaccgc acccgtacga ggaatggggtt gacaagttct ctgagcgcat catcccagtg | 960 |
| acggaagaag ggattgagta ccagtggggc aacaacccgc cggtctgcct gtgggcgcaa | 1020 |
| ctgacgaccg agggcaaacc ccatggctgg ccacatgaaa tcattcagta ctattatgga | 1080 |
| ctataccccg ccgccactat tgccgcagta tccggggcga gtctgatggc cctcctaact | 1140 |
| ctggcggcca catgctgcat gctggccacc gcgaggagaa agtgcctaac accgtacgcc | 1200 |
| ctgacgccag gagcggtggt accgttgaca ctggggctgc tttgctgcgc accgagggcg | 1260 |
| aatgca | 1266 |

<210> SEQ ID NO 45
<211> LENGTH: 1938
<212> TYPE: DNA
<213> ORGANISM: Artificial Sequence
<220> FEATURE:
<223> OTHER INFORMATION: Envelope-MLV 10A1

<400> SEQUENCE: 45

| | |
|---|---|
| atggaaggtc cagcgttctc aaaacccctt aaagataaga ttaacccgtg gaagtcctta | 60 |
| atggtcatgg gggtctattt aagagtaggg atggcagaga gcccccatca ggtctttaat | 120 |
| gtaacctgga gagtcaccaa cctgatgact gggcgtaccg ccaatgccac ctcccttta | 180 |
| ggaactgtac aagatgcctt ccaagattta tattttgatc tatgtgatct ggtcggagaa | 240 |
| gagtgggacc cttcagacca ggaaccatat gtcgggtatg ctgcaaaata ccccggaggg | 300 |
| agaaagcgga cccggacttt tgactttttac gtgtgccctg gcataccgt aaaatcgggg | 360 |
| tgtgggggc aagagaggg ctactgtggt gaatgggggtt gtgaaaccac cggacaggct | 420 |
| tactggaagc ccacatcatc atgggaccta atctccctta agcgcggtaa cacccctgg | 480 |
| gacacgggat gctccaaaat ggcttgtggc ccctgctacg acctctccaa gtatccaat | 540 |
| tccttccaag gggctactcg agggggcaga tgcaaccctc tagtcctaga attcactgat | 600 |
| gcaggaaaaa aggctaattg gacggggccc aaatcgtggg gactgagact gtaccggaca | 660 |
| ggaacagatc ctattaccat gttctccctg acccgccagg tcctcaatat agggcccgc | 720 |
| atccccattg ggcctaatcc cgtgatcact ggtcaactac cccctccg accgtgcag | 780 |
| atcaggctcc ccaggcctcc tcagcctcct cctacaggcg cagcctctat agtccctgag | 840 |
| actgccccac cttctcaaca acctgggacg ggagacaggc tgctaaacct ggtagaagga | 900 |

```
gcctatcagg cgcttaacct caccaatccc gacaagaccc aagaatgttg gctgtgctta      960
gtgtcgggac ctccttatta cgaaggagta gcggtcgtgg gcacttatac caatcattct     1020
accgccccgg ccagctgtac ggccacttcc aacataagc ttaccctatc tgaagtgaca      1080
ggacagggcc tatgcatggg agcactacct aaaactcacc aggccttatg taacaccacc     1140
caaagtgccg gctcaggatc ctactacctt gcagcacccg ctggaacaat gtgggcttgt     1200
agcactggat tgactccctg cttgtccacc acgatgctca atctaaccac agactattgt     1260
gtattagttg agctctggcc cagaataatt taccactccc ccgattatat gtatggtcag     1320
cttgaacagc gtaccaaata taagagggag ccagtatcgt tgaccctggc ccttctgcta     1380
ggaggattaa ccatgggagg gattgcagct ggaataggga cggggaccac tgccctaatc     1440
aaaacccagc agtttgagca gcttcacgcc gctatccaga cagacctcaa cgaagtcgaa     1500
aaatcaatta ccaacctaga aaagtcactg acctcgttgt ctgaagtagt cctacagaac     1560
cgaagaggcc tagatttgct cttcctaaaa gagggaggtc tctgcgcagc cctaaaagaa     1620
gaatgttgtt tttatgcaga ccacgggga ctagtgagac acagcatggc caaactaagg     1680
gaaaggctta atcagagaca aaaactattt gagtcaggcc aaggttggtt cgaagggcag     1740
tttaatagat ccccctggtt taccaccttta atctccacca tcatgggacc tctaatagta     1800
ctcttactga tcttactctt tggaccctgc attctcaatc gattggtcca atttgttaaa     1860
gacaggatct cagtggtcca ggctctggtt ttgactcaac aatatcacca gctaaaacct     1920
atagagtacg agccatga                                                   1938

<210> SEQ ID NO 46
<211> LENGTH: 2030
<212> TYPE: DNA
<213> ORGANISM: Artificial Sequence
<220> FEATURE:
<223> OTHER INFORMATION: Envelope-Ebola

<400> SEQUENCE: 46
atgggtgtta caggaatatt gcagttacct cgtgatcgat tcaagaggac atcattcttt       60
ctttgggtaa ttatcctttt ccaaagaaca ttttccatcc cacttggagt catccacaat      120
agcacattac aggttagtga tgtcgacaaa ctggtttgcc gtgacaaact gtcatccaca      180
aatcaattga gatcagttgg actgaatctc gaagggaatg gagtggcaac tgacgtgcca      240
tctgcaacta aagatggggg cttcaggtcc ggtgtcccac caaaggtggt caattatgaa      300
gctggtgaat gggctgaaaa ctgctacaat cttgaaatca aaaaacctga cgggagtgag      360
tgtctaccag cagcgccaga cgggattcgg gcttccccc ggtgccggta tgtgcacaaa      420
gtatcaggaa cgggaccgtg tgccggagac tttgccttcc acaaagaggg tgctttcttc      480
ctgtatgacc gacttgcttc cacagttatc taccgaggaa cgactttcgc tgaaggtgtc      540
gttgcatttc tgatactgcc ccaagctaag aaggacttct tcagctcaca ccccttgaga      600
gagccggtca atgcaacgga ggacccgtct agtggctact attctaccac aattagatat      660
caagctaccg ttttggaac caatgagaca gagtatttgt tcgaggttga caatttgacc      720
tacgtccaac ttgaatcaag attcacacca cagtttctgc tccagctgaa tgagacaata      780
tatacaagtg ggaaaaggag caataccacg ggaaaactaa tttggaaggt caaccccgaa      840
attgatacaa caatcgggga gtgggccttc tgggaaacta aaaaaacctc actagaaaaa      900
ttcgcagtga agagttgtct ttcacagctg tatcaaacag agccaaaaac atcagtggtc      960
agagtccggc gcgaacttct tccgacccag ggaccaacac aacaactgaa gaccacaaaa     1020
```

```
tcatggcttc agaaaattcc tctgcaatgg ttcaagtgca cagtcaagga agggaagctg    1080
cagtgtcgca tctgacaacc cttgccacaa tctccacgag tcctcaaccc cccacaacca    1140
aaccaggtcc ggacaacagc acccacaata cacccgtgta taaacttgac atctctgagg    1200
caactcaagt tgaacaacat caccgcagaa cagacaacga cagcacagcc tccgacactc    1260
cccccgccac gaccgcagcc ggaccccgtaa agcagagaa caccaacacg agcaagggta    1320
ccgacctcct ggaccccgcc accacaacaa gtccccaaaa ccacagcgag accgctggca    1380
acaacaacac tcatcaccaa gataccggag aagagagtgc cagcagcggg aagctaggct    1440
taattaccaa tactattgct ggagtcgcag gactgatcac aggcgggagg agagctcgaa    1500
gagaagcaat tgtcaatgct caacccaaat gcaaccctaa tttacattac tggactactc    1560
aggatgaagg tgctgcaatc ggactggcct ggataccata tttcgggcca gcagccgagg    1620
gaatttacat agaggggctg atgcacaatc aagatggttt aatctgtggg ttgagacagc    1680
tggccaacga gacgactcaa gctcttcaac tgttcctgag agccacaacc gagctacgca    1740
ccttttcaat cctcaaccgt aaggcaattg atttcttgct gcagcgatgg ggcggcacat    1800
gccacatttt gggaccggac tgctgtatcg aaccacatga ttggaccaag aacataacag    1860
acaaaattga tcagattatt catgattttg ttgataaaac ccttccggac caggggggaca    1920 atgacaattg gtggacagga tggagacaat ggataccggc aggtattgga gttacaggcg    1980
ttataattgc agttatcgct ttattctgta tatgcaaatt tgtcttttag               2030

<210> SEQ ID NO 47
<211> LENGTH: 141
<212> TYPE: DNA
<213> ORGANISM: Artificial Sequence
<220> FEATURE:
<223> OTHER INFORMATION: Left ITR

<400> SEQUENCE: 47
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca    120
actccatcac taggggttcc t                                              141

<210> SEQ ID NO 48
<211> LENGTH: 120
<212> TYPE: DNA
<213> ORGANISM: Artificial Sequence
<220> FEATURE:
<223> OTHER INFORMATION: Prothrombin enhancer

<400> SEQUENCE: 48
gcgagaactt gtgcctcccc gtgttcctgc tctttgtccc tctgtcctac ttagactaat    60
atttgccttg ggtactgcaa acaggaaatg ggggagggac aggagtaggg cggagggtag    120

<210> SEQ ID NO 49
<211> LENGTH: 228
<212> TYPE: DNA
<213> ORGANISM: Artificial Sequence
<220> FEATURE:
<223> OTHER INFORMATION: PolyA

<400> SEQUENCE: 49
gactgtgcct tctagttgcc agccatctgt tgtttgcccc tcccccgtgc cttccttgac    60
cctggaaggt gccactccca ctgtcctttc ctaataaaat gaggaaattg catcgcattg    120
```
tctgagtagg tgtcattcta ttctgggggg tggggtgggg caggacagca agggggagga    180
ttgggaagac aatagcaggc atgctgggga tgcggtgggc tctatggc                 228

<210> SEQ ID NO 50
<211> LENGTH: 141
<212> TYPE: DNA
<213> ORGANISM: Artificial Sequence
<220> FEATURE:
<223> OTHER INFORMATION: Right ITR

<400> SEQUENCE: 50
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc    120
gagcgcgcag ctgcctgcag g                                              141

<210> SEQ ID NO 51
<211> LENGTH: 1470
<212> TYPE: DNA
<213> ORGANISM: Artificial Sequence
<220> FEATURE:
<223> OTHER INFORMATION: E2A

<400> SEQUENCE: 51
ttaaaagtcg aagggggttct cgcgctcgtc gttgtgcgcc gcgctgggga gggccacgtt    60
gcggaactgg tacttgggct gccacttgaa ctcggggatc accagtttgg gcactggggt   120
ctcggggaag gtctcgctcc acatgcgccg gctcatctgc agggcgccca gcatgtcagg   180
cgcggagatc ttgaaatcgc agttgggcc ggtgctctgc gcgcgcgagt tgcggtacac    240
tgggttgcag cactggaaca ccatcagact ggggtacttc acactagcca gcacgctctt   300
gtcgctgatc tgatccttgt ccaggtcctc ggcgttgctc aggccgaacg gggtcatctt   360
gcacagctgg cggcccagga agggcacgct ctgaggcttg tggttacact cgcagtgcac   420
gggcatcagc atcatccccg cgccgcgctg catattcggg tagagggcct tgacgaaggc   480
cgcgatctgc ttgaaagctt gctgggcctt ggccccctcg ctgaaaaaca ggccgcagct   540
cttcccgctg aactgattat tcccgcaccc ggcatcatgg acgcagcagc gcgcgtcatg   600
gctggtcagt tgcaccacgc tccgtcccca gcggttctgg gtcaccttgg ccttgctggg   660
ttgctccttc agcgcacgct gcccgttctc actggtcaca tccatctcca ccacgtggtc   720
cttgtggatc atcaccgtcc catgcagaca cttgagctgg ccttccacct cggtgcagcc   780
gtggtcccac agggcactgc cggtgcactc ccagttcttg tgcgcgatcc cgctgtggct   840
gaagatgtaa ccttgcaaca ggcgacccat gatggtgcta aagctcttct gggtggtgaa   900
ggtcagttgc agaccgcggg cctcctcgtt catccaggtc tggcacatct tttggaagat   960
ctcggtctgc tcgggcatga gcttgtaagc atcgcgcagg ccgctgtcga cgcggtagcg   1020
ttccatcagc acattcatgg tatccatgcc cttctcccag gacgagacca gaggcagact   1080 caggggggttg cgcacgttca ggacaccggg ggtcgcgggc tcgacgatgc gttttccgtc   1140
cttgccttcc ttcaacagaa ccggcggctg gctgaatccc actcccacga tcacggcttc   1200
ttcctgggga atctcttcgt ctgggtctac cttggtcaca tgcttggtct ttctggcttg   1260
cttctttttt ggagggctgt ccacggggac cacgtcctcc tcggaagacc cggatcccac   1320
ccgctgatac tttcggcgct tggttggcag aggaggtggc ggcgaggggc tcctctcctg   1380
ctccggcgga tagcgcgctg aaccgtgcc cggggcggga gtggcctctc ggtccatgaa    1440
ccggcgcacg tcctgactgc cgccggccat                                     1470

<210> SEQ ID NO 52
<211> LENGTH: 393
<212> TYPE: DNA
<213> ORGANISM: Artificial Sequence
<220> FEATURE:
<223> OTHER INFORMATION: E4

<400> SEQUENCE: 52

| tcatgtatct | ttattgattt | ttacaccagc | acgggtagtc | agtctcccac | caccagccca | 60 |
| tttcacagtg | taaacaattc | tctcagcacg | gtggcctta  | aatagggcaa | tattctgatt | 120 |
| agtgcgggaa | ctggacttgg | ggtctataat | ccacacagtt | tcctggcgag | ccaaacgggg | 180 |
| gtcggtgatt | gagatgaagc | cgtcctctga | aaagtcatcc | aagcgagcct | cacagtccaa | 240 |
| ggtcacagta | ttatgataat | ctgcatgatc | acaatcgggc | aacagggat  | gttgttcagt | 300 |
| cagtgaagcc | ctggtttcct | catcagatcg | tggtaaacgg | gccctgcgat | atggatgatg | 360 |
| gcggagcgag | ctggattgaa | tctcggtttg | cat | | | 393 |

<210> SEQ ID NO 53
<211> LENGTH: 162
<212> TYPE: DNA
<213> ORGANISM: Artificial Sequence
<220> FEATURE:
<223> OTHER INFORMATION: VA RNA

<400> SEQUENCE: 53

| agcgggcact | cttccgtggt | ctggtggata | aattcgcaag | ggtatcatgg | cggacgaccg | 60 |
| gggttcgagc | cccgtatccg | gccgtccgcc | gtgatccatg | cggttaccgc | ccgcgtgtcg | 120 |
| aacccaggtg | tgcgacgtca | gacaacgggg | gagtgctcct | tt | | 162 |

<210> SEQ ID NO 54
<211> LENGTH: 2208
<212> TYPE: DNA
<213> ORGANISM: Artificial Sequence
<220> FEATURE:
<223> OTHER INFORMATION: AAV2 Rep

<400> SEQUENCE: 54

| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | gacccttcaa | cggactcgac | 180 |
| aagggagagc | cggtcaacga | ggcagacgcc | gcggccctcg | agcacgacaa | agcctacgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccgga | 480 |
| aaggcgggcc | agcagcctgc | aagaaaaaga | ttgaattttg | gtcagactgg | agacgcagac | 540 |
| tcagtacctg | acccccagcc | tctcggacag | ccaccagcag | cccctctgg  | tctgggaact | 600 |
| aatacgatgg | ctacaggcag | tggcgcacca | atggcagaca | ataacgaggg | cgccgacgga | 660 |
| gtgggtaatt | cctcgggaaa | ttggcattgc | gattccacat | ggatgggcga | cagagtcatc | 720 |
| accaccagca | cccgaacctg | ggcccctgcc | cctacaacaa | ccacctcta  | caaacaaatt | 780 |
| tccagccaat | caggagcctc | gaacgacaat | cactactttg | gctacagcac | cccttggggg | 840 |

```
tattttgact tcaacagatt ccactgccac ttttcaccac gtgactggca aagactcatc    900
aacaacaact ggggattccg acccaagaga ctcaacttca agctctttaa cattcaagtc    960
aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcatttttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
cacccctcct cacagattct catcaagaac acccccgtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact caacaagtc tgttaatgtg gactttactg tggacactaa tggcgtgtat   2160
tcagagcctc gccccattgg caccagatac ctgactcgta atctgtaa                2208
```

<210> SEQ ID NO 55
<211> LENGTH: 1866
<212> TYPE: DNA
<213> ORGANISM: Artificial Sequence
<220> FEATURE:
<223> OTHER INFORMATION: AAV2 Cap

<400> SEQUENCE: 55

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcaccctga ccgtggccga aaagctgcag    180
cgcgactttc tgacggaatg cgccgtgtg agtaaggccc cggaggccct tttctttgtg    240
caatttgaga agggagagag ctacttccac atgcacgtgc tcgtggaaac caccggggtg    300
aaaatccatg ttttgggacg ttttcctgagt cagattcgcg aaaaactgat tcagagaatt    360
taccgcggga tcgagccgac tttgccaaac tggttcgcgg tcacaaagac cagaaatggc    420
gccgaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
```

```
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg gcctgcaac taccgggaag    1020 accaacatcg cggaggccat agcccacact gtgcccttct acgggtgcgt aaactggacc    1080
aatgagaact ttcccttcaa cgactgtgtc gacaagatgg tgatctggtg ggaggagggg    1140
aagatgaccg ccaaggtcgt ggagtcggcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacaggtac caaaacaaat gttctcgtca cgtgggcatg    1620
aatctgatgc tgtttccctg cagacaatgc gagagaatga atcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caataa                                                                1866
```

<210> SEQ ID NO 56
<211> LENGTH: 1227
<212> TYPE: DNA
<213> ORGANISM: Artificial Sequence
<220> FEATURE:
<223> OTHER INFORMATION: DNA Fragment containing RRE and rabbit beta
      globin poly A

<400> SEQUENCE: 56

```
tctagaagga gctttgttcc ttgggttctt gggagcagca ggaagcacta tgggcgcagc     60
gtcaatgacg ctgacggtac aggccagaca attattgtct ggtatagtgc agcagcagaa    120
caatttgctg agggctattg aggcgcaaca gcatctgttg caactcacag tctgggcat    180 caagcagctc caggcaagaa tcctggctgt ggaaagatac ctaaaggatc aacagctcct    240
agatcttttt ccctctgcca aaaattatgg ggacatcatg aagccccttg agcatctgac    300
ttctggctaa taaaggaaat ttattttcat tgcaatagtg tgttggaatt ttttgtgtct    360
ctcactcgga aggacatatg ggagggcaaa tcatttaaaa catcagaatg agtatttggt    420
ttagagtttg gcaacatatg ccatatgctg gctgccatga acaaaggtgg ctataaagag    480
gtcatcagta tatgaaacag ccccctgctg tccattcctt attccataga aaagccttga    540
cttgaggtta gatttttttt atattttgtt ttgtgttatt ttttctttaa acatccctaa    600
aattttcctt acatgtttta ctagccagat ttttcctcct ctcctgacta ctcccagtca    660
tagctgtccc tcttctctta tgaagatccc tcgacctgca gcccaagctt ggcgtaatca    720
tggtcatagc tgtttcctgt gtgaaattgt tatccgctca caattccaca caacatacga    780
gccggaagca taaagtgtaa agcctggggt gcctaatgag tgagctaact cacattaatt    840
```

```
gcgttgcgct cactgcccgc tttccagtcg ggaaacctgt cgtgccagcg gatccgcatc    900
tcaattagtc agcaaccata gtcccgcccc taactccgcc catcccgccc ctaactccgc    960
ccagttccgc ccattctccg ccccatggct gactaatttt ttttatttat gcagaggccg   1020
aggccgcctc ggcctctgag ctattccaga agtagtgagg aggcttttt ggaggcctag   1080 gcttttgcaa aaagctaact tgtttattgc agcttataat ggttacaaat aaagcaatag   1140
catcacaaat ttcacaaata aagcattttt ttcactgcat tctagttgtg gtttgtccaa   1200
actcatcaat gtatcttatc acccggg                                        1227
```

<210> SEQ ID NO 57
<211> LENGTH: 2312
<212> TYPE: DNA
<213> ORGANISM: Artificial Sequence
<220> FEATURE:
<223> OTHER INFORMATION: hPAH with fill 5' and 3' UTR

<400> SEQUENCE: 57

```
ggcacgaggt acctgaggcc ctaaaaagcc agagacctca ctcccgggga gccagcatgt     60
ccactgcggt cctggaaaac ccaggcttgg gcaggaaact ctctgacttt ggacaggaaa    120
caagctatat tgaagacaac tgcaatcaaa atggtgccat atcactgatc ttctcactca    180
aagaagaagt tggtgcattg gccaaagtat tgcgcttatt tgaggagaat gatgtaaacc    240
tgacccacat tgaatctaga ccttctcgtt taaagaaaga tgagtatgaa ttttttcaccc    300 atttggataa acgtagcctg cctgctctga caaacatcat caagatcttg aggcatgaca    360
ttggtgccac tgtccatgag ctttcacgag ataagaagaa agacacagtg ccctggttcc    420
caagaaccat tcaagagctg gacagatttg ccaatcagat tctcagctat ggagcggaac    480
tggatgctga ccaccctggt tttaaagatc ctgtgtaccg tgcaagacgg aagcagtttg    540
ctgacattgc ctacaactac cgccatgggc agcccatccc tcgagtggaa tacatggagg    600
aagaaaagaa aacatggggc acagtgttca agactctgaa gtccttgtat aaaacccatg    660
cttgctatga gtacaatcac attttttccac ttcttgaaaa gtactgtggc ttccatgaag    720
ataacattcc ccagctggaa gacgtttctc agttcctgca gacttgcact ggtttccgcc    780
tccgacctgt agctggcctg ctttcctctc gggatttctt gggtggcctg gccttccgag    840
tcttccactg cacacagtac atcagacatg gatccaagcc catgtatacc cccgaacctg    900
acatctgcca tgagctgttg ggacatgtgc ccttgttttc agatcgcagc tttgcccagt    960
tttcccagga aattggcctt gcctctctgg gtgcacctga tgaatacatt gaaaagctcg   1020
ccacaattta ctggtttact gtggagtttg gctctgcaa acaaggagac tccataaagg   1080
catatggtgc tgggctcctg tcatcctttg gtgaattaca gtactgctta tcagagaagc   1140
caaagcttct cccctggag ctggagaaga cagccatcca aaattacact gtcacggagt   1200 tccagccct gtattacgtg gcagagagtt ttaatgatgc caaggagaaa gtaaggaact   1260 tgctgccac aatacctcgg cccttctcag ttcgctacga cccatacacc caaaggattg   1320
aggtcttgga caatacccag cagcttaaga ttttggctga ttccattaac agtgaaattg   1380
gaatcctttg cagtgccctc cagaaaataa agtaaagcca tggacagaat gtggtctgtc   1440
agctgtgaat ctgttgatgg agatccaact atttctttca tcagaaaaag tccgaaaagc   1500
aaaccttaat ttgaaataac agccttaaat cctttacaag atggagaaac aacaaataag   1560
tcaaaataat ctgaaatgac aggatatgag tacatactca agagcataat ggtaaatctt   1620
```

```
ttggggtcat ctttgattta gagatgataa tcccatactc tcaattgagt taaatcagta    1680
atctgtcgca tttcatcaag attaattaaa atttgggacc tgcttcattc aagcttcata    1740
tatgctttgc agagaactca taaaggagca ataaggctaa atgtaaaac ccaagactgt    1800 cattagaatt gaattattgg gcttaatata aatcgtaacc tatgaagttt attttttatt    1860
ttagttaact atgattccaa ttactacttt gttattgtac ctaagtaaat tttctttaag    1920
tcagaagccc attaaaatag ttacaagcat tgaacttctt tagtattata ttaatataaa    1980
aacatttttg tatgttttat tgtaatcata aatactgctg tataaggtaa taaaactctg    2040
cacctaatcc ccataacttc cagtatcatt ttccaattaa ttatcaagtc tgttttggga    2100
aacactttga ggacatttat gatgcagcag atgttgacta aaggcttggt tggtagatat    2160
tcaggaaatg ttcactgaat aaataagtaa atacattatt gaaaagcaaa tctgtataaa    2220
tgtgaaattt ttatttgtat tagtaataaa acattagtag tttaaacaaa aaaaaaaaa    2280 aaaaaaaaaa aaaaaaaact cgactctaga tt    2312
```

<210> SEQ ID NO 58
<211> LENGTH: 1704
<212> TYPE: DNA
<213> ORGANISM: Artificial Sequence
<220> FEATURE:
<223> OTHER INFORMATION: hPAH with full 5' UTR and truncated 3' UTR

<400> SEQUENCE: 58

```
ggcacgaggt acctgaggcc ctaaaaagcc agagacctca ctcccgggga gccagcatgt      60
ccactgcggt cctggaaaac ccaggcttgg gcaggaaact ctctgacttt ggacaggaaa     120
caagctatat tgaagacaac tgcaatcaaa atggtgccat atcactgatc ttctcactca     180
aagaagaagt tggtgcattg gccaaagtat tgcgcttatt tgaggagaat gatgtaaacc     240
tgacccacat tgaatctaga ccttctcgtt taaagaaaga tgagtatgaa tttttcaccc     300
atttggataa acgtagcctg cctgctctga caaacatcat caagatcttg aggcatgaca     360
ttggtgccac tgtccatgag cttttcacgag ataagaagaa agacacagtg ccctggttcc     420
caagaaccat tcaagagctg gacagatttg ccaatcagat tctcagctat ggagcggaac     480
tggatgctga ccaccctggt tttaaagatc ctgtgtaccg tgcaagacgg aagcagtttg     540
ctgacattgc ctacaactac cgccatgggc agcccatccc tcgagtggaa tacatggagg     600 aagaaagaa acatggggc acagtgttca agactctgaa gtccttgtat aaaacccatg     660
cttgctatga gtacaatcac atttttccac ttcttgaaaa gtactgtggc ttccatgaag     720
ataacattcc ccagctggaa gacgtttctc agttcctgca gacttgcact ggtttccgcc     780
tccgacctgt agctggcctg ctttcctctc gggatttctt gggtggcctg gccttccgag     840
tcttccactg cacacagtac atcagacatg gatccaagcc catgtatacc cccgaacctg     900
acatctgcca tgagctgttg ggacatgtgc ccttgttttc agatcgcagc tttgcccagt     960
tttcccagga aattggcctt gcctctctgg gtgcacctga tgaatacatt gaaaagctcg    1020
ccacaattta ctggtttact gtggagtttg gctctgcaa acaaggagac tccataaagg    1080
catatggtgc tgggctcctg tcatcctttg gtgaattaca gtactgctta tcagagaagc    1140
caaagcttct cccctggag ctggagaaga cagccatcca aaattacact gtcacggagt    1200
tccagcccct gtattacgtg gcagagagtt ttaatgatgc caaggagaaa gtaaggaact    1260
ttgctgccac aatacctcgg cccttctcag ttcgctacga cccatacacc caaaggattg    1320
aggtcttgga caataccag cagcttaaga ttttggctga ttccattaac agtgaaattg    1380
```

```
gaatcctttg cagtgccctc cagaaaataa agtaaagcca tggacagaat gtggtctgtc  1440
agctgtgaat ctgttgatgg agatccaact atttctttca tcagaaaaag tccgaaaagc  1500
aaaccttaat ttgaaataac agccttaaat cctttacaag atggagaaac aacaaataag  1560
tcaaaataat ctgaaatgac aggatatgag tacatactca agagcataat ggtaaatctt  1620
ttggggtcat ctttgattta gagatgataa tcccatactc tcaattgagt taaatcagta  1680
atctgtcgca tttcatcaag atta                                          1704
```

COMPOSITIONS AND METHODS FOR TREATING PHENYLKETONURIA

CROSS-REFERENCE TO RELATED APPLICATIONS

This application claims priority to: U.S. Provisional Patent Application No. 62/480,962 filed on Apr. 3, 2017 entitled "COMPOSITIONS AND METHODS FOR TREATING PHENYLKETONURIA", and U.S. Provisional Patent Application No. 62/491,118 filed on Apr. 27, 2017 entitled "COMPOSITIONS AND METHODS FOR TREATING PHENYLKETONURIA," the disclosures of which are incorporated herein by reference.

FIELD

Aspects of the invention relate to genetic medicines for treating phenylketonuria (PKU). More specifically, aspects of the invention relate to using lentiviral vectors, including PAH-containing lentiviral vectors, to treat PKU.

BACKGROUND

Phenylketonuria (PKU) refers to a heterogeneous group of disorders that can lead to increased concentration of phenylalanine in the blood, or hyperphenylalaninemia, Hyperphenylalaninemia can cause intellectual disability, seizures, behavioral problems, and impaired growth and development in affected children if left untreated. The mechanisms by which hyperphenylalaninemia results in intellectual impairment reflect the surprising toxicity of high dose phenylalanine and involve hypomyelination or demyelination of nervous system tissues. PKU has an average reported incidence rate of 1 in 12,000 in North America, affecting males and females equally. The disorder is most common in people of European or Native American Ancestry and reaches much higher levels in the eastern Mediterranean region.

Neurological changes in patients with PKU have been demonstrated within one month of birth, and magnetic resonance imaging (MRI) in adult PKU patients has shown white matter lesions in the brain. The size and number these lesions relate directly to blood phenylalanine concentration. The cognitive profile of adolescents and adults with PKU compared with control subjects can include significantly reduced IQ, processing speed, motor control and inhibitory abilities, and reduced performance on tests of attention.

The majority of PKU is caused by a deficiency of hepatic phenylalanine hydroxylase (PAH). PAH is a multimeric hepatic enzyme that catalyzes the hydroxylation of phenylalanine (Phe) to tyrosine (Tyr) in the presence of molecular oxygen and catalytic amounts of tetrahydrobiopterin ($BH_4$), its nonprotein cofactor. In the absence of sufficient expression of PAH, phenylalanine levels in the blood increase, leading to hyperphenylalaninemia and harmful side effects in PKU patients. Decreased or absent PAH activity can lead to a deficiency of tyrosine and its downstream products, including melanin, 1-thyroxine and the catecholamine neurotransmitters including dopamine.

PKU can be caused by mutations in PAH and/or a detect in the synthesis or regeneration of PAH cofactors (i.e., $BH_4$). Notably, several PAH mutations have been shown to affect protein folding in the endoplasmic reticulum resulting in accelerated degradation and/or aggregation due to missense mutations (63%) and small deletions 13%) in protein structure that attenuate or largely abolish enzyme catalytic activity.

In general, three major phenotypic groups are used to classify PKU based on blood plasma Phe levels, dietary tolerance to Phe and potential responsiveness to therapy. These groups include classical PKU (Phe>1200 μM), atypical or mild PKU (Phe is 600-1200 μM), and permanent mild hyperphenylalaninemia (HPA, Phe 120-600 μM).

Detection of PKU relies on universal newborn screening (NBS). A drop of blood collected from a heel stick is tested for phenylalanine levels in a screen that is mandatory in all 50 states of the USA.

Currently, lifelong dietary restriction of Phe and $BH_4$ supplementation are the only two available treatment options for PKU, where early therapeutic intervention is critical to ensure optimal clinical outcomes in affected infants. However, costly medication and special low-protein foods imposes a major burden on patients that can lead to malnutrition, psychosocial or neurocognitive complications notable when these products are not fully covered by private health insurance. Moreover, $BH_4$ therapy is primarily effective for treatment of mild hyperphenylalaninemia as related to defects in $BH_4$ biosynthesis, whereas only 20-30% of patients with mild or classical PKU are responsive, Thus, there is an urgent need for new treatment modalities for PKU as an alternative to burdensome Phe-restriction diets. Thus, it would be desirable to develop an alternative method for the treatment of phenylketonuria. Genetic medicines have the potential to effectively treat PKU.

SUMMARY OF THE INVENTION

In an aspect, a viral vector is disclosed. The viral vector comprises a phenylalanine hydroxylase (PAH) sequence for expressing at least one of PAH or a variant thereof, wherein the PAH sequence is truncated. In embodiments, the PAH sequence is truncated at a 3' untranslated region (UTR) of the sequence. In embodiments, the PAH sequence comprises at least one of 80%, 85%, 90%, 95%, or 100% identity with at least one of SEQ ID NO: 2, SEQ ID NO: 3, or SEQ ID NO: 4.

In embodiments, the viral vector further comprises at least one small RNA sequence that is capable of binding to at least one pre-determined complementary mRNA sequence. In embodiments, the at least one pre-determined complementary mRNA sequence comprises a full-length 3' untranslated region (UTR). In embodiments, the at least one pre-determined complementary mRNA sequence is a PAH mRNA sequence. In embodiments, the at least one small RNA sequence comprises a shRNA. In embodiments, the at least one small RNA sequence comprises a sequence having at least one of 80%, 85%, 90%, 95%, or 100% identity with at least one of SEQ ID NO: 5 or SEQ ID NO: 6. In embodiments, the at least one small RNA sequence is under the control of a first promoter, and wherein the PAH sequence is under the control of a second promoter. In embodiments, the first promoter comprises a H1 promoter. In embodiments, the second promoter comprises a liver-specific promoter. In embodiments, the liver-specific promoter comprises a hAAT promoter.

In another aspect, a viral vector is disclosed. The viral vector comprises a phenylalanine hydroxylase (PAH) sequence for expressing at least one of PAH or a variant thereof, and at least one small RNA sequence that is capable of binding to at least one pre-determined complementary mRNA sequence. In embodiments, the PAH sequence comprises at least one of 80%, 85%, 90%, 95%, or 100% identity with SEQ ID NO: 1.

In another aspect, a lentiviral particle produced by a packaging cell and capable of infecting a target cell is disclosed. The lentiviral particle comprises an envelope protein capable of infecting a target cell, and the viral vector comprises a phenylalanine hydroxylase (PAH) sequence for expressing at least one of PAH or a variant thereof, and at least one small RNA sequence that is capable of binding to at least one pre-determined complementary mRNA sequence. In embodiments, the target cell is at least one of a hepatic cell, a muscle cell, an epithelial cell, an endothelial cell, a neural cell, a neuroendocrine cell, an endocrine cell, a lymphocyte, a myeloid cell, a cell present within a solid organ, or cell of a hematopoietic lineage, a hematopoietic stem cell, or a precursor hematopoietic stem cell.

In another aspect, a method of treating phenylketonuria (PKU) in a subject is disclosed. The method comprises administering to the subject a therapeutically effective amount of a lentiviral particle produced by a packaging cell and capable of infecting a target cell, wherein the lentiviral particle comprises an envelope protein capable of infecting a target cell, and a viral vector comprising a phenylalanine hydroxylase (PAH) sequence for expressing at least one of PAH or a variant thereof, and at least one small RNA sequence that is capable of binding to at least one pre-determined complementary mRNA sequence.

In embodiments, the therapeutically effective amount of the lentiviral particle comprises a plurality of single doses of the lentiviral particle. In embodiments, the therapeutically effective amount of the lentiviral particle comprises a single dose of the lentiviral particle. In embodiments, the subject is in utero. In embodiments, the method further comprises diagnosing a PKU genotype in the subject that correlates with a PKU phenotype. In embodiments, the diagnosing occurs during prenatal screening of the subject. In embodiments, the diagnosing occurs prior to the administering.

In another aspect, use of a therapeutically effective amount of a lentiviral particle for treatment of phenylketonuria (PKU) in a subject is disclosed. The lentiviral particle is produced by a packaging cell, is capable of infecting a target cell, and comprises an envelope protein capable of infecting a target cell, and a viral vector. In embodiments, the viral vector comprises a phenylalanine hydroxylase (PAH) sequence for expressing at least one of PAH or a variant thereof, wherein the PAH sequence is truncated. In embodiments, the viral vector comprises a phenylalanine hydroxylase (PAH) sequence for expressing at least one of PAH or a variant thereof, and at least one small RNA sequence that is capable of binding to at least one pre-determined complementary mRNA sequence.

Other aspects and advantages of the inventions described herein will become apparent from the following detailed description, taken in conjunction with the accompanying drawings, which illustrate by way of example the aspects of the inventions.

BRIEF DESCRIPTION OF THE DRAWINGS

FIG. 5 depicts a phenylalanine hydroxylase open reading frame including complete 5' and 3' UTRs.

FIG. 6 depicts a phenylalanine hydroxylase open reading frame including a complete 5' UTR and a truncated 3' UTR.

FIG. 14 depicts data demonstrating results of treating a Pah(enu2) mouse with hAAT-PAH-UTR. FIG. 14A depicts change in weight over 8 weeks for the groups depicted therein.

FIG. 14B depicts change in weight over 8 weeks for the groups depicted therein. FIG. 14C depicts change in weight over 8 weeks for the groups depicted therein. FIG. 14D depicts levels of phenylalanine over 1 month post-treatment.

DETAILED DESCRIPTION

Overview of the Disclosure

Figure 1:
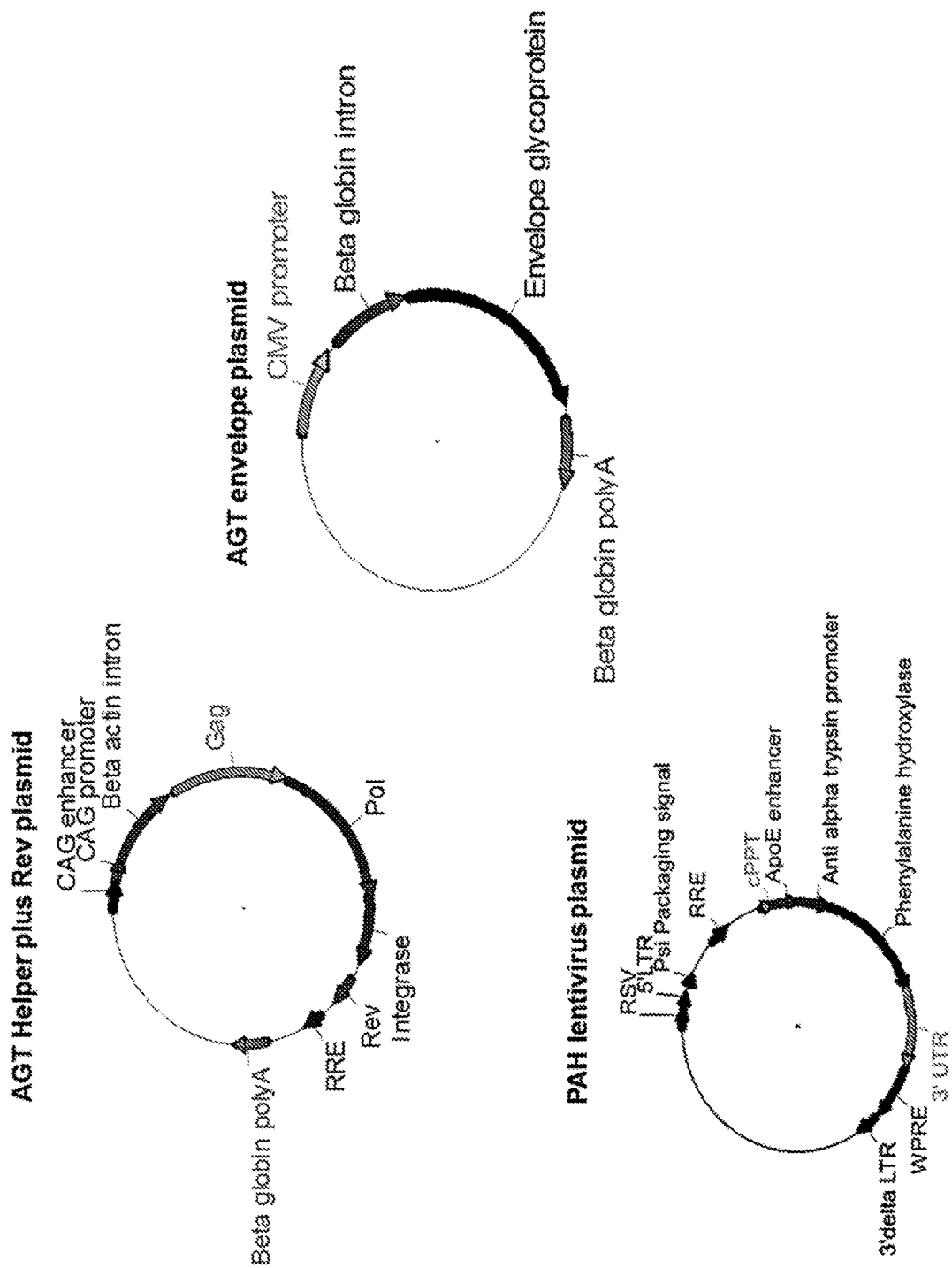
FIG. 1 depicts an exemplary 3-vector lentiviral vector system in a circularized form.

The present disclosure relates to therapeutic vectors and delivery of the same to cells. In embodiments, the therapeutic vectors include PAH sequences or variants thereof. In embodiments, the therapeutic vectors also include a small RNA that targets host (endogenous) PAH expression.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent should be understood to mean providing an active agent to the subject in need of treatment in a form that can be introduced into that individual's body in a therapeutically useful form and therapeutically effective amount.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, the terms "expression", "expressed", or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

As used herein, the term "phenylketonuria", which is also referred to herein as "PKU", refers to the chronic deficiency of phenylalanine hydroxylase, as well as all symptoms related thereto including mild and classical forms of disease. Treatment of "phenylketonuria", therefore, may relate to treatment for all or some of the symptoms associated with PKU.

As used herein, the term "phenylalanine hydroxylase" may also be referred to herein as PAH. Human PAH may also be referred to herein as hPAH. Mouse PAH may also be referred to herein as mPAH.

As used herein, the term "shPAH" refers to a small hairpin RNA targeting PAH.

As used herein, the term "hAAT-hPAH-3'UTR$_{289}$" may also be referred to herein as U$_{289}$, or generally as transgene-expressed truncated hPAH 3'UTR, or generally a truncated 3' UTR.

As used herein, the term "hAAT-hPAH-3'UTR$_{238}$" may also be referred to herein as U$_{238}$, or generally as transgene-expressed truncated hPAH 3'UTR, or generally a truncated 3' UTR.

As used herein, the term "wild type hPAH" may also be referred to herein as "endogenous PAH" or "full-length PAH".

As used herein, the term truncated may also be referred to herein as "shortened" or "without".

As used herein, the term variant may also be referred to herein as analog or variation. A variant refers to any substitution, deletion, or addition to a nucleotide sequence.

As used herein, the term "genetic medicine" or "genetic medicines" refers generally to therapeutics and therapeutic strategies that focus on genetic targets to treat a clinical disease or manifestation. The term "genetic medicine" encompasses gene therapy and the like.

As used herein, the terms "individual," "subject," and "patient" are used interchangeably herein, and refer to any individual mammal subject, e.g., bovine, canine, feline, equine, or human.

As used herein, the term "LV" refers generally to "lentivirus". As an example, reference to "LV-shPAH" is reference to a lentivirus that expresses a shRNA that targets PAH.

As used herein, the term "packaging cell line" refers to any cell line that can be used to express a lentiviral particle.

As used herein, the term "percent identity", in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word length=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "SEQ ID NO" is synonymous with the term "Sequence ID No."

As used herein, "small RNA" refers to non-coding RNA that are generally about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

As used herein, the term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, reference to a lentiviral vector or an adeno-associated viral (AAV) vector. Additionally, as used herein with reference to the lentiviral vector system, the term "vector" is synonymous with the term "plasmid". For example, the 3-vector and 4-vector systems, which include the 2-vector and 3-vector packaging systems, can also be referred to as 3-plasmid and 4-plasmid systems.

As used herein, the term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis. The particular treatment thus will depend on the disease state to be targeted and the current or future state of medicinal therapies and therapeutic approaches. A treatment may have associated toxicities.

Description of Aspects and Embodiments of the Disclosure

In an aspect of the present disclosure, a viral vector is disclosed. The viral vector comprises a therapeutic cargo portion, wherein the therapeutic cargo portion comprises a PAH sequence or a variant thereof. In embodiments, the PAH sequence or the variant is truncated. In embodiments, the portion of the PAH sequence or the variant thereof that is truncated is the 3' untranslated region (UTR) of the PAH sequence or the variant thereof. In embodiments, the PAH sequence or the variant thereof comprises a sequence having at least 80%, or at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with:

(SEQ ID NO: 1)
ATGTCCACTGCGGTCCTGGAAAACCCAGGCTTGGGCAGGAAACTCTCTGA

CTTTGGACAGGAAACAAGCTATATTGAAGACAACTGCAATCAAAATGGTG

CCATATCACTGATCTTCTCACTCAAAGAAGAAGTTGGTGCATTGGCCAAA

GTATTGCGCTTATTTGAGGAGAATGATGTAAACCTGACCCACATTGAATC

TAGACCTTCTCGTTTAAAGAAAGATGAGTATGAATTTTTCACCCATTTGG

ATAAACGTAGCCTGCCTGCTCTGACAAACATCATCAAGATCTTGAGGCAT

GACATTGGTGCCACTGTCCATGAGCTTTCACGAGATAAGAAGAAAGACAC

AGTGCCCTGGTTCCCAAGAACCATTCAAGAGCTGGACAGATTTGCCAATC

AGATTCTCAGCTATGGAGCGGAACTGGATGCTGACCACCCTGGTTTTAAA

GATCCTGTGTACCGTGCAAGACGGAAGCAGTTTGCTGACATTGCCTACAA

CTACCGCCATGGGCAGCCCATCCCTCGAGTGGAATACATGGAGGAAGAAA

AGAAAACATGGGCACAGTGTTCAAGACTCTGAAGTCCTTGTATAAAACC

CATGCTTGCTATGAGTACAATCACATTTTTCCACTTCTTGAAAAGTACTG

TGGCTTCCATGAAGATAACATTCCCCAGCTGGAAGACGTTTCTCAATTCC

TGCAGACTTGCACTGGTTTCCGCCTCCGACCTGTGGCTGGCCTGCTTTCC

TCTCGGGATTTCTTGGGTGGCCTGGCCTTCCGAGTCTTCCACTGCACACA

GTACATCAGACATGGATCCAAGCCCATGTATACCCCCGAACCTGACATCT

GCCATGAGCTGTTGGGACATGTGCCCTTGTTTTCAGATCGCAGCTTTGCC

CAGTTTTCCCAGGAAATTGGCCTTGCCTCTCTGGGTGCACCTGATGAATA

CATTGAAAAGCTCGCCACAATTTACTGGTTTACTGTGGAGTTTGGGCTCT

GCAAACAAGGAGACTCCATAAAGGCATATGGTGCTGGGCTCCTGTCATCC

TTTGGTGAATTACAGTACTGCTTATCAGAGAAGCCAAAGCTTCTCCCCCT

GGAGCTGGAGAAGACAGCCATCCAAAATTACACTGTCACGGAGTTCCAGC

CCCTGTATTACGTGGCAGAGAGTTTTAATGATGCCAAGGAGAAAGTAAGG

AACTTTGCTGCCACAATACCTCGGCCCTTCTCAGTTCGCTACGACCCATA

CACCCAAAGGATTGAGGTCTTGGACAATACCCAGCAGCTTAAGATTTTGG

CTGATTCCATTAACAGTGAAATTGGAATCCTTTGCAGTGCCCTCCAGAAA

ATAAAGTAA;

(SEQ ID NO: 2)
ATGAGCACAGCTGTGTTGGAAAATCCTGGGCTGGGCCGTAAGCTTTCCGA

TTTCGGCCAGGAGACTTCATACATTGAGGACAACTGCAACCAGAATGGGG

CCATTTCTTTGATCTTCAGTCTCAAAGAAGAGGTAGGCGCTCTGGCTAAG

GTCCTGAGGCTGTTTGAGGAAAATGACGTGAATCTGACACACATTGAGTC

TAGGCCTTCCCGACTTAAGAAGGATGAGTATGAGTTCTTCACACACCTGG

ACAAACGATCTCTCCCAGCACTGACCAATATCATCAAGATTCTCAGGCAT

GATATCGGTGCCACGGTCCACGAACTTTCACGCGATAAGAAGAAAGACAC

AGTTCCCTGGTTCCCGAGAACCATTCAGGAACTGGATAGGTTTGCCAATC

AGATTCTGAGCTATGGGGCAGAGTTGGATGCCGACCATCCAGGCTTCAAA

GACCCCGTATATCGGGCTCGGAGAAAGCAGTTTGCAGACATCGCTTACAA

TTACAGGCATGGACAGCCCATCCCTAGAGTGGAGTACATGGAAGAAGGCA

AGAAAACCTGGGGAACGGTGTTTAAGACCCTCAAAAGCCTGTATAAGACC

CACGCGTGTTATGAGTACAACCACATTTTCCCATTGCTGGAGAAGTACTG

TGGCTTTCACGAGGACAACATCCCTCAACTGGAGGATGTTTCACAGTTCC

TTCAGACTTGCACTGGTTTCCGCCTTCGACCTGTGGCTGGGCTGCTTAGC

TCACGGGACTTCCTGGGAGGCCTGGCCTTCAGAGTCTTTCACTGCACTCA

GTACATCCGGCATGGCTCTAAGCCAATGTACACCCCTGAACCGGATATAT

GCCACGAGCTGTTGGGACATGTGCCCCTGTTTTCTGATCGCAGCTTTGCC

CAGTTTTCCCAGGAGATTGGCCTGGCAAGTCTTGGTGCGCCTGATGAGTA

CATCGAGAAGCTCGCGACAATCTACTGGTTCACCGTGGAATTTGGACTCT

GCAAACAAGGGGACTCTATCAAAGCCTACGGAGCAGGACTCCTCTCCAGC

TTCGGTGAACTGCAGTATTGTCTGTCCGAGAAACCCAAACTCTTGCCCCT

GGAACTGGAAAAGACTGCCATCCAAAACTATACTGTCACGGAATTTCAGC

CACTGTATTATGTGGCTGAATCCTTTAACGATGCCAAGGAGAAGGTCCGT

AATTTTGCTGCCACAATACCACGCCCCTTCAGCGTGAGATACGACCCGTA

TACACAACGGATAGAGGTTCTGGACAACACCCAGCAACTGAAAATTCTGG

CAGACAGTATAAACAGCGAAATAGGGATCCTCTGTAGTGCCCTGCAGAAA

ATCAAATGA;

(SEQ ID NO: 3)
AGCCATGGACAGAATGTGGTCTGTCAGCTGTGAATCTGTTGATGGAGATC

CAACTATTTCTTTCATCAGAAAAAGTCCGAAAAGCAAACCTTAATTTGAA

ATAACAGCCTTAAATCCTTTACAAGATGGAGAAACAACAAATAAGTCAAA

ATAATCTGAAATGACAGGATATGAGTACATACTCAAGAGCATAATGGTAA

ATCTTTTGGGGTCATCTTTGATTTAGAGATGATAATCCCATACTCTCAAT

TGAGTTAAATCAGTAATCTGTCGCATTTCATCAAGATTAATTAAAATTTG

GGACCTGCTTCATTCAAGCTTCATATATGCTTTGCAGAGAACTCATAAAG

GAGCATATAAGGCTAAATGTAAAACCCAAGACTGTCATTAGAATTGAATT

ATTGGGCTTAATATAAATCGTAACCTATGAAGTTTATTTTTTATTTTAGT

TAACTATGATTCCAATTACTACTTTGTTATTGTACCTAAGTAAATTTTCT

TTAAGTCAGAAGCCCATTAAAATAGTTACAAGCATTGAACTTCTTTAGTA

TTATATTAATATAAAAACATTTTTGTATGTTTTATTGTAATCATAAATAC

TGCTGTATAAGGTAATAAAACTCTGCACCTAATCCCCATAACTTCCAGTA

TCATTTTCCAATTAATTATCAAGTCTGTTTTGGGAAACACTTTGAGGACA

TTTATGATGCAGCAGATGTTGACTAAAGGCTTGGTTGGTAGATATTCAGG

AAATGTTCACTGAATAAATAAGTAAATACATTATTGAAAAGCAAATCTGT

ATAAATGTGAAATTTTTATTTGTATTAGTAATAAAACATTAGTAGTTTAA

ACAAAAAAAAAAAAAAAAAAAAAAAAAAAAAACTCGACTCTAGATT;
or

-continued (SEQ ID NO: 4)
AGCCATGGACAGAATGTGGTCTGTCAGCTGTGAATCTGTTGATGGAGATC

CAACTATTTCTTTCATCAGAAAAAGTCCGAAAAGCAAACCTTAATTTGAA

ATAACAGCCTTAAATCCTTTACAAGATGGAGAAACAACAAATAAGTCAAA

ATAATCTGAAATGACAGGATATGAGTACATACTCAAGAGCATAATGGTAA

ATCTTTTGGGGTCATCTTTGATTTAGAGATGATAATCCCATACTCTCAAT

TGAGTTAAATCAGTAATCTGTCGCATTTCATCAAGATTA.

In embodiments, variants can be made to any of the above-described sequences. In embodiments, the PAH sequence or the variant thereof comprises (SEQ ID NO: 1), (SEQ ID NO: 2), (SEQ ID NO: 3), or (SEQ ID NO: 4).

In embodiments, the therapeutic cargo portion comprises at least one small RNA sequence that is capable of binding to at least one pre-determined complementary mRNA sequence. In embodiments, the at least one small RNA sequence targets a complementary mRNA sequence that contains a full-length UTR. In embodiments, the at least one small RNA sequence does not target a complementary mRNA sequence that contains a truncated UTR. In embodiments, the truncated UTR can include any of the truncated sequences identified herein or any variants thereof. In embodiments, the at least one pre-determined complementary mRNA sequence is a PAH mRNA sequence. In embodiments, the at least one small RNA sequence comprises a shRNA. In embodiments, the at least one small RNA sequence is under the control of a first promoter, and the PAH sequence or the variant thereof is under the control of a second promoter. In embodiments, the first promoter comprises a H1 promoter. In embodiments, the second promoter comprises a liver-specific promoter. In embodiments, the liver-specific promoter comprises a hAAT promoter. In embodiments, the at least one small RNA sequence comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with:

(SEQ ID NO: 5)
TCGCATTTCATCAAGATTAATCTCGAGATTAATCTTGATGAAATGCGATT

TTT;
or (SEQ ID NO: 6)
ACTCATAAAGGAGCATATAAGCTCGAGCTTATATGCTCCTTTATGAGTTT

TTT.

In embodiments, variants can be made of the above-described sequences. In embodiments, the at least one small RNA sequence comprises: (SEQ ID NO: 5), or (SEQ ID NO: 6). In embodiments, the viral vector is a lentiviral vector or an adeno-associated viral vector.

In another aspect, a lentiviral particle capable of infecting a target cell is disclosed. The lentiviral particle comprises an envelope protein optimized for infecting the target cell; and further comprises a viral vector as detailed herein. In embodiments, the target cell is a hepatic cell.

In another aspect, a method of treating PKU in a subject is disclosed. The method comprises administering to the subject a therapeutically effective amount of a lentiviral particle as detailed herein.

In another aspect, a method of preventing PKU in a subject is disclosed. The method comprises administering to the subject a therapeutically effective amount of the lentirviral particle as detailed herein. In embodiments, the therapeutically effective amount of the lentiviral particle comprises a plurality of single doses of the lentiviral particle. In embodiments, the therapeutically effective amount of the lentiviral particle comprises a single dose of the lentiviral particle. In embodiments, the method comprises administering to the subject therapeutically effective amounts of a first lentirviral particle and a second lentiviral particle comprising a viral vector. In embodiments, the first lentiviral particle comprises a PAH sequence or a variant thereof, and the second lentival particle comprises at least one small RNA sequence that is capable of binding to at least one pre-determined complementary mRNA sequence.

In another aspect, a method of treating or preventing PKU in a subject is disclosed. In embodiments, the subject is in utero. In embodiments, the method of treating or preventing PKU further comprises diagnosing a PKU genotype in the subject that correlates with a PKU phenotype. In embodiments, the method of treating or preventing PKU comprises diagnosis during prenatal screening of the subject. However, in embodiments, a subject may be diagnosed at any time prior to or after treatment.

Other aspects and advantages of the inventions described herein will become apparent from the following detailed description, taken in conjunction with the accompanying drawings, which illustrate by way of example the aspects of the inventions.

Phenylketonuria

PKU is believed to be caused by mutations of PAH and/or a defect in the synthesis or regeneration of PAH cofactors (i.e.; $BH_4$). Notably, several PAH mutations have been shown to affect protein folding in the endoplasmic reticulum resulting in accelerated degradation and/or aggregation due to missense mutations (63%) and small deletions (13%) in protein structure that attenuates or largely abolishes enzyme catalytic activity. As there are numerous mutations that can affect the functionality of PAH, an effective therapeutic approach for treating PKU may address the aberrant PAH and/or a mode by which replacement PAH can be administered.

In general, three major phenotypic groups are classified in PKU based on Phe levels measured at diagnosis, dietary tolerance to Phe and potential responsiveness to therapy. These groups include classical PKU (Phe>1200 µM), atypical or mild PKU (Phe is 600-1200 µM), and permanent mild hyperphenylalaninemia (HPA, Phe 120-600 µM).

Detection of PKU typically occurs during universal newborn screening (NBS). A drop of blood collected from a heel stick is tested for phenylalanine levels. NBS is mandatory in all 50 states of the USA.

Genetic Medicines

Genetic medicine includes reference to viral vectors that are used to deliver genetic constructs to host cells for the purposes of disease therapy or prevention.

Genetic constructs can include, but are not limited to, functional genes or portions of genes to correct or complement existing defects, DNA sequences encoding regulatory proteins, DNA sequences encoding regulatory RNA molecules including antisense, short homology RNA, long non-coding RNA, small interfering RNA or others, and decoy sequences encoding either RNA or proteins designed to compete for critical cellular factors to alter a disease state. Genetic medicine involves delivering these therapeutic genetic constructs to target cells to provide treatment or alleviation of a particular disease.

By delivering a functional PAH gene to the liver in vivo, its activity may be reconstituted, leading to normal clearance of Phe in the blood therefore eliminating the need for dietary restrictions or frequent enzyme replacement therapies. The effect of this therapeutic approach may be improved by the targeting of a shRNA against endogenous PAH. In an aspect of the disclosure, a functional PAH gene or a variant thereof can be delivered in utero if a fetus has been identified as being at risk of having a PKU genotype, especially in cases where the parental genotypes are known. Treatment may occur in vivo or in utero. In embodiments, the diagnostic step may be carried out to determine whether the fetus is at risk for a PKU phenotype. If the diagnostic step determines that the fetus is at risk for a PKU phenotype, then the fetus may be treated with the genetic medicines detailed herein.

Therapeutic Vectors

A lentiviral virion (particle) in accordance with various aspects and embodiments herein is expressed by a vector system encoding the necessary viral proteins to produce a virion (viral particle). In various embodiments, one vector containing a nucleic acid sequence encoding the lentiviral poi proteins is provided for reverse transcription and integration, operably linked to a promoter. In another embodiment, the pot proteins are expressed by multiple vectors. In other embodiments, vectors containing a nucleic acid sequence encoding the lentiviral Gag proteins for forming a viral capsid, operably linked to a promoter, are provided. In embodiments, this gag nucleic acid sequence is on a separate vector than at least some of the pol nucleic acid sequence. In other embodiments, the gag nucleic acid is on a separate vector from all the poi nucleic acid sequences that encode pol proteins.

Numerous modifications can be made to the vectors herein, which are used to create the particles, to further minimize the chance of obtaining wild type revertants. These include, but are not limited to deletions of the U3 region of the LTR, tat deletions and matrix (MA) deletions. In embodiments, the gag, poi and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell.

Lentiviral vector systems as provided herein typically include at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 1). In another embodiment, the gag and pol genes are provided on a first plasmid and the rev gene is provided on a second plasmid (e.g., FIG. 2). Accordingly, both 3-vector and 4-vector systems can be used to produce a lentivirus as described herein. In embodiments, the therapeutic vector, at least one envelope plasmid and at least one helper plasmid are transfected into a packaging cell, for example a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting of producing PAH and/or inhibiting the expression of endogenous PAH.

In another aspect, the lentiviral vector, which is also referred to herein as a therapeutic vector, includes the following elements: hybrid 5' long terminal repeat (RSV/5' LTR) (SEQ ID NOS: 7-8), Psi sequence (RNA packaging site) (SEQ ID NO: 9), RRE (Rev-response element) (SEQ ID NO: 10), cPPT (polypurine tract) (SEQ ID NO: 11), Anti alpha trypsin promoter (hAAT) (SEQ ID NO: 12), Phenylalanine hydroxylase (PAH) (SEQ ID NO: 1-4, Woodchuck Post-Transcriptional Regulatory Element (WPRE) (SEQ ID NOS: 13), and ΔU3 3' LTR (SEQ ID NO: 14). In embodiments, sequence variation, by way of substitution, deletion, another aspect, the lentiviral vector, which is also referred to herein as a therapeutic vector, includes the following elements: hybrid 5' long terminal repeat (RSV/5' LTR) (SEQ ID NOS: 7-8), Psi sequence (RNA packaging site) (SEQ ID NO: 9), RRE (Rev-response element) (SEQ ID NO: 10), cPPT (polypurine tract) (SEQ ID NO: 11), H1 promoter (SEQ ID NO: 15), PAH shRNA (SEQ ID NO: 1-4), Anti alpha trypsin promoter (hAAT) (SEQ ID NO: 12), PAH shRNA (SEQ ID NO: 1-4), Woodchuck Post-Transcriptional Regulatory Element (WPRE) (SEQ ID NOS: 13), and ΔU3 3' LTR (SEQ ID NO: 14). In embodiments, sequence variation, by way of substitution, deletion, addition, or mutation can be used to modify the sequences references herein.

In another aspect, a helper plasmid includes the following elements: CAG promoter (SEQ ID NO: 16); HIV component gag (SEQ ID NO: 17); HIV component pol (SEQ ID NO: 18); HIV Int (SEQ ID NO: 19); HIV RRE (SEQ ID NO: 20); and HIV Rev (SEQ ID NO: 21). In another aspect, the helper plasmid may be modified to include a first helper plasmid for expressing the gag and pol genes, and a second and separate plasmid for expressing the rev gene. In embodiments, sequence variation, by way of substitution, deletion, addition, or mutation can be used to modify the sequences references herein.

In another aspect, an envelope plasmid includes the following elements: RNA polymerase II promoter (CMV) (SEQ ID NO: 22) and vesicular stomatitis virus G glycoprotein (VSV-G) (SEQ ID NO: 23). In embodiments, sequence variation, by way of substitution, deletion, addition, or mutation can be used to modify the sequences references herein.

In various aspects, the plasmids used for lentiviral packaging are modified by substitution, addition, subtraction or mutation of various elements without loss of vector function. For example, and without limitation, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Various lentiviral packaging systems can be acquired commercially (e.g., *Lenti*-vpak packaging kit from OriGene Technologies, Inc., Rockville, MD), and can also be designed as described herein. Moreover, it is within the skill of a person ordinarily skilled in the art to substitute or modify aspects of a lentiviral packaging system to improve any number of relevant factors, including the production efficiency of a lentiviral particle.

In another aspect, adeno-associated viral (AAV) vectors can be used.

AAV Vector Construction.

PAH shRNA sequence #1 (SEQ ID NO: 5) or PAH shRNA sequence #2 (SEQ ID NO: 6) can be inserted into the pAAV plasmid (Cell Biolabs). PAH oligonucleotide sequences containing BamHI and EcoRI restriction sites can be synthesized by Eurofins MWG Operon. Overlapping sense and antisense oligonucleotide sequences can be mixed and annealed during cooling from 70 degrees Celsius to room temperature. The pAAV can be digested with the restriction enzymes BamHI and EcoRI for one hour at 37 degrees Celsius. The digested pAAV plasmid can be purified by agarose gel electrophoresis and extracted from the gel using a DNA gel extraction kit from Thermo Scientific. The DNA concentrations can be determined and vector to oligo (3:1 ratio) can be mixed, allowed to anneal, and ligated. The ligation reaction can be performed with T4 DNA ligase for 30 minutes at room temperature. 2.5 microliters of the ligation mix can be added to 25 microliters of STBL3 competent bacterial cells. Transformation can be achieved after heat-shock at 42 degrees Celsius. Bacterial cells can be spread on agar plates containing ampicillin and drug-resistant colonies (indicating the presence of ampicillin-resistance plasmids) can be recovered and expanded in LB broth. To check for insertion of the oligo sequences, plasmid DNA can be extracted from harvested bacteria cultures with the Thermo Scientific DNA mini prep kit. Insertion of shRNA sequences in the pAAV plasmid can be verified by DNA sequencing using a specific primer for the promoter used to regulate shRNA expression.

Figure 3:
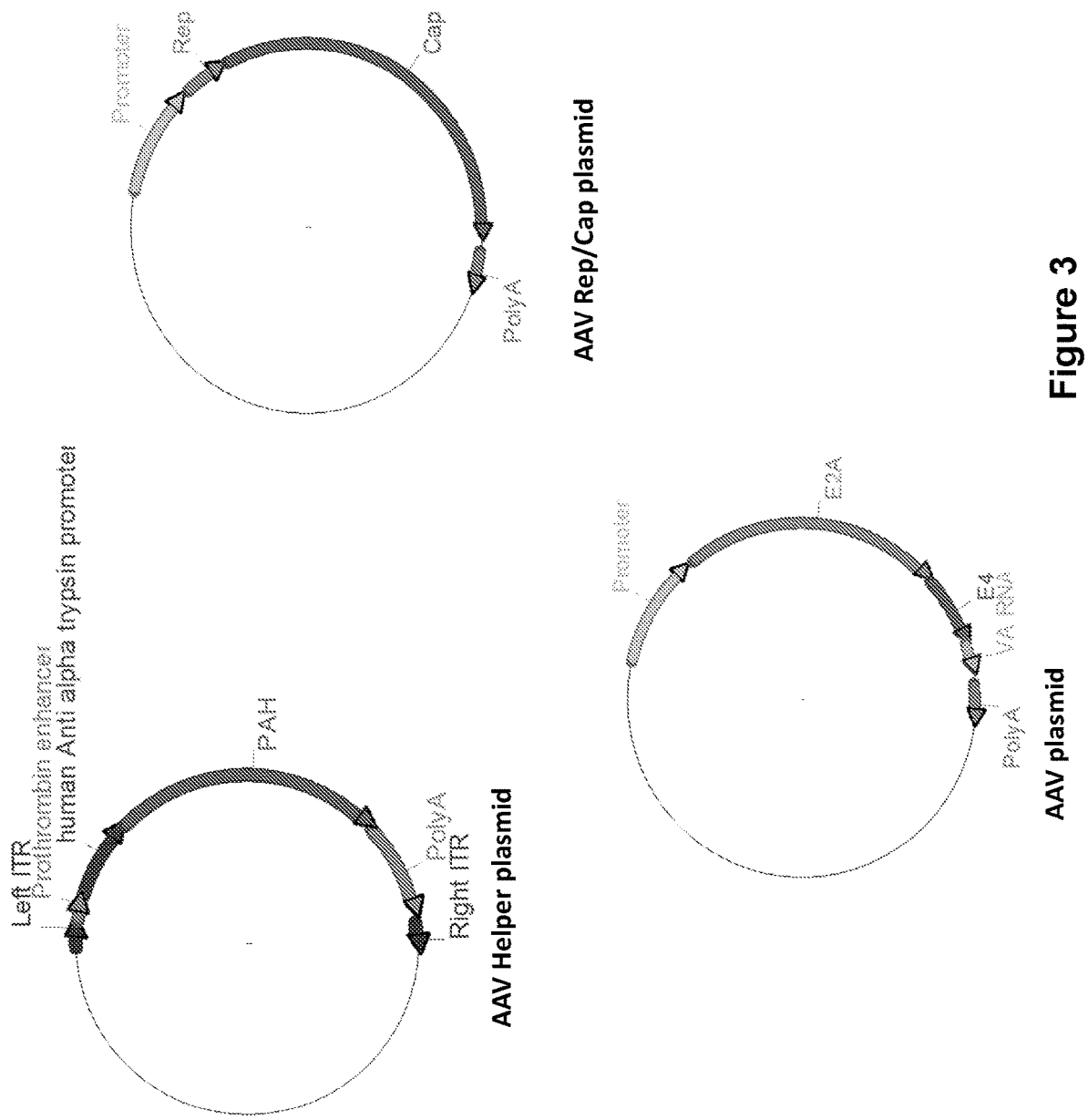
FIG. 3 depicts an exemplary 3-vector adeno-associated viral vector system in a circularized form.

An exemplary AAV plasmid system for expressing PAH (SEQ ID NO: 1) is depicted in FIG. 3. Briefly, the leftmost AAV Helper plasmid contains a Left ITR (SEQ ID NO: 47), a Prothrombin enhancer (SEQ ID NO: 48), a human Anti alpha trypsin promoter (SEQ ID NO: 12), a PAH element (SEQ ID NO: 1), a PolyA element (SEQ ID NO: 49), and a Right ITR (SEQ ID NO: 50). The AAV plasmid depicted in the middle of FIG. 3 shows an AAV plasmid that contains a suitable promoter element (SEQ ID NO: 16; SEQ ID NO: 22), and E2A element (SEQ ID NO: 51), an E4 element (SEQ ID NO: 52), a VA RNA element (SEQ ID NO: 53), and a PolyA element (SEQ ID NO: 49). The rightmost plasmid depicts an AAV Rep/Cap plasmid that contains a suitable promoter element, a Rep element (SEQ ID NO: 54), a Cap element (SEQ ID NO: 55), and a PolyA element (SEQ ID NO: 49).

Production of AAV Particles.

The AAV-PAH shRNA plasmid may be combined with the plasmids pAAV-RC2 (Cell Biolabs) and pHelper (Cell Biolabs). The pAAV-RC2 plasmid may contain the Rep and AAV2 capsid genes and pHelper may contain the adenovirus E2A, E4, and VA genes. To produce AAV particles, these plasmids may be transfected in the ratio 1:1:1 (pAAV-shPAH: pAAV-RC2: pHelper) into 293T cells. For transfection of cells in 150 mm dishes (BD Falcon), 10 micrograms of each plasmid may be added together in 1 ml of DMEM. In another tube, 60 microliters of the transfection reagent PEI (1 microgram/ml) (Polysciences) may be added to 1 ml of DMEM. The two tubes may be mixed together and allowed to incubate for 15 minutes. Then the transfection mixture may be added to cells and the cells may be collected after 3 days. The cells may be lysed by freeze/thaw lysis in dry ice/isopropanol. Benzonase nuclease (Sigma) may be added to the cell lysate for 30 minutes at 37 degrees Celsius. Cell debris may then be pelleted by centrifugation at 4 degrees Celsius for 15 minutes at 12,000 rpm. The supernatant may be collected and then added to target cells.

Dosage and Dosage Forms

The disclosed vector compositions allow for short, medium, or long-term expression of genes or sequences of interest and episomal maintenance of the disclosed vectors. Accordingly, dosing regimens may vary based upon the condition being treated and the method of administration.

In embodiments, vector compositions may be administered to a subject in need in varying doses. Specifically, a subject may be administered about $\geq 10^6$ infectious doses (where 1 dose is needed on average to transduce 1 target cell). More specifically, a subject may be administered about $\geq 10^7$, about $\geq 10^8$, about $\geq 10^9$, or about $\geq 10^{10}$ infectious doses, or any number of doses in-between these values. Upper limits of dosing will be determined for each disease indication, including a specific cancer type, and will depend on toxicity/safety profiles for each individual product or product lot.

Additionally, vector compositions of the present disclosure may be administered periodically, such as once or twice a day, or any other suitable time period. For example, vector compositions may be administered to a subject in need once a week, once every other week, once every three weeks, once a month, every other month, every three months, every six months, every nine months, once a year, every eighteen months, every two years, every thirty months, or every three years.

In embodiments, the disclosed vector compositions are administered as a pharmaceutical composition. In embodiments, the pharmaceutical composition can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition can also be formulated for injection, insufflation, infusion, or intradermal exposure. For instance, an injectable formulation may comprise the disclosed vectors in an aqueous or non-aqueous solution at a suitable pH and tonicity.

The disclosed vector compositions may be administered to a subject via direct injection into a tumor site or at a site of infection. In some embodiments, the vectors can be administered systemically. In some embodiments, the vector compositions can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the pharmaceutical composition may be a controlled release formulation, sustained release formulation, immediate release formulation, or any combination thereof. Further, the pharmaceutical composition may be a transdermal delivery system.

In embodiments, the pharmaceutical composition can be formulated in a solid dosage form for oral administration, and the solid dosage form can be powders, granules, capsules, tablets or pills. In embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In embodiments, the pharmaceutical compositions can be formulated as sublingual or buccal dosage forms. Such dosage forms comprise sublingual tablets or solution compositions that are administered under the tongue and buccal tablets that are placed between the cheek and gum.

In embodiments, the pharmaceutical compositions can be formulated as nasal dosage forms. Such dosage forms of the present invention comprise solution, suspension, and gel compositions for nasal delivery.

In embodiments, the pharmaceutical compositions can be formulated in liquid dosage forms for oral administration, such as suspensions, emulsions or syrups. In embodiments, the liquid dosage forms can include, in addition to commonly used simple diluents such as water and liquid paraffin, various excipients such as humectants, sweeteners, aromatics or preservatives. In embodiments, the compositions can be formulated to be suitable for administration to a pediatric patient.

In embodiments, the pharmaceutical compositions can be formulated in dosage forms for parenteral administration, such as sterile aqueous solutions, suspensions, emulsions, non-aqueous solutions or suppositories. In embodiments, the solutions or suspensions can include propylene glycol, polyethylene glycol, vegetable oils such as olive oil or injectable esters such as ethyl oleate.

The dosage of the pharmaceutical compositions can vary depending on the patient's weight, age, gender, administration time and mode, excretion rate, and the severity of disease.

In embodiments, the vector compositions are administered into the cerebrospinal fluid, blood or lymphatic circulation by venous or arterial cannulation or injection, intradermal delivery, intramuscular delivery or injection into a draining organ near the site of disease.

The following examples are given to illustrate aspects of the present invention. It should be understood, however, that the invention is not to be limited to the specific conditions or details described in these examples. All printed publications referenced herein are specifically incorporated by reference.

EXAMPLES

Example 1: Development of a Lentiviral Vector System

A lentiviral vector system was developed as summarized in FIG. 1 (circularized form). Lentiviral particles were produced in 293T/17 HEK cells (purchased from American Type Culture Collection, Manassas, VA) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), by measuring the number of viral DNA copies per transduced cell by quantitative PCR, or by infecting cells and using light (if the vectors encode luciferase or fluorescent protein markers).

As mentioned above, a 3-vector system (i.e., which includes a 2-vector lentiviral packaging system) was designed for the production of lentiviral particles. A schematic of the 3-vector system is shown in FIG. 1. Briefly, and with reference to FIG. 1, the top-most vector is a helper plasmid, which, in this case, includes Rev. The vector appearing in the middle of FIG. 1 is the envelope plasmid. The bottom-most vector is the therapeutic vector, as described herein.

Referring to FIG. 1, the Helper plus Rev plasmid includes a CAG enhancer (SEQ ID NO: 24); a CAG promoter (SEQ ID NO: 16); a chicken beta actin intron (SEQ ID NO: 25); a HIV gag (SEQ ID NO: 17); a HIV Pol (SEQ ID NO: 18); a HIV Int (SEQ ID NO: 19); a HIV RRE (SEQ ID NO: 20); a HIV Rev (SEQ ID NO: 21); and a rabbit beta globin poly A (SEQ ID NO: 26).

The Envelope plasmid includes a CMV promoter (SEQ ID NO: 22); a beta globin intron (SEQ ID NO: 27); a VSV-G envelope glycoprotein (SEQ ID NO: 23); and a rabbit beta globin poly A (SEQ ID NO: 26).

Synthesis of a 3-vector system, which includes a 2-vector lentiviral packaging system, consisting of Helper (plus Rev) and Envelope plasmids, is disclosed.

Materials and Methods:

Construction of the Helper Plasmid:

The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAAT-TCATGAATTTGCCAGGAAGAT-3') (SEQ ID NO: 28) and reverse primer was (5'-CCATACAAT-GAATGGACACTAGGCGGCCGCACGAAT-3') (SEQ ID NO: 29).

The sequence for the Gag, Pol, Integrase fragment was as follows:

```
                                           (SEQ ID NO: 30)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC

CATTAGTCCTATTGAGACTGTACCAGTAAAATTAAAGCCAGGAATGGATG

GCCCAAAAGTTAAACAATGGCCATTGACAGAAGAAAAAATAAAAGCATTA

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTTCAG

TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGGCAA

GGCCAATGGACATATCAAATTTATCAAGAGCCATTTAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGGCGGGGATCAAGCAGGAATTTGGCAT

TCCCTACAATCCCCAAAGTCAAGGAGTAATAGAATCTATGAATAAAGAAT

TAAAGAAAATTATAGGACAGGTAAGAGATCAGGCTGAACATCTTAAGACA

GCAGTACAAATGGCAGTATTCATCCACAATTTTAAAAGAAAAGGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG

GTTTATTACAGGGACAGCAGAGATCCAGTTTGGAAAGGACCAGCAAAGCT

CCTCTGGAAAGGTGAAGGGGCAGTAGTAATACAAGATAATAGTGACATAA

AAGTAGTGCCAAGAAGAAAAGCAAAGATCATCAGGGATTATGGAAAACAG

ATGGCAGGTGATGATTGTGTGGCAAGTAGACAGGATGAGGATTAA
```

Next, a DNA fragment containing the Rev, RRE, and rabbit beta globin poly A sequence with XbaI and XmaI flanking restriction sites was synthesized by Eurofins Genomics. The DNA fragment was then inserted into the plasmid at the XbaI and XmaI restriction sites The DNA sequence was as follows:

```
                                           (SEQ ID NO: 31)
TCTAGAATGGCAGGAAGAAGCGGAGACAGCGACGAAGAGCTCATCAGAAC

AGTCAGACTCATCAAGCTTCTCTATCAAAGCAACCCACCTCCCAATCCCG

AGGGGACCCGACAGGCCCGAAGGAATAGAAGAAGAAGGTGGAGAGAGAGA

CAGAGACAGATCCATTCGATTAGTGAACGGATCCTTGGCACTTATCTGGG

ACGATCTGCGGAGCCTGTGCCTCTTCAGCTACCACCGCTTGAGAGACTTA

CTCTTGATTGTAACGAGGATTGTGGAACTTCTGGGACGCAGGGGGTGGGA

AGCCCTCAAATATTGGTGGAATCTCCTACAATATTGGAGTCAGGAGCTAA
```

-continued
```
AGAATAGAGGAGCTTTGTTCCTTGGGTTCTTGGGAGCAGCAGGAAGCACT

ATGGGCGCAGCGTCAATGACGCTGACGGTACAGGCCAGACAATTATTGTC

TGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTATATTTTGTTTTGTGTTATTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCAGCGGCCGCCCCGGG
```

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by Eurofins Genomics. The DNA fragment was then inserted into the plasmid at the MluI and EcoRI restriction sites. The DNA sequence was as follows:

```
                                        (SEQ ID NO: 32)
ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT
```

-continued
```
TTTAATTATTTTGTGCAGCGATGGGGGCGGGGGGGGGGGGGCGCGCGCC

AGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGAGCGGCTCGGGGGGTGCGTGCGTGTGTGTGCGT

GGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGC

CGGGGGCGGTGCCCCGCGGTGCGGGGGGGCTGCGAGGGGAACAAAGGCTG

CGTGCGGGGTGTGTGCGTGGGGGGGTGAGCAGGGGGTGTGGGCGCGGCGG

TCGGGCTGTAACCCCCCCCTGCACCCCCCTCCCCGAGTTGCTGAGCACGG

CCCGGCTTCGGGTGCGGGGCTCCGTGCGGGGCGTGGCGCGGGGCTCGCCG

TGCCGGGCGGGGGTGGCGGCAGGTGGGGGTGCCGGGCGGGGCGGGGCCG

CCTCGGGCCGGGGAGGGCTCGGGGGAGGGGCGCGGCGGCCCCGGAGCGCC

GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTG

CGGCGCCGGCAGGAAGGAAATGGGCGGGAGGGCCTTCGTGCGTCGCCGC

GCCGCCGTCCCCTTCTCCATCTCCAGCCTCGGGGCTGCCGCAGGGGACG

GCTGCCTTCGGGGGGACGGGGCAGGGCGGGGTTCGGCTTCTGGCGTGTG

ACCGGCGGGAATTC
```

Construction of the VSV-G Envelope plasmid:

The vesicular stomatitis Indiana virus glycoprotein (VSV-G) sequence was synthesized by Eurofins Genomics with flanking EcoRI restriction sites. The DNA fragment was then inserted into the pCDNA3.1 plasmid (Invitrogen) at the EcoRI restriction site and the correct orientation was determined by sequencing using a CMV specific primer.

The DNA sequence was as follows:

```
                                        (SEQ ID NO: 23)
GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT
```

-continued
CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

AACTTCCTGATGATGAGAGTTTATTTTTTGGTGATACTGGGCTATCCAAA

AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC

TCCGAGTTGGTATCCATCTTTGCATTAAATTAAAGCACACCAAGAAAAGA

CAGATTTATACAGACATAGAGATGAGAATTC

Figure 2:
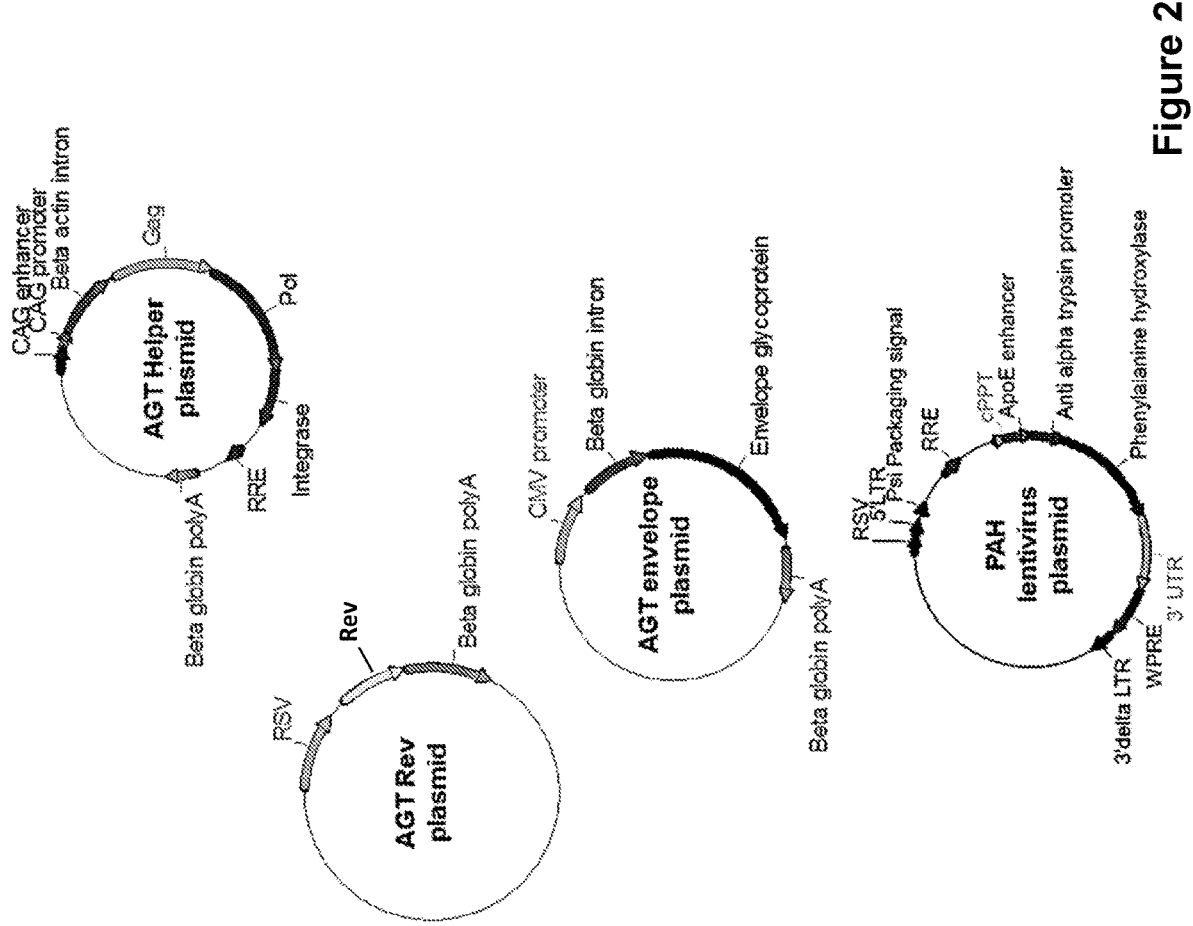
FIG. 2 depicts an exemplary 4-vector lentiviral vector system in a circularized form.

A 4-vector system, which includes a 3-vector lentiviral packaging system, has also been designed and produced using the methods and materials described herein. A schematic of the 4-vector system is shown in FIG. 2. Briefly, and with reference to FIG. 2, the top-most vector is a helper plasmid, which, in this case, does not include Rev. The vector second from the top is a separate Rev plasmid. The vector second from the bottom is the envelope plasmid. The bottom-most vector is the therapeutic vector as described herein.

Referring to FIG. 2, the Helper plasmid includes a CAG enhancer (SEQ ID NO: 24); a CAG promoter (SEQ ID NO: 16); a chicken beta actin intron (SEQ ID NO: 25); a HIV gag (SEQ ID NO: 17); a HIV Pol (SEQ ID NO: 18); a HIV Int (SEQ ID NO: 19); a HIV RRE (SEQ ID NO: 20); and a rabbit beta globin poly A (SEQ ID NO: 26).

The Rev plasmid includes a RSV promoter (SEQ ID NO: 7); a HIV Rev (SEQ ID NO: 21); and a rabbit beta globin poly A (SEQ ID NO: 26).

The Envelope plasmid includes a CMV promoter (SEQ ID NO: 22); a beta globin intron (SEQ ID NO: 27); a VSV-G (SEQ ID NO: 23); and a rabbit beta globin poly A (SEQ ID NO: 26).

In one aspect, the therapeutic PAH lentivirus plasmid includes all of the elements shown in FIG. 4A. In another aspect, the therapeutic PAH lentivirus plasmid includes all of the elements shown in FIG. 4B.

Synthesis of a 4-vector system, which includes a 3-vector lentiviral packaging system consisting of Helper, Rev, and Envelope plasmids, is disclosed.

Materials and Methods:

Construction of the Helper Plasmid without Rev:

The Helper plasmid without Rev was constructed by inserting a DNA fragment containing the RRE and rabbit beta globin poly A sequence. This sequence was synthesized by Eurofins Genomics with flanking XbaI and XmaI restriction sites. The RRE/rabbit poly A beta globin sequence was then inserted into the Helper plasmid at the XbaI and XmaI restriction sites.

The DNA sequence is as follows:

(SEQ ID NO: 56)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTTATATTTTGTTTTGTGTTATTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA

AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG

Construction of the Rev Plasmid:

The RSV promoter and HIV Rev sequences were synthesized as a single DNA fragment by Eurofins Genomics with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

(SEQ ID NO: 33)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

-continued

```
AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGAGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA
```

The plasmids used in the packaging systems can be modified with similar elements, and the intron sequences can potentially be removed without loss of vector function. For example, the following elements can replace similar elements in the packaging system:

Promoters: Elongation Factor-1 (EF-1) (SEQ ID NO: 34), phosphoglycerate kinase (PGK) (SEQ ID NO: 35), and ubiquitin C (UbC) (SEQ ID NO: 36) can replace the CMV (SEQ ID NO: 22) or CAG promoter (SEQ ID NO: 16). These sequences can also be further varied by addition, substitution, deletion or mutation.

Poly A sequences: SV40 poly A (SEQ ID NO: 37) and bGH poly A (SEQ ID NO: 38) can replace the rabbit beta globin poly A (SEQ ID NO: 26). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 17); HIV Pol (SEQ ID NO: 18); and HIV Int (SEQ ID NO: 19) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 39), gibbon ape leukemia virus (GALV) (SEQ ID NO: 40), Rabies (FUG) (SEQ ID NO: 41), lymphocytic choriomeningitis virus (LCMV) (SEQ ID NO: 42), influenza A fowl plague virus (FPV) (SEQ ID NO: 43), Ross River alphavirus (RRV) (SEQ ID NO: 44), murine leukemia virus 10A1 (MLV) (SEQ ID NO: 45), or Ebola virus (EboV) (SEQ ID NO: 46). Sequences for these envelopes are identified in the sequence portion herein. Further, these sequences can also be further varied by addition, substitution, deletion or mutation.

In summary, the 3-vector versus 4-vector systems can be compared and contrasted as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, RRE, cPPT, ApoE Enhancer, anti-alpha trypsin promoter, phenylalanine hydroxylase, 3' UTR, WPRE, and 3'delta LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, RRE, cPPT, ApoE Enhancer, anti-alpha trypsin promoter, phenylalanine hydroxylase, WPRE, and 3'delta LTR. Sequences corresponding with the above elements are identified in the sequence listings portion herein.

Example 2. Therapeutic Vectors

Figure 4:
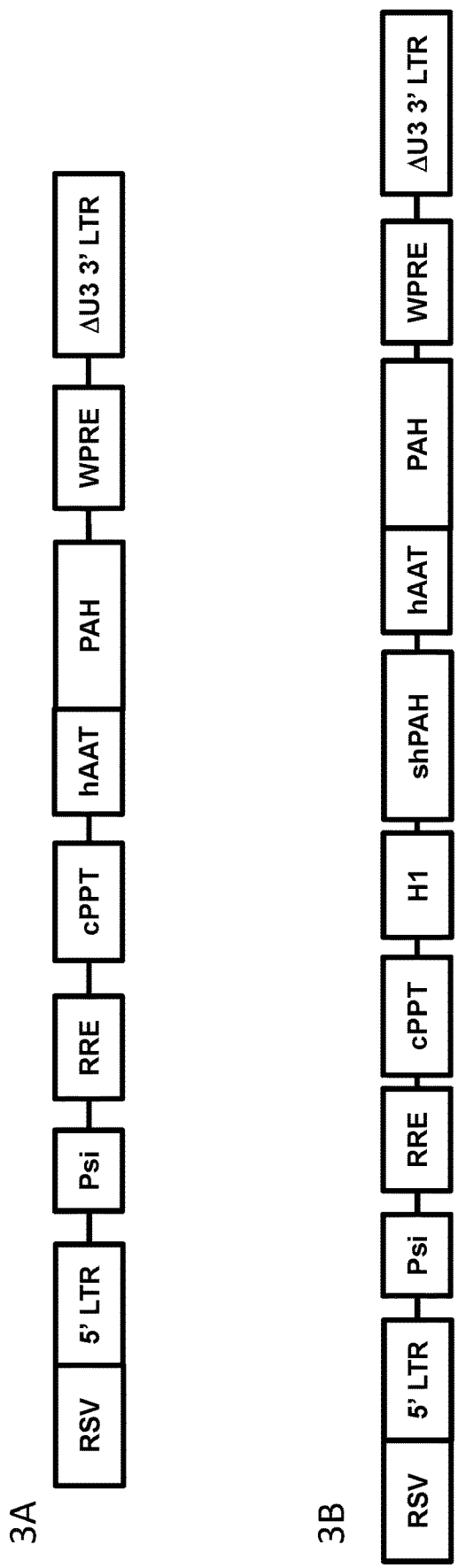
FIG. 4 depicts: (A) a linear map of a lentiviral vector expressing PAH; and (B) a linear map of a lentiviral vector expressing a PAH shRNA sequence and a PAH sequence.

Exemplary therapeutic vectors have been designed and developed as shown, for example, in FIG. 4.

Referring first to FIG. 4A, from left to right, the key genetic elements are as follows: hybrid 5' long terminal repeat (RSV/LTR), Psi sequence (RNA packaging site), RRE (Rev-response element), cPPT (polypurine tract), a hAAT promoter, a PAH or variant thereof, as detailed herein, Woodchuck Post-Transcriptional Regulatory Element (WPRE), and LTR with a deletion in the U3 region.

Referring next to FIG. 4B, from left to right, the key genetic elements are as follows: hybrid 5' long terminal repeat (RSV/LTR), Psi sequence (RNA packaging site), RRE (Rev-response element), cPPT (polypurine tract), an H1 promoter, a PAH shRNA sequence or variant thereof, as detailed herein, a hAAT promoter, a PAH sequence including the PAH sequences and variants thereof, as detailed herein, a Woodchuck Post-Transcriptional Regulatory Element (WPRE), and LTR with a deletion in the U3 region.

To produce the vectors outlined generally in FIGS. 4A and 4B, the following methods and materials were employed.

Inhibitory RNA Design:

The sequence of Homo sapiens phenylalanine hydroxylase (PAH) (NM_000277.1) mRNA was used to search for potential shRNA candidates to knockdown PAH levels in human cells. Potential RNA shRNA sequences were chosen from candidates selected by siRNA or shRNA design programs such as from the GPP Web Portal hosted by the Broad Institute (http://portals.broadinstitute.org/gpp/public/) or the BLOCK-iT RNAi Designer from Thermo Scientific (https://rnaidesigner.thermofisher.com/rnaiexpress/). Individual selected shRNA sequences were inserted into a lentiviral vector immediately 3 prime to a RNA polymerase III promoter H1 (SEQ ID NO: 15) to regulate shRNA expression. These lentivirus shRNA constructs were used to transduce cells and measure the change in specific mRNA levels.

Vector Construction:

For PAH shRNA, oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knock-down PAH.

```
PAH shRNA sequence #1:
                                       (SEQ ID NO: 5)
TCGCATTTCATCAAGATTAATCTCGAGATTAATCTTGATGAAATGCGATT

TTT

PAH shRNA sequence #2:
                                       (SEQ ID NO: 6)
ACTCATAAAGGAGCATATAAGCTCGAGCTTATATGCTCCTTTATGAGTTT

TTT
```

Example 3—Phenylalanine Hydroxylase Open Reading Frame Including Complete 5' and 3' UTR Hepa1-6 mouse hepatoma cells were infected with lentiviral vectors containing the PAH gene (SEQ ID NO: 1), including its full 5 prime untranslated region and its full 3 prime untranslated region (SEQ ID NO: 3) as shown in FIG. 5. FIG. 5 provides the complete DNA sequence of a cDNA expression construct for human PAH (SEQ ID NO: 57). This version includes the intact 5' UTR region (shown in boldface), the coding region for hPAH, and the complete 3' UTR (shown in boldface). Results for these infections are detailed in further Examples herein.

Example 4—Phenylalanine Hydroxylase Open Reading Frame Including Complete 5' UTR and a Truncated 3' UTR Hepa1-6 mouse hepatoma cells were infected with lentiviral vectors containing the PAH gene (SEQ ID NO: 1), including its full 5 prime untranslated region and a truncated 3 prime untranslated region (SEQ ID NO: 4) as shown in FIG. 6. FIG. 6 provides the cDNA sequence for human PAH that includes the 5' UTR (897 nucleotides) (shown in boldface), the coding region for hPAH, and the truncated 3' UTR (289 nucleotides) (shown in boldface) (SEQ ID NO: 58).

Example 5. Materials and Methods for PAH

The sequence of *Homo sapiens* phenylalanine hydroxylase (hPAH) mRNA (Gen Bank: NM_000277.1) was chemically synthesized with EcoRI and SalI restriction enzyme sites located at distal and proximal ends of the gene. hPAH treated with EcoRI and SalI restriction enzymes was excised and ligated into pCDH plasmids under control of a hybrid promoter comprising parts of ApoE (NM_000001.11, U35114.1) and hAAT (HG98385.1) locus control regions. Similarly, the mouse PAH gene (mPAH) (NM_008777.3) was synthesized and inserted into pCDH under control of the same hybrid promoter. Additionally, human PAH was synthesized to include the 3' untranslated region (UTR).

In a further modification, the naturally occurring UTR was truncated to improve expression of the hPAH gene when controlled by liver-specific promoter hAAT. Oligonucleotide sequences containing hPAH, hPAH with full-length UTR, hPAH with truncated UTR or mPAH alone with BamHI and EcoRI restriction sites were synthesized by Eurofins Genomics. Oligonucleotide sequences were annealed by incubation at 70 degrees Celsius and cooling to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentration was determined then mixed with the synthetic oligonucleotides (hPAH or mPAH) using a vector to oligo sequence ratio of 3:1 insert to vector. The mixture was ligated T4 DNA ligase for 30 minutes at room temperature. 2.5 microliters of the ligation mix was added to 25 microliters of STBL3 competent bacterial cells. Transformation was carried out by heat-shock at 42 degrees Celsius. Bacterial cells were streaked onto agar plates containing ampicillin and then colonies were expanded in LB broth. To check for insertion of the oligo sequences, Plasmid DNA was extracted from harvested bacteria cultures with the Invitrogen DNA mini prep kit. Insertion of the shRNA sequence in the lentiviral vector (LV) was verified by DNA sequencing using a primer complementary to the promoter used for shRNA expression. The lentiviral vectors containing a verified hPAH or mPAH sequence were then used to package lentiviral particles to test for their ability to express PAH. Mammalian cells were transduced with lentiviral particles. Cells were collected after 2-4 days and protein was analyzed by western blot for PAH expression.

Modifications of the hPAH Sequence:

Several modifications of the hPAH sequence were incorporated to improve cellular expression levels. First, normal hPAH 3' untranslated region (UTR) was inserted after the PAH coding region and before the mRNA terminus. This created LV-hAAT-hPAH-UTR. Levels of hPAH expression were increased by adding the 3' UTR but did not reach the levels of mPAH expressed in a similar vector.

Next, the hPAH UTR region was modified to improve expression levels under the control of a liver-specific promoter. A portion of the untranslated region approximately equal to the distal half of the sequence was removed. This modification increased expression of LV-hAAT-hPAH-UTR up to levels similar to what was achieved for mPAH expression. Surprisingly, truncation of the UTR was only required for high-level expression when using the liver-specific hAAT promoter. Generating hPAH expression constructs under the control of the CMV immediate early promoter gave high-level expression irrespective of the presence or absence of UTR and irrespective of whether or not the UTR was truncated. This important advance in understanding the structure function for the hPAH gene locus allows us to generate constructs for specific expression in liver tissue while still achieving high-level production of hPAH. Restricting transgene expression to liver cells is an important consideration for vector safety and target specificity in a genetic medicine for phenylketonuria.

Figure 7:
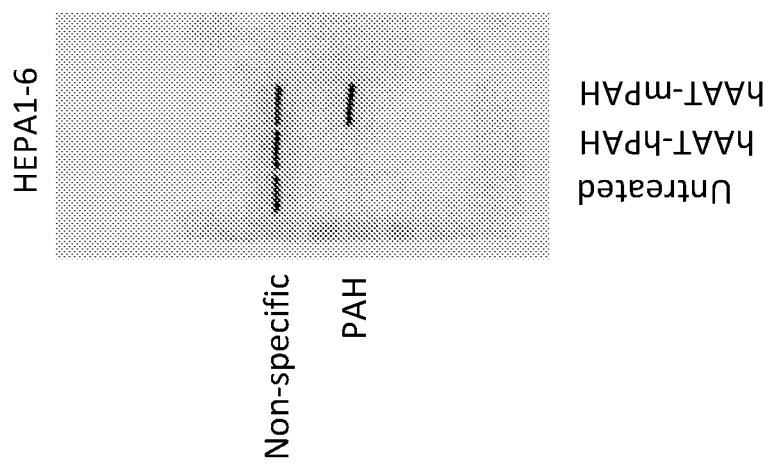
FIG. 7 depicts immunoblot data comparing levels of expression for human and mouse PAH genes.

Example 6. Immunoblot Analysis Comparing Levels of Expression for Human and Mouse PAH Genes An immunoblot analysis comparing levels of expression for human and mouse PAH genes was conducted as summarized in FIG. 7. This Example illustrates that expression of mouse PAH in Hepa1-6 mouse liver cancer cells (Hepa1-6) is higher compared to the nearly undetectable expression of human PAH in Hepa1-6.

Human and mouse PAH were synthesized and inserted into lentiviral vectors. Insertion of the sequences was then verified by DNA sequencing. The lentiviral vectors containing a correct hPAH or mPAH sequence were then used to transduce Hepa1-6 mouse liver cancer cells (purchased from American Type Culture Collection, Manassas, VA). Cells were collected after 2-4 days and protein was analyzed by western blot for PAH expression. Hepa1-6 cells were infected with lentiviral particles containing green fluorescent protein (GFP) as a marker for transduction efficiency. The relative expression of human or mouse PAH was detected by immunoblot using an anti-PAH antibody (Abcam).

Figure 8:
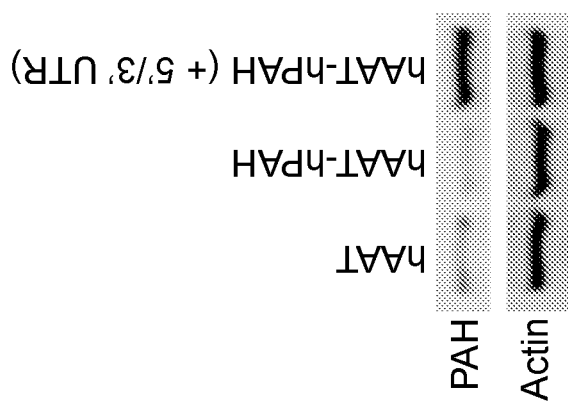
FIG. 8 depicts data demonstrating lentivirus-delivered expression of hPAH with or without the 3' UTR region in Hepa1-6 cells.

Example 7. Lentivirus-Delivered Expression of hPAH with or without the 3' UTR Region in Hepa1-6 Cells This Example illustrates that expression of PAH is substantially increased in Hepa1-6 carcinoma cells when a lentiviral vector expresses hPAH including both the 5' UTR and 3' UTR, as shown in FIG. 8. This Example also illustrates that a lentivirus vector expressing only the coding region for hPAH does not increase the levels of PAH protein in Hepa1-6 cells.

Human PAH was synthesized and inserted into lentiviral vectors. Insertion of the sequences was verified by DNA sequencing. The lentiviral vectors containing a verified hPAH sequence were then used to transduce Hepa1-6 mouse liver cancer cells (purchased from American Type Culture Collection, Manassas, VA). The lentiviral vectors incorporated a human PAH gene with or without its 3' UTR. In addition, hPAH expression in these constructs was driven by the hAAT promoter. Cells were transduced with lentiviral particles and after 2-4 days protein was analyzed by western blot for PAH expression. Hepa1-6 cells were infected with lentiviral particles containing green fluorescent protein (GFP) as a marker for transduction efficiency. The relative expression of human PAH was detected by immunoblot using an anti-PAH antibody (Abcam).

As shown in FIG. 8, three groups are compared: a control comprising Hepa1-6 cells alone (lane 1), a group expressing a lentivirus vector expressing only the coding region for hPAH (lane 2), and a lentivirus vector expressing hPAH and including both the 5' and 3' UTR regions (lane 3). Notably, Hepa1-6 carcinoma cells are derived from mouse liver tissue and thus there is a natural background expression of PAH observed in Lane 1 (labeled hAAT). FIG. 8 demonstrates that expression of PAH is substantially increased in Hepa1-6 carcinoma cells when a lentivirus (LV) expressing PAH shRNA includes both the 5' UTR and 3' UTR.

Example 8. Lentiviral Vector Expressing hPAH with a Truncated 3' UTR in Hepa1-6 Cells This Example illustrates that a lentiviral vector expressing hPAH with a truncated 3' UTR (hPAH-3'UTR) demonstrates substantially increased expression of hPAH compared to constructs containing a full-length 3'UTR sequence, as shown in FIG. 9.

Human PAH was synthesized and inserted into lentiviral vectors. Insertion of the sequences was verified by DNA sequencing. The lentiviral vectors containing a verified hPAH sequence were then used to transduce Hepa1-6 liver cancer cells (purchased from American Type Culture Collection, Manassas, VA). The lentiviral vectors incorporated a human PAH gene with or without its 3' UTR. In addition, hPAH expression in these constructs was driven by the hAAT promoter. Cells were transduced with lentiviral particles and after 2-4 days protein was analyzed by western blot for PAH expression. Hepa1-6 cells were infected with lentiviral particles containing green fluorescent protein (GFP) as a marker for transduction efficiency. The relative expression of human PAH was detected by immunoblot using an anti-PAH antibody (Abcam) and the loading control Beta-actin.

Figure 9:
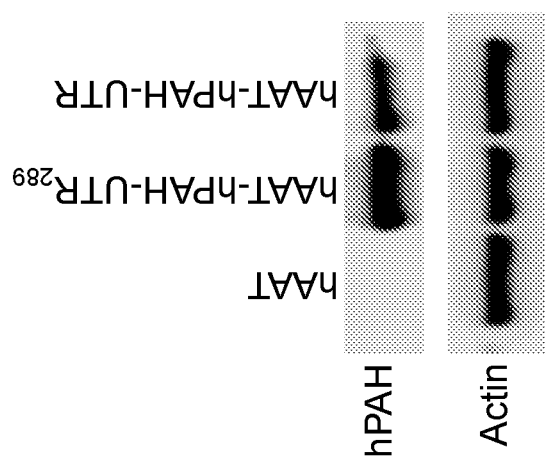
FIG. 9 depicts results of a lentiviral vector expressing hPAH with a truncated 3' UTR in Hepa1-6 cells.

FIG. 9 shows expression of hPAH constructs in Hepa1-6 carcinoma cells. As shown in FIG. 9, three groups are compared: a control lentiviral vector expressing only the coding region for hPAH (lane 1), a construct containing hPAH-3'UTR (lane 2), and a full-length hPAH 3'UTR sequence (lane 3). Notably, Hepa1-6 carcinoma cells are derived from human liver tissue and thus there is a natural background expression of PAH observed in Lane 1 (labeled hAAT). This Example illustrates that hPAH-3'UTR increases hPAH expression relative to the wild type 3'UTR sequence in Hepa1-6 cells.

Figure 10:
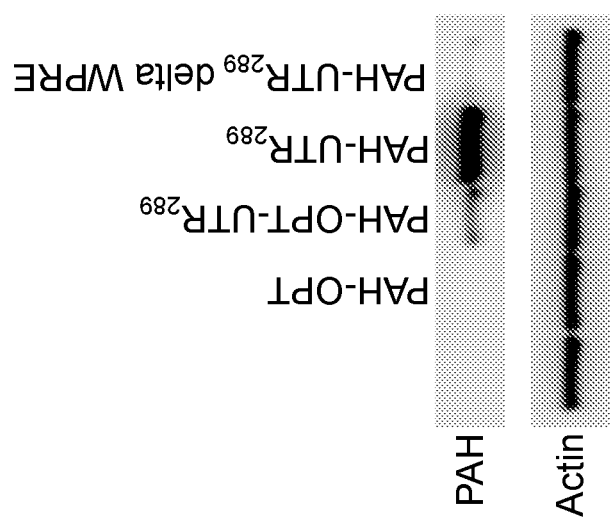
FIG. 10 depicts data demonstrating expression of codon-optimized hPAH with or without WPRE in mouse Hepa1-6 cells.

Example 9. Expression of Codon-Optimized hPAH with or without WPRE in Mouse Hepa1-6 Cells This Example illustrates that removing the WPRE element from a lentiviral vector containing the hAAT-hPAH-3'UTR$_{289}$ reduced hPAH expression significantly, indicating that WPRE is required for optimal protein expression, as shown in FIG. 10. This Example also illustrates that optimizing codon choice based on preferred human codon bias (PAH-OPT) failed to increase hPAH expression levels.

Human PAH was synthesized and inserted into lentiviral vectors. Insertion of the sequences was verified by DNA sequencing. Lentiviral vectors containing a verified hPAH sequence were then used to transduce mouse Hepa1-6 cells (purchased from American Type Culture Collection, Manassas, VA). In addition, hPAH expression in these constructs was driven by the hAAT promoter. Cells were transduced with lentiviral particles and after 2-4 days protein was analyzed by western blot for PAH expression. The relative expression of human PAH was detected by immunoblot using an anti-PAH antibody (Abcam) and the loading control Beta-actin.

This Example shows the effect on hPAH expression in Hepa1-6 cells of: 1) codon optimization of the hPAH coding region and, 2) deletion of the WPRE gene component. Expression of various hPAH constructs in mouse Hepa1-6 cells was compared to address this question. As shown in FIG. 10, five groups are compared: a Beta-actin loading control (lane 1), an optimized codon control construct (lane 2), an optimized codon construct containing a truncated hPAH 3'UTR sequence (lane 3), a control construct containing a truncated hPAH 3'UTR sequence (lane 4), and a construct with a deleted WPRE sequence and containing a truncated hPAH 3'UTR (lane 5). Hepa1-6 carcinoma cells are derived from mouse liver tissue and thus there is a natural background expression of PAH observed in Lane 1 (labeled hAAT). This Example illustrates that optimizing codon choice based on preferred human codon bias (PAH-OPT) failed to increase hPAH expression levels. As observed with the wild type hPAH gene, including a truncated 3'UTR (UTR$_{289}$) increases hPAH expression but only to levels substantially below what is observed with the wild type (non-optimized) sequence linked to UTR$_{289}$. Removing the WPRE element from a lentiviral vector containing the hAAT-hPAH-3'UTR$_{289}$ also reduces hPAH expression indicating that WPRE is required for optimal protein expression.

Example 10. shPAH-1 and shPAH-2 Reduces hPAH Expression in Human Hep3B Cells

Figure 11:
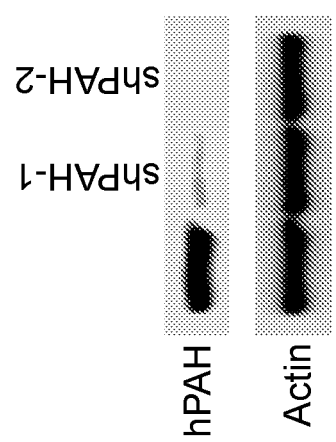
FIG. 11 depicts data demonstrating that shPAH-1 and shPAH-2 reduces hPAH expression in human Hep3B cells.

This Example demonstrates that lentivirus-delivered PAH shRNA reduces hPAH expression in human Hep3B cells, as shown in FIG. 11.

Human PAH was synthesized and inserted into lentiviral vectors. Insertion of the sequences was verified by DNA sequencing. The lentiviral vectors containing hPAH sequence was then used to transduce human Hep3B cells (purchased from American Type Culture Collection, Manassas, VA). In addition, hPAH expression in these constructs was driven by the hAAT promoter. Cells were transduced with lentiviral particles and after 2-4 days protein was analyzed by western blot for PAH expression. Insertion of the shRNA sequence in the lentiviral vector (LV) was verified by DNA sequencing using a primer complementary to the promoter used to regulate shRNA expression. The relative expression of human PAH was detected by immunoblot using an anti-PAH antibody (Abcam) and the loading control Beta-actin.

FIG. 11 compares the ability of 2 different shRNA constructs to reduce hPAH expression in Hep3B cells, namely PAH shRNA sequence #1 (shPAH-1) and PAH shRNA sequence #2 (shPAH-2). As shown in FIG. 11, three constructs are compared: a control with Hep3B cells alone (lane 1), a construct containing Hep3B cells plus shPAH-1(lane 2), and a construct containing Hep3B cells plus shPAH-2 (lane 3). Notably, Hep3B cells express endogenous PAH at significant levels. This Example illustrates that both shPAH-1 and shPAH-2 were effective in reducing endogenous hPAH expression levels.

Figure 12:
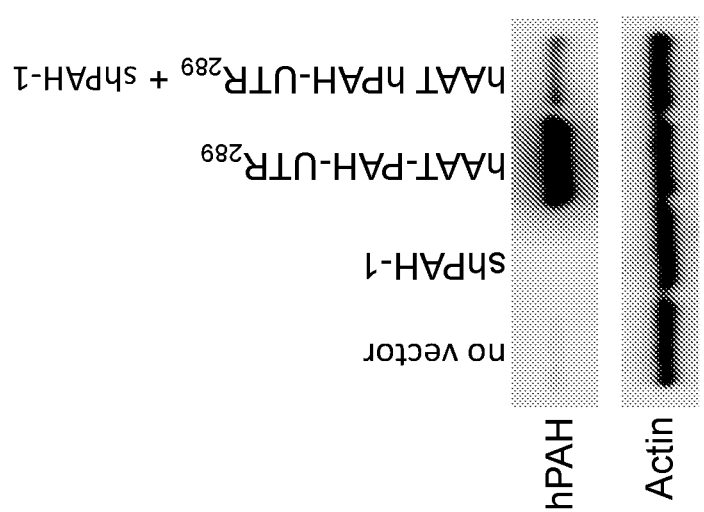
FIG. 12 depicts data demonstrating shPAH-1 suppression of endogenous hPAH and hAAT-hPAH-3'UTR$_{289}$ in Hep3B cells.

Example 11. shPAH-1 Suppression of Endogenous hPAH and hAAT-hPAH-3'UTR$_{289}$ in Hep3B Cells This Example demonstrates that shPAH-1 suppresses expression of endogenous PAH and truncated hPAH 3'UTR (hAAT-hPAH-3'UTR$_{289}$) in Hep3B cells, as shown in FIG. 12.

Human PAH was synthesized and inserted into lentiviral vectors. Insertion of the sequences was verified by DNA sequencing. Lentiviral vectors containing hPAH sequence was then used to transduce human Hep3B cells (purchased from American Type Culture Collection, Manassas, VA). Cells were transduced with lentiviral particles and after 2-4 days protein was analyzed by western blot for PAH expression. The relative expression of human PAH was detected by immunoblot with an anti-PAH antibody (Abcam) and the loading control Beta-actin. hPAH expression in both full-length and 3'UTR-truncated constructs were driven by hAAT promoter. The lentiviral vectors incorporated, in various instances, a human PAH gene with its 3'UTR, a human PAH gene with a truncated 3'UTR, and/or shPAH-1. Insertion of the shRNA sequence in the lentiviral vector (LV) was verified by DNA sequencing using a primer complementary to the promoter used to regulate shRNA expression. The target sequence for shPAH-1 is in the portion of 3'UTR that is preserved in both full-length and shortened versions.

FIG. 12 shows expression of hPAH and PAH shRNA in human Hep3B cells. As shown in FIG. 12, four groups are compared: a control comprising Hep3B cells alone (lane 1), a group comprising Hep3B cells plus a lentiviral vector expressing shPAH-1(lane 2), a control comprising hAAT-hPAH-3'UTR$_{289}$ alone (lane 3), and a group containing both hAAT-hPAH-3'UTR$_{289}$ and a lentiviral vector expressing shPAH-1. Notably, Hep3B cells alone express endogenous PAH at significant levels. This Example illustrates that shPAH-1 suppresses expression of both endogenous PAH and expression of hAAT-hPAH-3'UTR$_{289}$. Further, this confirms the significant potency of shPAH-1 against endogenous and hAAT-hPAH-3'UTR$_{289}$ in Hep3B cells.

Figure 13:
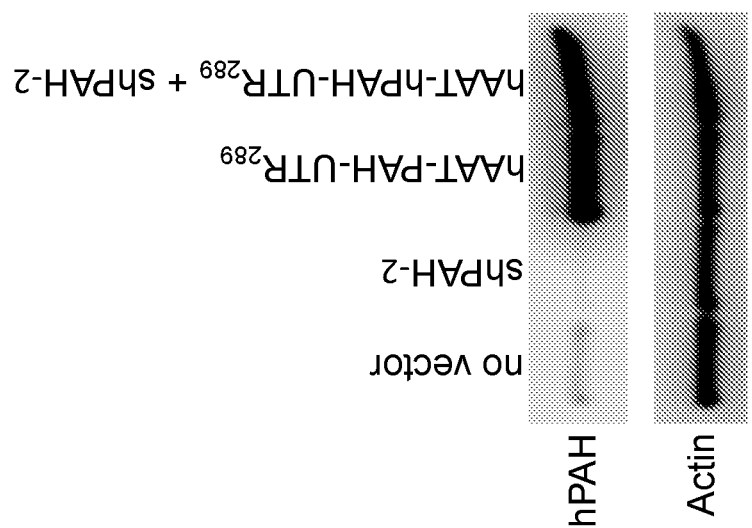
FIG. 13 depicts data demonstrating that shPAH-2 suppresses endogenous hPAH but not hAAT-hPAH-3'UTR$_{289}$ in HepG2 cells.

Example 12. shPAH-2 Suppression of Endogenous hPAH but not hAAT-hPAH-3'UTR$_{289}$ in HepG2 Cells This Example illustrates that shPAH-2 suppresses expression of endogenous PAH but does not suppress expression of hAAT-hPAH-3'UTR$_{289}$ in HepG2 cells, as shown in FIG. 13.

Human PAH was synthesized and inserted into lentiviral vectors. Insertion of the sequences was verified by DNA sequencing. Lentiviral vectors containing hPAH sequence was then used to transduce human Hep3B cells (purchased from American Type Culture Collection, Manassas, VA). Cells were transduced with lentiviral particles and after 2-4 days protein was analyzed by western blot for PAH expression. The relative expression of human PAH was detected by immunoblot using an anti-PAH antibody (Abcam) and the loading control Beta-actin. hPAH expression in both full-length and 3'UTR-truncated constructs were driven by hAAT promoter. The lentiviral vectors incorporated, in various instances, a human PAH gene with its 3'UTR, a human PAH gene with a truncated 3'UTR, and/or shPAH-2. Insertion of the shRNA sequence in the lentiviral vector (LV) was verified by DNA sequencing using a primer complementary to the promoter used to regulate shPAH-2 expression. The target sequence for shPAH-2 is in the distal portion of the hPAH 3'UTR that is present in full-length hPAH construct but absent in the truncated hPAH construct (hAAT-hPAH-3'UTR$_{289}$).

FIG. 13 shows expression of hPAH and PAH shRNA in human Hep3B cells. As shown in FIG. 13, four groups are compared: a control with HepG2 cells alone (lane 1), HepG2 cells plus a lentiviral vector expressing shPAH-2 (lane 2), a control with lentiviral vector expressing truncated hPAH 3'UTR (lane 3), and a lane containing both a lentiviral vector expressing truncated hPAH 3'UTR (hPAH-3'UTR) and a lentiviral vector expressing shPAH-2. This Example illustrates that the shPAH-2 sequence suppresses expression of endogenous PAH but has no discernible effect on expression of hAAT-hPAH-3'UTR$_{289}$.

Example 13. Preliminary Test of hAAT-PAH-UTR in the Pah(Enu2) Mouse

FIG. 14 summarizes results from a preliminary test of hAAT-PAH-UTR in the Pah(enu2) mouse that is a standard model for experimental studies on PKU (Shedlovsky, McDonald et al. 1993, Fang, Eisensmith et al. 1994, Mochizuki, Mizukami et al. 2004, Oh, Park et al. 2004). Panel A shows that lentivirus vector hAAT-PAH injected directly into the liver of neonatal Pah(enu2) mice substantially corrects a growth defect seen in mice that received only a control lentivirus vector that does not express PAH. Panel B provides a cluster plot representation of data in Panel A showing a clear overlap between weight gain curves for normal mice and Pah(enu2) treated with LV-hAAT-PAH. Panel C shows that LV-hAAT-PAH was effective in female mice. This is important because the PAH defect in females is more difficult to correct compared to male mice. Panel D plots the plasma phenylalanine levels for control (normal) mice, Pah(enu2) mice treated with LV-hAAT-PAH and Pah (enu2) mice treated with a control lentivirus vector that does not express PAH.

Experimental Methodology:

Neonatal mice aged 1 to 2 days were divided into three groups of four neonatal mice each. The first group of neonatal mice comprise a control group with normal PAH expression activity. The second and third group of neonatal mice contain the mutation PAH(enu2), which is a chemically induced mutation in the PAH gene that inhibits enzymatic activity of PAH.

The first group of neonatal mice were injected with lentiviral vectors comprising the hAAT promoter, human PAH, an elongation factor (EF1), and green fluorescent protein (GFP). The second group of neonatal mice were injected with lentiviral vectors lacking human PAH but comprising the hAAT promoter, an elongation factor (EF1), and green fluorescent protein (GFP). The third group of neonatal mice were injected with lentiviral vectors comprising the hAAT promoter, human PAH, an elongation factor (EF1), and green fluorescent protein (GFP).

Neonatal mice were injected with 10 µL of a lentivirus particle suspension containing between $1\times10^6$ to $1\times10^{10}$ transducing units per mL of normal saline or blood plasma substitute directly into the liver. Prior to injection, neonatal mice were treated with clodronate liposomes to deplete liver Kupffer cells.

Neonatal mice were monitored for phenotypic changes associated with reduced phenylalanine levels in the blood, including coat color changes, PAH and phenylalanine levels, and behavior. At 0, 4, and 8 weeks post-injection, blood phenylalanine levels were measured. At 0, 2, 4, and 8 weeks post-injection, neonatal mice weight were measured. If the growth of neonatal mice in group three improved over growth of neonatal mice in group two, behavioral tests will be performed, including the T-maze Spontaneous Alternation Test and the Win-Stay Eight-arm Radial Maze Task. At 8 weeks post-injection, two mice from each group will be sacrificed and human PAH expression in the liver will be measured. Methylome assessment and long bone and spinal bone assessments will be performed on sacrificed mice. The remaining mice were maintained and blood phenylalanine will was measured at 6 months post-injection.

Example 14. Lentiviral-Delivered Expression of the Human PAH Gene Using hAAT and CMV Promoters in Hepa1-6 Mouse Hepatoma Cells This Example illustrates that utilization of hPAH expression constructs under control of the CMV immediate early promoter provides high-level expression irrespective of the presence or absence of 3'UTR and irrespective of whether or not the 3'UTR is truncated, as shown in FIG. 15.

Human PAH was synthesized and inserted into lentiviral vectors. Insertion of the sequences was verified by DNA sequencing. Lentiviral vectors containing hPAH sequence was then used to transduce human Hep3B cells (purchased from American Type Culture Collection, Manassas, VA). Cells were transduced with lentiviral particles and after 2-4 days protein was analyzed by western blot for PAH expression. The relative expression of human PAH was detected by immunoblot using an anti-PAH antibody (Abcam) or an anti-tubulin antibody (Sigma) as the loading control. hPAH expression in both full-length and 3'UTR-truncated constructs were driven by hAAT promoter or CMV promoter, respectively. The lentiviral vectors incorporated, in various instances, a human PAH gene with its 3'UTR, a human PAH gene with a truncated 3'UTR, in the absence or presence of hAAT promoter or CMV promoter.

Figure 15:
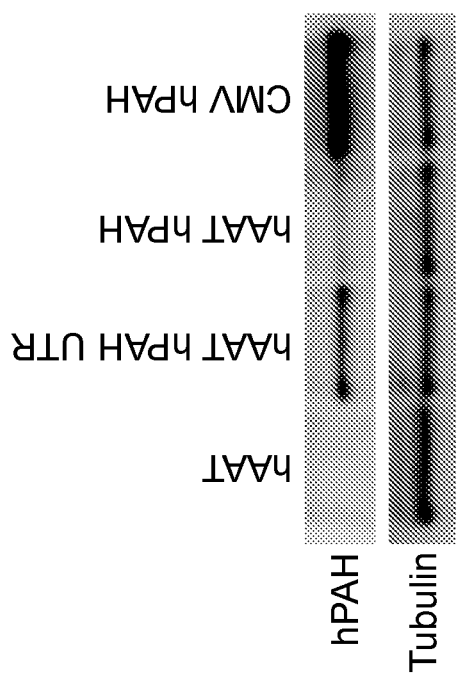
FIG. 15 depicts data demonstrating lentiviral-delivered expression of the human PAH gene using hAAT and CMV promoters in Hepa1-6 mouse hepatoma cells.

As shown in FIG. 15, four groups are compared: a control with Hepa1-6 cells and hAAT promoter alone (lane 1), a lentiviral vector expressing full-length 3'UTR hPAH under control of the hAAT promoter (lane 2), a lentiviral vector expressing truncated 3'UTR hPAH under control of the hAAT promoter (lane 3), and a group with a lentiviral vector expressing truncated 3'UTR hPAH under control of the CMV promoter. This Example illustrates that hPAH expression under control of the CMV immediate early promoter gives rise to high-level expression irrespective of the presence or absence of UTR and irrespective of whether or not the UTR is truncated. This permits the generation of constructs for specific expression in liver tissue while still achieving high-level production of hPAH. Notably, restricting transgene expression to liver cells is an important consideration for vector safety and target specificity in a genetic medicine for phenylketonuria.

Example 15. Lentivirus-Delivered Expression of hPAH Using Expression Constructs with the hAAT Promoter and Liver-Specific Enhancer Element ApoE (1), ApoE (2), or Prothrombin in Mouse Hepa1-6 Cells This Example illustrates that ApoE (1), ApoE (2), and prothrombin enhancers may be utilized to increase expression of PAH in mouse Hepa1-6 cells.

Human PAH was synthesized and inserted into lentiviral vectors. Insertion of the sequences was verified by DNA sequencing. Lentiviral vectors containing hPAH sequence was then used to transduce human Hep3B cells (purchased from American Type Culture Collection, Manassas, VA). Cells were transduced with lentiviral particles and after 2-4 days protein was analyzed by western blot for PAH expression. PAH was detected by immunoblot using an anti-PAH antibody and an anti-Beta actin antibody for the loading control.

Figure 16:
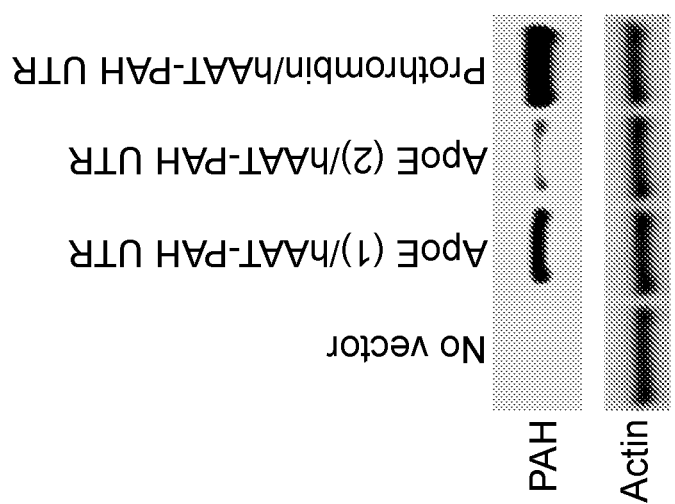
FIG. 16 depicts demonstrating lentivirus-delivered expression of hPAH using expression constructs with the hAAT promoter and liver-specific enhancer element ApoE (1), ApoE (2), or prothrombin in mouse Hepa1-6 cells.

As shown in FIG. 16, four groups are compared: a control with Hepa1-6 cells alone (lane 1), a lentiviral vector expressing ApoE(1) enhancer with full-length 3'UTR hPAH under control of the hAAT promoter (lane 2), a lentiviral vector expressing ApoE(2) enhancer with full-length 3'UTR hPAH under control of the hAAT promoter (lane 3), and a lentiviral vector expressing the prothrombin enhancer with full-length 3'UTR hPAH under control of the hAAT promoter (lane 3). This Example illustrates that ApoE (1), ApoE (2), and prothrombin enhancers may each be utilized to increase expression of PAH in mouse Hepa1-6 cells under control of the hAAT promoter.

The disclosure of the above example embodiments is intended to be illustrative, but not limiting, of the scope of the inventions, which are set forth in the following claims and their equivalents. Although example embodiments of the inventions have been described) some detail for purposes of clarity of understanding, it will be apparent that certain changes and modifications can be practiced within the scope of the following claims. In the following claims, elements and/or steps do not imply any particular order of operation, unless explicitly stated in the claims or implicitly required by the disclosure.

Sequence Listings

| SEQ ID NO: | Description | Sequence |
|---|---|---|
| 1 | PAH | ATGTCCACTGCGGTCCTGGAAAACCCAGGCTTGGGCAGGAAACTCT<br>CTGACTTTGGACAGGAAACAAGCTATATTGAAGACAACTGCAATCA<br>AAATGGTGCCATATCACTGATCTTCTCACTCAAAGAAGAAGTTGGT<br>GCATTGGCCAAAGTATTGCGCTTATTTGAGGAGAATGATGTAAACC<br>TGACCCACATTGAATCTAGACCTTCTCGTTTAAAGAAAGATGAGTA<br>TGAATTTTTCACCCATTTGGATAAACGTAGCCTGCCTGCTCTGACA<br>AACATCATCAAGATCTTGAGGCATGACATTGGTGCCACTGTCCATG<br>AGCTTTCACGAGATAAGAAGAAAGACACAGTGCCCTGGTTCCCAAG<br>AACCATTCAAGAGCTGGACAGATTTGCCAATCAGATTCTCAGCTAT<br>GGGAGCGGAACTGGATGCTGACCACCCTGGTTTTAAAGATCCTGTGT<br>ACCGTGCAAGACGGAAGCAGTTTGCTGACATTGCCTACAACTACCG<br>CCATGGGCAGCCCATCCCTCGAGTGGAATACATGGAGGAAGAAAAG<br>AAAACATGGGGCACAGTGTTCAAGACTCTGAAGTCCTTGTATAAAA<br>CCCATGCTTGCTATGAGTACAATCACATTTTTCCACTTCTTGAAAA<br>GTACTGTGGCTTCCATGAAGATAACATTCCCCAGCTGGAAGACGTT<br>TCTCAATTCCTGCAGACTTGCACTGGTTTCCGCCTCCGACCTGTGG<br>CTGGCCTGCTTTCCTCTCGGGATTTCTTGGGTGGCCTGGCCTTCCG<br>AGTCTTCCACTGCACACAGTACATCAGACATGGATCCAAGCCCATG<br>TATACCCCCGAACCTGACATCTGCCATGAGCTGTTGGGACATGTGC<br>CCTTGTTTTCAGATCGCAGCTTTGCCCAGTTTTCCCAGGAAATTGG<br>CCTTGCCTCTCTGGGTGCACCTGATGAATACATTGAAAAGCTCGCC<br>ACAATTTACTGGTTTACTGTGGAGTTTGGGCTCTGCAAACAAGGAG<br>ACTCCATAAAGGCATATGGTGCTGGGCTCCTGTCATCCTTTGGTGA<br>ATTACAGTACTGCTTATCAGAGAAGCCAAAGCTTCTCCCCCTGGAG<br>CTGGAGAAGACAGCCATCCAAAATTACACTGTCACGGAGTTCCAGC<br>CCCTGTATTACGTGGCAGAGAGTTTTAATGATGCCAAGGAGAAAGT<br>AAGGAACTTTGCTGCCACAATACCTCGGCCCTTCTCAGTTCGCTAC<br>GACCCATACACCCAAAGGATTGAGGTCTTGGACAATACCCAGCAGC<br>TTAAGATTTTGGCTGATTCCATTAACAGTGAAATTGGAATCCTTTG<br>CAGTGCCCTCCAGAAAATAAAGTAA |
| 2 | Codon optimized PAH | ATGAGCACAGCTGTGTTGGAAAATCCTGGGCTGGGCCGTAAGCTTT<br>CCGATTTCGGCCAGGAGACTTCATACATTGAGGACAACTGCAACCA<br>GAATGGGGCCATTTCTTTGATCTTCAGTCTCAAAGAAGAGGTAGGC<br>GCTCTGGCTAAGGTCCTGAGGCTGTTTGAGGAAAATGACGTGAATC<br>TGACACACATTGAGTCTAGGCCTTCCCGACTTAAGAAGGATGAGTA<br>TGAGTTCTTCACACACCTGGACAAACGATCTCTCCCAGCACTGACC<br>AATATCATCAAGATTCTCAGGCATGATATCGGTGCCACGGTCCACG<br>AACTTTCACGCGATAAGAAGAAAGACACAGTTCCTGGTTCCCGAG<br>AACCATTCAGGAACTGGATAGGTTTGCCAATCAGATTCTGAGCTAT<br>GGGGCAGAGTTGGATGCCGACCATCCAGGCTTCAAAGACCCCGTAT<br>ATCGGGCTCGGAGAAAGCAGTTTGCAGACATCGCTTACAATTACAG<br>GCATGGACAGCCCCATCCCTAGAGTGGAGTACATGGAAGAAGGCAAG<br>AAAAACCTGGGGAACGGTGTTTAAGACCCTCAAAAGCCTGTATAAGA<br>CCCACGCGTGTTATGAGTACAACCACATTTTCCCATTGCTGGAGAA<br>GTACTGTGGCTTTCACGAGGACAACATCCCTCAACTGGAGGATGTT<br>TCACAGTTCCTTCAGACTTGCACTGGTTTCCGCCTTCGACCTGTGG<br>CTGGGCTGCTTAGCTCACGGGACTTCCTGGGAGGCCTGGCCTTCAG<br>AGTCTTTCACTGCACTCAGTACATTCGGCATGGCTCTAAGCCAATG<br>TACACCCCTGAACCGGATATATGCCACGAGCTGTTGGGACATGTGC<br>CCCTGTTTTCTGATCGCAGCTTTGCCCAGTTTTCCCAGGAGATTGG<br>CCTGGCAAGTCTTGGTGCGCCTGATGAGTACATCGAGAAGCTCGCG<br>ACAATCTACTGGTTCACCGTGGAATTTGGACTCTGCAAACAAGGGG<br>ACTCTATCAAAGCCTACGGAGCAGGACTCCTCTCCAGCTTCGGTGA<br>ACTGCAGTATTGTCTGTCCGAGAAACCCAAACTCTTGCCCCTGGAA<br>CTGGAAAAGACTGCCATCCAAAACTATACTGTCACGGAATTTCAGC<br>CACTGTATTATGTGGCTGAATCCTTTAACGATGCCAAGGAGAAGGT<br>CCGTAATTTTGCTGCCACAATACCACGCCCCTTCAGCGTGAGATAC<br>GACCCGTATACACAACGGATAGAGGTTCTGGACAACACCCAGCAAC<br>TGAAAATTCTGGCAGACAGTATAAACAGCGAAATAGGGATCCTCTG<br>TAGTGCCCTGCAGAAAATCAAATGA |
| 3 | PAH 3'UTR sequence (897 nucleotides) | AGCCATGGACAGAATGTGGTCTGTCAGCTGTGAATCTGTTGATGGA<br>GATCCAACTATTTCTTTCATCAGAAAAAGTCCGAAAAGCAAACCTT<br>AATTTGAAATAACAGCCTTAAATCCTTTACAAGATGGAGAAACAAC<br>AAATAAGTCAAAATAATCTGAAATGACAGGATATGAGTACATACTC<br>AAGAGCATAATGGTAAATCTTTTGGGGTCATCTTTGATTTAGAGAT<br>GATAATCCCATACTCTCAATTGAGTTAAATCAGTAATCTGTCGCAT<br>TTCATCAAGATTAATTAAAATTTGGGACCTGCTTCATTCAAGCTTC<br>ATATATGCTTTGCAGAGAACTCATAAAGGAGCATATAAGGCTAAAT<br>GTAAAACCCAAGACTGTCATTAGAATTGAATTATTGGGCTTAATAT<br>AAATCGTAACCTATGAAGTTTATTTTTTATTTTAGTTAACTATGAT<br>TCCAATTACTACTTTGTTATTGTACCTAAGTAAATTTTCTTTAAGT<br>CAGAAGCCCATTAAAATAGTTACAAGCATTGAACTTCTTTAGTATT<br>ATATTAATATAAAACATTTTTGTATGTTTTATTGTAATCATAAAT<br>ACTGCTGTATAAGGTAATAAAACTCTGCACCTAATCCCCATAACTT<br>CCAGTATCATTTTCCAATTAATTATCAAGTCTGTTTTGGGAAACAC |

-continued

Sequence Listings

| SEQ ID NO: | Description | Sequence |
|---|---|---|
| | | TTTGAGGACATTTATGATGCAGCAGATGTTGACTAAAGGCTTGGTT<br>GGTAGATATTCAGGAAATGTTCACTGAATAAATAAGTAAATACATT<br>ATTGAAAAGCAAATCTGTATAAATGTGAAATTTTTATTTGTATTAG<br>TAATAAAACATTAGTAGTTTAAACAAAAAAAAAAAAAAAAAAAAA<br>AAAAAAAAACTCGACTCTAGATT |
| 4 | PAH 3'UTR sequence (289 nucleotides) | AGCCATGGACAGAATGTGGTCTGTCAGCTGTGAATCTGTTGATGGA<br>GATCCAACTATTTCTTTCATCAGAAAAAGTCCGAAAAGCAAACCTT<br>AATTTGAAATAACAGCCTTAAATCCTTTACAAGATGGGAGAAACAAC<br>AAATAAGTCAAAATAATCTGAAATGACAGGATATGAGTACATACTC<br>AAGAGCATAATGGTAAATCTTTTGGGGTCATCTTTGATTTAGAGAT<br>GATAATCCCATACTCTCAATTGAGTTAAATCAGTAATCTGTCGCAT<br>TTCATCAAGATTA |
| 5 | PAH shRNA sequence #1 | TCGCATTTCATCAAGATTAATCTCGAGATTAATCTTGATGAAATGC<br>GATTTTT |
| 6 | PAH shRNA sequence #2 | ACTCATAAAGGAGCATATAAGCTCGAGCTTATATGCTCCTTTATGA<br>GTTTTTT |
| 7 | Rous Sarcoma virus (RSV) promoter | GTAGTCTTATGCAATACTCTTGTAGTCTTGCAACATGGTAACGATG<br>AGTTAGCAACATGCCTTACAAGGAGAGAAAAAGCACCGTGCATGCC<br>GATTGGTGGAAGTAAGGTGGTACGATCGTGCCTTATTAGGAAGGCA<br>ACAGACGGGTCTGACATGGATTGGACGAACCACTGAATTGCCGCAT<br>TGCAGAGATATTGTATTTAAGTGCCTAGCTCGATACAATAAACG |
| 8 | 5' Long terminal repeat (LTR) | GGTCTCTCTGGTTAGACCAGATCTGAGCCTGGGAGCTCTCTGGCTA<br>ACTAGGGAACCCACTGCTTAAGCCTCAATAAAGCTTGCCTTGAGTG<br>CTTCAAGTAGTGTGTGCCCGTCTGTTGTGTGACTCTGGTAACTAGA<br>GATCCCTCAGACCCTTTTAGTCAGTGTGGAAAATCTCTAGCA |
| 9 | Psi Packaging signal | TACGCCAAAAATTTTGACTAGCGGAGGCTAGAAGGAGAGAG |
| 10 | Rev response element (RRE) | AGGAGCTTTGTTCCTTGGGTTCTTGGGAGCAGCAGGAAGCACTATG<br>GGCGCAGCCTCAATGACGCTGACGGTACAGGCCAGACAATTATTGT<br>CTGGTATAGTGCAGCAGCAGAACAATTTGCTGAGGGCTATTGAGGC<br>GCAACAGCATCTGTTGCAACTCACAGTCTGGGGCATCAAGCAGCTC<br>CAGGCAAGAATCCTGGCTGTGGAAAGATACCTAAAGGATCAACAGC<br>TCC |
| 11 | Central polypurine tract (cPPT) | TTTTAAAAGAAAAGGGGGGATTGGGGGGTACAGTGCAGGGGAAAGA<br>ATAGTAGACATAATAGCAACAGACATACAAACTAAAGAATTACAAA<br>AACAAATTACAAAATTCAAAATTTTA |
| 12 | Human alpha-1 antitrypsin promoter (hAAT) | GATCTTGCTACCAGTGGAACAGCCACTAAGGATTCTGCAGTGAGAG<br>CAGAGGGCCAGCTAAGTGGTACTCTCCCAGAGACTGTCTGACTCAC<br>GCCACCCCCTCCACCTTGGACACAGGACGCTGTGGTTTCTGAGCCA<br>GGTACAATGACTCCTTTCGGTAAGTGCAGTGGAAGCTGTACACTGC<br>CCAGGCAAAGCGTCCGGGCAGCGTAGGCGGGCGACTCAGATCCCAG<br>CCAGTGGACTTAGCCCCTGTTTGCTCCTCCGATAACTGGGGTGACC<br>TTGGTTAATATTCACCAGCAGCCTCCCCCGTTGCCCCTCTGGATCC<br>ACTGCTTAAATACGGACGAGGACAGGGCCCTGTCTCCTCAGCTTCA<br>GGCACCACCACTGACCTGGGACAGTGAAT |
| 13 | Long WPRE sequence | AATCAACCTCTGATTACAAAATTTGTGAAAGATTGACTGGTATTCT<br>TAACTATGTTGCTCCTTTTACGCTATGTGGATACGCTGCTTTAATG<br>CCTTTGTATCATGCTATTGCTTCCCGTATGGCTTTCATTTTCTCCT<br>CCTTGTATAAATCCTGGTTGCTGTCTCTTTATGAGGAGTTGTGGCC<br>CGTTGTCAGGCAACGTGGCGTGGTGTGCACTGTGTTTGCTGACGCA<br>ACCCCCACTGGTTGGGGCATTGCCACCACCTGTCAGCTCCTTTCCG<br>GGACTTTCGCTTTCCCCCTCCCTATTGCCACGGCGGAACTCATCGC<br>CGCCTGCCTTGCCCGCTGCTGGACAGGGGCTCGGCTGTTGGGCACT<br>GACAATTCCGTGGTGTTGTCGGGGAAATCATCGTCCTTTCCTTGGC<br>TGCTCGCCTGTGTTGCCACCTGGATTCTGCGCGGGACGTCCTTCTG<br>CTACGTCCCTTCGGCCCTCAATCCAGCGGACCTTCCTTCCCGCGGC<br>CTGCTGCCGGCTCTGCGGCCTCTTCCGCGTCTTCGCCTTCGCCCTC<br>AGACGAGTCGGATCTCCCTTTGGGCCGCCTCCCCGCCT |
| 14 | 3'delta LTR | TGGAAGGGCTAATTCACTCCCAACGAAGATAAGATCTGCTTTTTGC<br>TTGTACTGGGTCTCTCTGGTTAGACCAGATCTGAGCCTGGGAGCTC<br>TCTGGCTAACTAGGGAACCCACTGCTTAAGCCTCAATAAAGCTTGC<br>CTTGAGTGCTTCAAGTAGTGTGTGCCCGTCTGTTGTGTGACTCTGG<br>TAACTAGAGATCCCTCAGACCCTTTTAGTCAGTGTGGAAAATCTCT<br>AGCAGTAGTAGTTCATGTCA |

| SEQ ID NO: | Description | Sequence |
|---|---|---|
| 15 | H1 Promoter | GAACGCTGACGTCATCAACCCGCTCCAAGGAATCGCGGGCCCAGTG<br>TCACTAGGCGGGAACACCCAGCGCGCGTGCGCCCTGGCAGGAAGAT<br>GGCTGTGAGGGACAGGGGAGTGGCGCCCTGCAATATTTGCATGTCG<br>CTATGTGTTCTGGGAAATCACCATAAACGTGAAATGTCTTTGGATT<br>TGGGAATCTTATAAGTTCTGTATGAGACCACTT |
| 16 | CAG promoter | TAGTTATTAATAGTAATCAATTACGGGGTCATTAGTTCATAGCCCA<br>TATATGGAGTTCCGCGTTACATAACTTACGGTAAATGGCCCGCCTG<br>GCTGACCGCCCAACGACCCCCGCCCATTGACGTCAATAATGACGTA<br>TGTTCCCATAGTAACGCCAATAGGGACTTTCCATTGACGTCAATGG<br>GTGGACTATTTACGGTAAACTGCCCACTTGGCAGTACATCAAGTGT<br>ATCATATGCCAAGTACGCCCCCTATTGACGTCAATGACGGTAAATG<br>GCCCGCCTGGCATTATGCCCAGTACATGACCTTATGGGACTTTCCT<br>ACTTGGCAGTACATCTACGTATTAGTCATCGCTATTACCATGGGTC<br>GAGGTGAGCCCCACGTTCTGCTTCACTCTCCCCATCTCCCCCCCCT<br>CCCCACCCCCAATTTTGTATTTATTTATTTTTTAATTATTTTGTGC<br>AGCGATGGGGGCGGGGGGGGGGGGGCGCGCGCCAGGCGGGGCGGG<br>GCGGGGCGAGGGGCGGGGCGGGGCGAGGCGGAGAGGTGCGGCGGCA<br>GCCAATCAGAGCGGCGCGCTCCGAAAGTTTCCTTTTATGGCGAGGC<br>GGCGGCGGCGGCGGCCCTATAAAAAGCGAAGCGCGCGGCGGGCG |
| 17 | HIV Gag | ATGGGTGCGAGAGCGTCAGTATTAAGCGGGGGAGAATTAGATCGAT<br>GGGAAAAAATTCGGTTAAGGCCAGGGGGAAAGAAAAAATATAAATT<br>AAAACATATAGTATGGGCAAGCAGGGAGCTAGAACGATTCGCAGTT<br>AATCCTGGCCTGTTAGAAACATCAGAAGGCTGTAGACAAATACTGG<br>GACAGCTACAACCATCCCTTCAGACAGGATCAGAAGAACTTAGATC<br>ATTATATAATACAGTAGCAACCCTCTATTGTGTGCATCAAAGGATA<br>GAGATAAAAGACACCAAGGAAGCTTTAGACAAGATAGAGGAAGAGC<br>AAAACAAAAGTAAGAAAAAAGCACAGCAAGCAGCAGCTGACACAGG<br>ACACAGCAATCAGGTCAGCCAAAATTACCCTATAGTGCAGAACATC<br>CAGGGGCAAATGGTACATCAGGCCATATCACCTAGAACTTTAAATG<br>CATGGGTAAAAGTAGTAGAAGAGAAGGCTTTCAGCCCAGAAGTGAT<br>ACCCATGTTTTCAGCATTATCAGAAGGAGCCACCCCACAAGATTTA<br>AACACCATGCTAAACACAGTGGGGGGACATCAAGCAGCCATGCAAA<br>TGTTAAAAGAGACCATCAATGAGGAAGCTGCAGAATGGGATAGAGT<br>GCATCCAGTGCATGCAGGGCCTATTGCACCAGGCCAGATGAGAGAA<br>CCAAGGGGAAGTGACATAGCAGGAACTACTAGTACCCTTCAGGAAC<br>AAATAGGATGGATGACACATAATCCACCTATCCCAGTAGGAGAAAT<br>CTATAAAAGATGGATAATCCTGGGATTAAATAAAATAGTAAGAATG<br>TATAGCCCTACCAGCATTCTGGACATAAGACAAGGACCAAAGGAAC<br>CCTTTAGAGACTATGTAGACCGATTCTATAAAACTCTAAGAGCCGA<br>GCAAGCTTCACAAGAGGTAAAAAATTGGATGACAGAAACCTTGTTG<br>GTCCAAAATGCGAACCCAGATTGTAAGACTATTTTAAAAGCATTGG<br>GACCAGGAGCGACACTAGAAGAAATGATGACAGCATGTCAGGGAGT<br>GGGGGGACCCGGCCATAAAGCAAGAGTTTTGGCTGAAGCAATGAGC<br>CAAGTAACAAATCCAGCTACCATAATGATACAGAAAGGCAATTTTA<br>GGAACCAAAGAAAGACTGTTAAGTGTTTCAATTGTGGCAAAGAAGG<br>GCACATAGCCAAAATTGCAGGGCCCCTAGGAAAAAGGGCTGTTGG<br>AAATGTGGAAAGGAAGGACACCAAATGAAAGATTGTACTGAGAGAC<br>AGGCTAATTTTTTAGGGAAGATCTGGCCTTCCCACAAGGGAAGGCC<br>AGGGAATTTTCTTCAGAGCAGACCAGAGCCAACAGCCCCACCAGAA<br>GAGAGCTTCAGGTTTGGGGAAGAGACAACAACTCCCTCTCAGAAGC<br>AGGAGCCGATAGACAAGGAACTGTATCCTTTAGCTTCCCTCAGATC<br>ACTCTTTGGCAGCGACCCCTCGTCACAATAA |
| 18 | HIV Pol | ATGAATTTGCCAGGAAGATGGAAACCAAAAATGATAGGGGGAATTG<br>GAGGTTTTATCAAAGTAGGACAGTATGATCAGATACTCATAGAAAT<br>CTGCGGACATAAAGCTATAGGTACAGTATTAGTAGGACCTACACCT<br>GTCAACATAATTGGAAGAAATCTGTTGACTCAGATTGGCTGCACTT<br>TAAATTTTCCCATTAGTCCTATTGAGACTGTACCAGTAAAATTAAA<br>GCCAGGAATGGATGGCCCAAAAGTTAAACAATGGCCATTGACAGAA<br>GAAAAAATAAAAGCATTAGTAGAAATTTGTACAGAAATGGAAAAGG<br>AAGGAAAAATTTCAAAAATTGGGCCTGAAAATCCATACAATACTCC<br>AGTATTTGCCATAAAGAAAAAAGACAGTACTAAATGGAGAAAATTA<br>GTAGATTTCAGAGAACTTAATAAGAGAACTCAAGATTTCTGGGAAG<br>TTCAATTAGGAATACCACATCCTGCAGGGTTAAAACAGAAAAAATC<br>AGTAACAGTACTGGATGTGGGCGATGCATATTTTTCAGTTCCCTTA<br>GATAAAGACTTCAGGAAGTATACTGCATTTACCATACCTAGTATAA<br>ACAATGAGACACCAGGGATTAGATATCAGTACAATGTGCTTCCACA<br>GGGATGGAAAGGATCACCAGCAATATTCCAGTGTAGCATGACAAAA<br>ATCTTAGAGCCTTTTAGAAAACAAAATCCAGACATAGTCATCTATC<br>AATACATGGATGATTTGTATGTAGGATCTGACTTAGAAATAGGGCA<br>GCATAGAACAAAAATAGAGGAACTGAGACAACATCTGTTGAGGTGG<br>GGATTTACCACACCAGACAAAAAACATCAGAAAGAACCTCCATTCC |

| SEQ ID NO: | Description | Sequence |
|---|---|---|
| | | TTTGGATGGGTTATGAACTCCATCCTGATAAATGGACAGTACAGCC<br>TATAGTGCTGCCAGAAAAGGACAGCTGGACTGTCAATGACATACAG<br>AAATTAGTGGGAAAATTGAATTGGGCAAGTCAGATTTATGCAGGGA<br>TTAAAGTAAGGCAATTATGTAAACTTCTTAGGGGAACCAAAGCACT<br>AACAGAAGTAGTACCACTAACAGAAGAAGCAGAGCTAGAACTGGCA<br>GAAAACAGGGAGATTCTAAAAGAACCGGTACATGGAGTGTATTATG<br>ACCCATCAAAAGACTTAATAGCAGAAATACAGAAGCAGGGGCAAGG<br>CCAATGGACATATCAAATTTATCAAGAGCCATTTAAAAATCTGAAA<br>ACAGGAAAATATGCAAGAATGAAGGGTGCCCACACTAATGATGTGA<br>AACAATTAACAGAGGCAGTACAAAAAATAGCCACAGAAAGCATAGT<br>AATATGGGGAAAGACTCCTAAATTTAAATTACCCATACAAAAGGAA<br>ACATGGGAAGCATGGTGGACAGAGTATTGGCAAGCCACCTGGATTC<br>CTGAGTGGGAGTTTGTCAATACCCCTCCCTTAGTGAAGTTATGGTA<br>CCAGTTAGAGAAAGAACCCATAATAGGAGCAGAAACTTTCTATGTA<br>GATGGGGCAGCCAATAGGGAAACTAAATTAGGAAAAGCAGGATATG<br>TAACTGACAGAGGAAGACAAAAAGTTGTCCCCCTAACGGACACAAC<br>AAATCAGAAGACTGAGTTACAAGCAATTCATCTAGCTTTGCAGGAT<br>TCGGGATTAGAAGTAAACATAGTGACAGACTCACAATATGCATTGG<br>GAATCATTCAAGCACAACCAGATAAGAGTGAATCAGAGTTAGTCAG<br>TCAAATAATAGAGCAGTTAATAAAAAAGGAAAAAGTCTACCTGGCA<br>TGGGTACCAGCACACAAAGGAATTGGAGGAAATGAACAAGTAGATG<br>GGTTGGTCAGTGCTGGAATCAGGAAAGTACTA |
| 19 | HIV Int | TTTTTAGATGGAATAGATAAGGCCCAAGAAGAACATGAGAAATATC<br>ACAGTAATTGGAGAGCAATGGCTAGTGATTTTAACCTACCACCTGT<br>AGTAGCAAAAGAAATAGTAGCCAGCTGTGATAAATGTCAGCTAAAA<br>GGGGAAGCCATGCATGGACAAGTAGACTGTAGCCCAGGAATATGGC<br>AGCTAGATTGTACACATTTAGAAGGAAAAGTTATCTTGGTAGCAGT<br>TCATGTAGCCAGTGGATATATAGAAGCAGAAGTAATTCCAGCAGAG<br>ACAGGGCAAGAAACAGCATACTTCCTCTTAAAATTAGCAGGAAGAT<br>GGCCAGTAAAAACAGTACATACAGACAATGGCAGCAATTTCACCAG<br>TACTACAGTTAAGGCCGCCTGTTGGTGGGCGGGATCAAGCAGGAA<br>TTTGGCATTCCCTACAATCCCCAAAGTCAAGGAGTAATAGAATCTA<br>TGAATAAAGAATTAAAGAAAATTATAGGACAGGTAAGAGATCAGGC<br>TGAACATCTTAAGACAGCAGTACAAATGGCAGTATTCATCCACAAT<br>TTTAAAAGAAAAGGGGGGATTGGGGGGTACAGTGCAGGGGAAAGAA<br>TAGTAGACATAATAGCAACAGACATACAAACTAAAGAATTACAAAA<br>ACAAATTACAAAAATTCAAAATTTTCGGGTTTATTACAGGGACAGC<br>AGAGATCCAGTTTGGAAAGGACCAGCAAAGCTCCTCTGGAAAGGTG<br>AAGGGGCAGTAGTAATACAAGATAATAGTGACATAAAAGTAGTGCC<br>AAGAAGAAAAGCAAAGATCATCAGGGATTATGGAAAACAGATGGCA<br>GGTGATGATTGTGTGGCAAGTAGACAGGATGAGGATTAA |
| 20 | HIV RRE | AGGAGCTTTGTTCCTTGGGTTCTTGGGAGCAGCAGGAAGCACTATG<br>GGCGCAGCGTCAATGACGCTGACGGTACAGGCCAGACAATTATTGT<br>CTGGTATAGTGCAGCAGCAGAACAATTTGCTGAGGGCTATTGAGGC<br>GCAACAGCATCTGTTGCAACTCACAGTCTGGGGCATCAAGCAGCTC<br>CAGGCAAGAATCCTGGCTGTGGAAAGATACCTAAAGGATCAACAGC<br>TCCT |
| 21 | HIV Rev | ATGGCAGGAAGAAGCGGAGACAGCGACGAAGAACTCCTCAAGGCAG<br>TCAGACTCATCAAGTTTCTCTATCAAAGCAACCCACCTCCCAATCC<br>CGAGGGGACCCGACAGGCCCGAAGGAATAGAAGAAGAAGGTGGAGA<br>GAGAGACAGAGACAGATCCATTCGATTAGTGAACGGATCCTTAGCA<br>CTTATCTGGGACGATCTGCGGAGCCTGTGCCTCTTCAGCTACCACC<br>GCTTGAGAGACTTACTCTTGATTGTAACGAGGATTGTGGAACTTCT<br>GGGACGCAGGGGTGGGAAGCCCTCAAATATTGGTGGAATCTCCTA<br>CAATATTGGAGTCAGGAGCTAAAGAATAG |
| 22 | CMV<br>Promoter | ACATTGATTATTGACTAGTTATTAATAGTAATCAATTACGGGGTCA<br>TTAGTTCATAGCCCATATATGGAGTTCCGCGTTACATAACTTACGG<br>TAAATGGCCCGCCTGGCTGACCGCCCAACGACCCCCGCCCATTGAC<br>GTCAATAATGACGTATGTTCCCATAGTAACGCCAATAGGGACTTTC<br>CATTGACGTCAATGGGTGGAGTATTTACGGTAAACTGCCCACTTGG<br>CAGTACATCAAGTGTATCATATGCCAAGTACGCCCCCTATTGACGT<br>CAATGACGGTAAATGGCCCGCCTGGCATTATGCCCAGTACATGACC<br>TTATGGGACTTTCCTACTTGGCAGTACATCTACGTATTAGTCATCG<br>CTATTACCATGGTGATGCGGTTTTGGCAGTACATCAATGGGCGTGG<br>ATAGCGGTTTGACTCACGGGGATTTCCAAGTCTCCACCCCATTGAC<br>GTCAATGGGAGTTTGTTTTGGCACCAAAATCAACGGGACTTTCCAA<br>AATGTCGTAACAACTCCGCCCCATTGACGCAAATGGGCGGTAGGCG<br>TGTACGGTGGGAGGTCTATATAAGC |

Sequence Listings

| SEQ ID NO: | Description | Sequence |
|---|---|---|
| 23 | VSV-G/DNA fragment containing VSV-G/ Envelope Glycoprotein | GAATTCATGAAGTGCCTTTTGTACTTAGCCTTTTTATTCATTGGGG<br>TGAATTGCAAGTTCACCATAGTTTTTCCACACAACCAAAAAGGAAA<br>CTGGAAAAATGTTCCTTCTAATTACCATTATTGCCCGTCAAGCTCA<br>GATTTAAATTGGCATAATGACTTAATAGGCACAGCCTTACAAGTCA<br>AAATGCCCAAGAGTCACAAGGCTATTCAAGCAGACGGTTGGATGTG<br>TCATGCTTCCAAATGGGTCACTACTTGTGATTTCCGCTGGTATGGA<br>CCGAAGTATATAACACATTCCATCCGATCCTTCACTCCATCTGTAG<br>AACAATGCAAGGAAAGCATTGAACAAACGAAACAAGGAACTTGGCT<br>GAATCCAGGCTTCCCTCCTCAAAGTTGTGGATATGCAACTGTGACG<br>GATGCCGAAGCAGTGATTGTCCAGGTGACTCCTCACCATGTGCTGG<br>TTGATGAATACACAGGAGAATGGGTTGATTCACAGTTCATCAACGG<br>AAAATGCAGCAATTACATATGCCCCACTGTCCATAACTCTACAACC<br>TGGCATTCTGACTATAAGGTCAAAGGGCTATGTGATTCTAACCTCA<br>TTTCCATGGACATCACCTTCTTCTCAGAGGACGGAGAGCTATCATC<br>CCTGGGAAAGGAGGGCACAGGGTTCAGAAGTAACTACTTTGCTTAT<br>GAAACTGGAGGCAAGGCCTGCAAAATGCAATACTGCAAGCATTGGG<br>GAGTCAGACTCCCATCAGGTGTCTGGTTCGAGATGGCTGATAAGGA<br>TCTCTTTGCTGCAGCCAGATTCCCTGAATGCCCAGAAGGGTCAAGT<br>ATCTCTGCTCCATCTCAGACCTCAGTGGATGTAAGTCTAATTCAGG<br>ACGTTGAGAGGATCTTGGATTATTCCCTCTGCCAAGAAACCTGGAG<br>CAAAATCAGAGCGGGTCTTCAATCTCTCCAGTGGATCTCAGCTAT<br>CTTGCTCCTAAAAACCCAGGAACCGGTCCTGCTTTCACCATAATCA<br>ATGGTACCCTAAAATACTTTGAGACCAGATACATCAGAGTCGATAT<br>TGCTGCTCCAATCCTCTCAAGAATGGTCGGAATGATCAGTGGAACT<br>ACCACAGAAAGGGAACTGTGGGATGACTGGGCACCATATGAAGACG<br>TGGAAATTGGACCCAATGGAGTTCTGAGGACCAGTTCAGGATATAA<br>GTTTCCTTTATACATGATTGGACATGGTATGTTGGACTCCGATCTT<br>CATCTTAGCTCAAAGGCTCAGGTGTTCGAACATCCTCACATTCAAG<br>ACGCTGCTTCGCAACTTCCTGATGATGAGAGTTTTATTTTTTGGTTA<br>TACTGGGCTATCCAAAAATCCAATCGAGCTTGTAGAAGGTTGGTTC<br>AGTAGTTGGAAAAGCTCTATTGCCTCTTTTTTCTTTATCATAGGGT<br>TAATCATTGGACTATTCTTGGTTCTCCGAGTTGGTATCCATCTTTG<br>CATTAAATTAAAGCACACCAAGAAAAGACAGATTTATACAGACATA<br>GAGATGAGAATTC |
| 24 | CAG enhancer | TAGTTATTAATAGTAATCAATTACGGGGTCATTAGTTCATAGCCCA<br>TATATGGAGTTCCGCGTTACATAACTTACGGTAAATGGCCCGCCTG<br>GCTGACCGCCCAACGACCCCCGCCCATTGACGTCAATAATGACGTA<br>TGTTCCCATAGTAACGCCAATAGGGACTTTCCATTGACGTCAATGG<br>GTGGACTATTTACGGTAAACTGCCCACTTGGCAGTACATCAAGTGT<br>ATCATATGCCAAGTACGCCCCCTATTGACGTCAATGACGGTAAATG<br>GCCCGCCTGGCATTATGCCCAGTACATGACCTTATGGGACTTTCCT<br>ACTTGGCAGTACATCTACGTATTAGTCATC |
| 25 | Chicken beta actin intron | GGAGTCGCTGCGTTGCCTTCGCCCCGTGCCCCGCTCCGCGCCGCCT<br>CGCGCCGCCCGCCCCGGCTCTGACTGACCGCGTTACTCCCACAGGT<br>GAGCGGGCGGGACGGCCCTTCTCCTCCGGGCTGTAATTAGCGCTTG<br>GTTTAATGACGGCTCGTTTCTTTTCTGTGGCTGCGTGAAAGCCTTA<br>AAGGGCTCCGGGAGGGCCCTTTGTGCGGGGGGAGCGGCTCGGGGG<br>GTGCGTGCGTGTGTGTGTGCGTGGGGAGCGCCGCGTGCGGCCCGCG<br>CTGCCCGGCGGCTGTGAGCGCTGCGGGCGCGGCGCGGGGCTTTGTG<br>CGCTCCGCGTGTGCGCGAGGGGAGCGCGGCCGGGGCGGTGCCCCG<br>CGGTGCGGGGGGGCTGCGAGGGGAACAAAGGCTGCGTGCGGGGTGT<br>GTGCGTGGGGGGGTGAGCAGGGGGTGTGGGCGCGGCGGTCGGGCTG<br>TAACCCCCCCCTGCACCCCCCTCCCCGAGTTGCTGAGCACGGCCCG<br>GCTTCGGGTGCGGGGCTCCGTGCGGGCGTGGCGCGGGGCTCGCCG<br>TGCCGGGCGGGGGTGGCGGCAGGTGGGGGTGCCGGGCGGGGCGGG<br>GCCGCCTCGGGCCGGGGAGGGCTCGGGGGAGGGGCGCGGCGGCCCC<br>GGAGCGCCGGCGGCTGTCGAGGCGCGGCGAGCCGCAGCCATTGCCT<br>TTTATGGTAATCGTGCGAGAGGGCGCAGGGACTTCCTTTGTCCCAA<br>ATCTGGCGGAGCCGAAATCTGGGAGGCGCCGCCGCACCCCCTCTAG<br>CGGGCGCGGGCGAAGCGGTGCGGCGCCGGCAGGAAGGAAATGGGCG<br>GGGAGGGCCTTCGTGCGTCGCCGCGCCGCCGTCCCCTTCTCCATCT<br>CCAGCCTCGGGGCTGCCGCAGGGGACGGCTGCCTTCGGGGGGGAC<br>GGGGCAGGGCGGGGTTCGGCTTCTGGCGTGTGACCGGCGG |
| 26 | Rabbit beta globin poly A | AGATCTTTTTCCCTCTGCCAAAAATTATGGGGACATCATGAAGCCC<br>CTTGAGCATCTGACTTCTGGCTAATAAAGGAAATTTATTTTCATTG<br>CAATAGTGTGTTGGAATTTTTTGTGTCTCTCACTCGGAAGGACATA<br>TGGGAGGGCAAATCATTTAAAACATCAGAATGAGTATTTGGTTTAG<br>AGTTTGGCAACATATGCCATATGCTGGCTGCCATGAACAAAGGTGG<br>CTATAAAGAGGTCATCAGTATATGAAACAGCCCCCTGCTGTCCATT<br>CCTTATTCCATAGAAAAGCCTTGACTTGAGGTTAGATTTTTTTAT<br>ATTTTGTTTTGTGTTATTTTTTCTTTAACATCCCTAAAATTTTCC |

| SEQ ID NO: | Description | Sequence |
|---|---|---|
| | | TTACATGTTTTACTAGCCAGATTTTTCCTCCTCTCCTGACTACTCC<br>CAGTCATAGCTGTCCCTCTTCTCTTATGAAGATC |
| 27 | Beta globin intron | GTGAGTTTGGGGACCCTTGATTGTTCTTTCTTTTTCGCTATTGTAA<br>AATTCATGTTATATGGAGGGGGCAAAGTTTTCAGGGTGTTGTTTAG<br>AATGGGAAGATGTCCCTTGTATCACCATGGACCCTCATGATAATTT<br>TGTTTCTTTCACTTTCTACTCTGTTGACAACCATTGTCTCCTCTTA<br>TTTTCTTTTCATTTTCTGTAACTTTTTCGTTAAACTTTAGCTTGCA<br>TTTGTAACGAATTTTTAAATTCACTTTTGTTTATTTGTCAGATTGT<br>AAGTACTTTCTCTAATCACTTTTTTTTCAAGGCAATCAGGGTATAT<br>TATATTGTACTTCAGCACAGTTTTAGAGAACAATTGTTATAATTAA<br>ATGATAAGGTAGAATATTTCTGCATATAAATTCTGGCTGGCGTGGA<br>AATATTCTTATTGGTAGAAACAACTACACCCTGGTCATCATCCTGC<br>CTTTCTCTTTATGGTTACAATGATATACACTGTTTGAGATGAGGAT<br>AAAATACTCTGAGTCCAAACCGGGCCCCTCTGCTAACCATGTTCAT<br>GCCTTCTTCTCTTTCCTACAG |
| 28 | Primer | TAAGCAGAATTCATGAATTTGCCAGGAAGAT |
| 29 | Primer | CCATACAATGAATGGACACTAGGCGGCCGCACGAAT |
| 30 | Gag, Pol, Integrase fragment | GAATTCATGAATTTGCCAGGAAGATGGAAACCAAAAATGATAGGGG<br>GAATTGGAGGTTTTATCAAAGTAAGACAGTATGATCAGATACTCAT<br>AGAAATCTGCGGACATAAAGCTATAGGTACAGTATTAGTAGGACCT<br>ACACCTGTCAACATAATTGGAAGAAATCTGTTGACTCAGATTGGCT<br>GCACTTTAAATTTTCCCATTAGTCCTATTGAGACTGTACCAGTAAA<br>ATTAAAGCCAGGAATGGATGGCCCAAAAGTTAAACAATGGCCATTG<br>ACAGAAGAAAAAATAAAAGCATTAGTAGAAATTTGTACAGAAATGG<br>AAAAGGAAGGAAAAATTTCAAAAATTGGGCCTGAAAATCCATACAA<br>TACTCCAGTATTTGCCATAAAGAAAAAAGACAGTACTAAATGGAGA<br>AAATTAGTAGATTTCAGAGAACTTAATAAGAGAACTCAAGATTTCT<br>GGGAAGTTCAATTAGGAATACCACATCCTGCAGGGTTAAAACAGAA<br>AAAATCAGTAACAGTACTGGATGTGGGCGATGCATATTTTTCAGTT<br>CCCTTAGATAAAGACTTCAGGAAGTATACTGCATTTACCATACCTA<br>GTATAAACAATGAGACACCAGGGATTAGATATCAGTACAATGTGCT<br>TCCACAGGGATGGAAAGGATCACCAGCAATATTCCAGTGTAGCATG<br>ACAAAAATCTTAGAGCCTTTTAGAAAACAAAATCCAGACATAGTCA<br>TCTATCAATACATGGATGATTTGTATGTAGGATCTGACTTAGAAAT<br>AGGGCAGCATAGAACAAAAATAGAGGAACTGAGACAACATCTGTTG<br>AGGTGGGGATTTACCACACCAGACAAAAAACATCAGAAAGAACCTC<br>CATTCCTTTGGATGGGTTATGAACTCCATCCTGATAAATGGACAGT<br>ACAGCCTATAGTGCTGCCAGAAAAGGACAGCTGGACTGTCAATGAC<br>ATACAGAAATTAGTGGGAAAATTGAATTGGGCAAGTCAGATTTATG<br>CAGGGATTAAAGTAAGGCAATTATGTAAACTTCTTAGGGGAACCAA<br>AGCACTAACAGAAGTAGTACCACTAACAGAAGAAGCAGAGCTAGAA<br>CTGGCAGAAAACAGGGAGATTCTAAAAGAACCGGTACATGGAGTGT<br>ATTATGACCCATCAAAAGACTTAATAGCAGAAATACAGAAGCAGGG<br>GCAAGGCCAATGGACATATCAAATTTATCAAGAGCCATTTAAAAAT<br>CTGAAAACAGGAAAGTATGCAAGAATGAAGGGTGCCCACACTAATG<br>ATGTGAAACAATTAACAGAGGCAGTACAAAAAATAGCCACAGAAAG<br>CATAGTAATATGGGGAAAGACTCCTAAATTTAAATTACCCATACAA<br>AAGGAAACATGGGAAGCATGGTGGACAGAGTATTGGCAAGCCACCT<br>GGATTCCTGAGTGGGAGTTTGTCAATACCCCTCCCTTAGTGAAGTT<br>ATGGTACCAGTTAGAGAAAGAACCCATAATAGGAGCAGAAACTTTC<br>TATGTAGATGGGGCAGCCAATAGGGAAACTAAATTAGGAAAAGCAG<br>GATATGTAACTGACAGAGGAAGACAAAAAGTTGTCCCCCTAACGGA<br>CACAACAAATCAGAAGACTGAGTTACAAGCAATTCATCTAGCTTTG<br>CAGGATTCGGGATTAGAAGTAAACATAGTGACAGACTCACAATATG<br>CATTGGGAATCATTCAAGCACAACCAGATAAGAGTGAATCAGAGTT<br>AGTCAGTCAAATAATAGAGCAGTTAATAAAAAAGGAAAAAGTCTAC<br>CTGGCATGGGTACCAGCACACAAAGGAATTGGAGGAAATGAACAAG<br>TAGATAAATTGGTCAGTGCTGGAATCAGGAAAGTACTATTTTTAGA<br>TGGAATAGATAAGGCCCAAGAAGAACATGAGAAATATCACAGTAAT<br>TGGAGAGCAATGGCTAGTGATTTTAACCTACCACCTGTAGTAGCAA<br>AAGAAATAGTAGCCAGCTGTGATAAATGTCAGCTAAAAGGGGAAGC<br>CATGCATGGACAAGTAGACTGTAGCCCAGGAATATGGCAGCTAGAT<br>TGTACACATTTAGAAGGAAAAGTTATCTTGGTAGCAGTTCATGTAG<br>CCAGTGGATATATAGAAGCAGAAGTAATTCCAGCAGAGACAGGGCA<br>AGAAACAGCATACTTCCTCTTAAAATTAGCAGGAAGATGGCCAGTA<br>AAAACAGTACATACAGACAATGGCAGCAATTTCACCAGTACTACAG<br>TTAAGGCCGCCTGTTGGTGGGCGGGATCAAGCAGGAATTTGGCAT<br>TCCCTACAATCCCCAAAGTCAAGGAGTAATAGAATCTATGAATAAA<br>GAATTAAAGAAAATTATAGGACAGGTAAGAGATCAGGCTGAACATC<br>TTAAGACAGCAGTACAAATGGCAGTATTCATCCACAATTTTAAAAG<br>AAAAGGGGGGATTGGGGGGTACAGTGCAGGGGAAAGAATAGTAGAC |

Sequence Listings

| SEQ ID NO: | Description | Sequence |
|---|---|---|
| | | ATAATAGCAACAGACATACAAACTAAAGAATTACAAAAACAAATTA<br>CAAAAATTCAAAATTTTCGGGTTTATTACAGGGACAGCAGAGATCC<br>AGTTTGGAAAGGACCAGCAAAGCTCCTCTGGAAAGGTGAAGGGGCA<br>GTAGTAATACAAGATAATAGTGACATAAAAGTAGTGCCAAGAAGAA<br>AAGCAAAGATCATCAGGGATTATGGAAAACAGATGGCAGGTGATGA<br>TTGTGTGGCAAGTAGACAGGATGAGGATTAA |
| 31 | DNA Fragment containing Rev, RRE and rabbit beta globin poly A | TCTAGAATGGCAGGAAGAAGCGGAGACAGCGACGAAGAGCTCATCA<br>GAACAGTCAGACTCATCAAGCTTCTCTATCAAAGCAACCCACCTCC<br>CAATCCCGAGGGGACCCGACAGGCCCGAAGGAATAGAAGAAGAAGG<br>TGGAGAGAGAGACAGAGACAGATCCATTCGATTAGTGAACGGATCC<br>TTGGCACTTATCTGGGACGATCTGCGGAGCCTGTGCCTCTTCAGCT<br>ACCACCGCTTGAGAGACTTACTCTTGATTGTAACGAGGATTGTGGA<br>ACTTCTGGGACGCAGGGGGTGGGAAGCCCTCAAATATTGGTGGAAT<br>CTCCTACAATATTGGAGTCAGGAGCTAAAGAATAGAGGAGCTTTGT<br>TCCTTGGGTTCTTGGGAGCAGCAGGAAGCACTATGGGCGCAGCGTC<br>AATGACGCTGACGGTACAGGCCAGACAATTATTGTCTGGTATAGTG<br>CAGCAGCAGAACAATTTGCTGAGGGCTATTGAGGCGCAACAGCATC<br>TGTTGCAACTCACAGTCTGGGGCATCAAGCAGCTCCAGGCAAGAAT<br>CCTGGCTGTGGAAAGATACCTAAAGGATCAACAGCTCCTAGATCTT<br>TTTCCCTCTGCCAAAAATTATGGGGACATCATGAAGCCCCTTGAGC<br>ATCTGACTTCTGGCTAATAAAGGAAATTTATTTTCATTGCAATAGT<br>GTGTTGGAATTTTTTGTGTCTCTCACTCGGAAGGACATATGGGAGG<br>GCAAATCATTTAAAACATCAGAATGAGTATTTGGTTTAGAGTTTGG<br>CAACATATGCCATATGCTGGCTGCCATGAACAAAGGTGGCTATAAA<br>GAGGTCATCAGTATATGAAACAGCCCCCTGCTGTCCATTCCTTATT<br>CCATAGAAAAGCCTTGACTTGAGGTTAGATTTTTTTTATATTTTGT<br>TTTGTGTTATTTTTTCTTTAACATCCCTAAAATTTTCCTTACATG<br>TTTTACTAGCCAGATTTTTCCTCCTCTCCTGACTACTCCCAGTCAT<br>AGCTGTCCCTCTTCTCTTATGAAGATCCCTCGACCTGCAGCCCAAG<br>CTTGGCGTAATCATGGTCATAGCTGTTTCCTGTGTGAAATTGTTAT<br>CCGCTCACAATTCCACACAACATACGAGCCGGAAGCATAAAGTGTA<br>AAGCCTGGGGTGCCTAATGAGTGAGCTAACTCACATTAATTGCGTT<br>GCGCTCACTGCCCGCTTTCCAGTCGGGAAACCTGTCGTGCCAGCGG<br>ATCCGCATCTCAATTAGTCAGCAACCATAGTCCCGCCCCTAACTCC<br>GCCCATCCCGCCCCTAACTCCGCCCAGTTCCGCCCATTCTCCGCCC<br>CATGGCTGACTAATTTTTTTATTTATGCAGAGGCCGAGGCCGCCT<br>CGGCCTCTGAGCTATTCCAGAAGTAGTGAGGAGGCTTTTTTGGAGG<br>CCTAGGCTTTTGCAAAAAGCTAACTTGTTTATTGCAGCTTATAATG<br>GTTACAAATAAAGCAATAGCATCACAAATTTCACAAATAAAGCATT<br>TTTTTCACTGCATTCTAGTTGTGGTTTGTCCAAACTCATCAATGTA<br>TCTTATCAGCGGCCGCCCCGGG |
| 32 | DNA fragment containing the CAG enhancer/ promoter/ intron sequence | ACGCGTTAGTTATTAATAGTAATCAATTACGGGGTCATTAGTTCAT<br>AGCCCATATATGGAGTTCCGCGTTACATAACTTACGGTAAATGGCC<br>CGCCTGGCTGACCGCCCAACGACCCCCGCCCATTGACGTCAATAAT<br>GACGTATGTTCCCATAGTAACGCCAATAGGGACTTTCCATTGACGT<br>CAATGGGTGGACTATTTACGGTAAACTGCCCACTTGGCAGTACATC<br>AAGTGTATCATATGCCAAGTACGCCCCCTATTGACGTCAATGACGG<br>TAAATGGCCCGCCTGGCATTATGCCCAGTACATGACCTTATGGGAC<br>TTTCCTACTTGGCAGTACATCTACGTATTAGTCATCGCTATTACCA<br>TGGGTCGAGGTGAGCCCCACGTTCTGCTTCACTCTCCCCATCTCCC<br>CCCCCTCCCCACCCCCAATTTTGTATTTATTTATTTTTAATTATT<br>TTGTGCAGCGATGGGGGCGGGGGGGGGGGGGCGCGCGCCAGGCGG<br>GGCGGGGCGGGGCGAGGGGCGGGGCGGGGCGAGGCGGAGAGGTGCG<br>GCGGCAGCCAATCAGAGCGGCGCGCTCCGAAAGTTTCCTTTTATGG<br>CGAGGCGGCGGCGGCGGCGGCCCTATAAAAAGCGAAGCGCGCGGCG<br>GGCGGGAGTCGCTGCGTTGCCTTCGCCCCGTGCCCCGCTCCGCGCC<br>GCCTCGCGCCGCCCGCCCCGGCTCTGACTGACCGCGTTACTCCCAC<br>AGGTGAGCGGGCGGGACGGCCCTTCTCCTCCGGGCTGTAATTAGCG<br>CTTGGTTTAATGACGGCTCGTTTCTTTTCTGTGGCTGCGTGAAAGC<br>CTTAAAGGGCTCCGGGAGGGCCCTTTGTGCGGGGGGAGCGGCTCG<br>GGGGGTGCGTGCGTGTGTGTGCGTGGGGAGCGCCGCGTGCGGCC<br>CGCGCTGCCCGGCGGCTGTGAGCGCTGCGGGCGCGGCGCGGGGCTT<br>TGTGCGCTCCGCGTGTGCGCGAGGGGAGCGCGGCCGGGGCGGTGC<br>CCCGCGGTGCGGGGGGCTGCGAGGGGAACAAAGGCTGCGTGCGGG<br>GTGTGTGCGTGGGGGGGTGAGCAGGGGGTGTGGGCGCGGCGGTCGG<br>GCTGTAACCCCCCCTGCACCCCCCTCCCCGAGTTGCTGAGCACGG<br>CCCGGCTTCGGGTGCGGGGCTCCGTGCGGGGCGTGGCGCGGGGCTC<br>GCCGTGCCGGGCGGGGGTGGCGGCAGGTGGGGGTGCCGGGCGGGG<br>CGGGGCCGCCTCGGGCCGGGGAGGGCTCGGGGAGGGGCGCGGCGG<br>CCCCGGAGCGCCGGCGGCTGTCGAGGCGCGGCGAGCCGCAGCCATT<br>GCCTTTTATGGTAATCGTGCGAGAGGGCGCAGGGACTTCCTTTGTC<br>CCAAATCTGGCGGAGCCGAAATCTGGGAGGCGCCGCCGCACCCCCT<br>CTAGCGGGCGCGGGCGAAGCGGTGCGGCGCCGGCAGGAAGGAAATG |

| SEQ ID NO: | Description | Sequence |
|---|---|---|
| | | GGCGGGGAGGGCCTTCGTGCGTCGCCGCGCCGCCGTCCCCTTCTCC ATCTCCAGCCTCGGGGCTGCCGCAGGGGGACGGCTGCCTTCGGGGG GGACGGGGCAGGGCGGGGTTCGGCTTCTGGCGTGTGACCGGCGGGA ATTC |
| 33 | RSV promoter and HIV Rev | CAATTGCGATGTACGGGCCAGATATACGCGTATCTGAGGGGACTAG GGTGTGTTTAGGCGAAAAGCGGGGCTTCGGTTGTACGCGGTTAGGA GTCCCCTCAGGATATAGTAGTTTCGCTTTTGCATAGGGAGGGGGAA ATGTAGTCTTATGCAATACACTTGTAGTCTTGCAACATGGTAACGA TGAGTTAGCAACATGCCTTACAAGGAGAGAAAAAGCACCGTGCATG CCGATTGGTGGAAGTAAGGTGGTACGATCGTGCCTTATTAGGAAGG CAACAGACAGGTCTGACATGGATTGGACGAACCACTGAATTCCGCA TTGCAGAGATAATTGTATTTAAGTGCCTAGCTCGATACAATAAACG CCATTTGACCATTCACCACATTGGTGTGCACCTCCAAGCTCGAGCT CGTTTAGTGAACCGTCAGATCGCCTGGAGACGCCATCCACGCTGTT TTGACCTCCATAGAAGACACCGGGACCGATCCAGCCTCCCCTCGAA GCTAGCGATTAGGCATCTCCTATGGCAGGAAGAAGCGGGAGACAGCG ACGAAGAACTCCTCAAGGCAGTCAGACTCATCAAGTTTCTCTATCA AAGCAACCCACCTCCCAATCCCGAGGGGACCCGACAGGCCCGAAGG AATAGAAGAAGGTGGAGAGAGAGACAGAGACAGATCCATTCGA TTAGTGAACGGATCCTTAGCACTTATCTGGGACGATCTGCGGAGCC TGTGCCTCTTCAGCTACCACCGCTTGAGAGACTTACTCTTGATTGT AACGAGGATTGTGGAACTTCTGGGACGCAGGGGGTGGGAAGCCCTC AAATATTGGTGGAATCTCCTACAATATTGGAGTCAGGAGCTAAAGA ATAGTCTAGA |
| 34 | Elongation Factor-1 alpha (EF1-alpha) promoter | CCGGTGCCTAGAGAAGGTGGCGCGGGGTAAACTGGGAAAGTGATGT CGTGTACTGGCTCCGCCTTTTTCCCGAGGGTGGGGGAGAACCGTAT ATAAGTGCAGTAGTCGCCGTGAACGTTCTTTTTCGCAACGGGTTTG CCGCCAGAACACAGGTAAGTGCCGTGTGTGGTTCCCGCGGGCCTGG CCTCTTTACGGGTTATGGCCCTTGCGTGCCTTGAATTACTTCCACG CCCCTGGCTGCAGTACGTGATTCTTGATCCCGAGCTTCGGGTTGGA AGTGGGTGGGAGAGTTCGAGGCCTTGCGCTTAAGGAGCCCCTTCGC CTCGTGCTTGAGTTGAGGCCTGGCCTGGGCGCTGGGGCCGCCGCGT GCGAATCTGGTGGCACCTTCGCGCCTGTCTCGCTGCTTTCGATAAG TCTCTAGCCATTTAAAATTTTTGATGACCTGCTGCGACGCTTTTTT TCTGGCAAGATAGTCTTGTAAATGCGGGCCAAGATCTGCACACTGG TATTTCGGTTTTTGGGGCCGCGGGCGGCGACGGGCCCGTGCGTCC CAGCGCACATGTTCGGCGAGGCGGGGCCTGCGAGCGCGGCCACCGA GAATCGGACGGGGGTAGTCTCAAGCTGGCCGGCCTGCTCTGGTGCC TGGCCTCGCGCCGCCGTGTATCGCCCCGCCCTGGGCGGCAAGGCTG GCCCGGTCGGCACCAGTTGCGTGAGCGGAAAGATGGCCGCTTCCCG GCCCTGCTGCAGGGAGCTCAAAATGGAGGACGCGGCGCTCGGGAGA GCGGGCGGGTGAGTCACCCACACAAAGGAAAAGGGCCTTTCCGTCC TCAGCCGTCGCTTCATGTGACTCCACGGAGTACCGGGCGCCGTCCA GGCACCTCGATTAGTTCTCGAGCTTTTGGAGTACGTCGTCTTTAGG TTGGGGGGAGGGGTTTTATGCGATGGAGTTTCCCCACACTGAGTGG GTGGAGACTGAAGTTAGGCCAGCTTGGCACTTGATGTAATTCTCCT TGGAATTTGCCCTTTTTGAGTTTGGATCTTGGTTCATTCTCAAGCC TCAGACAGTGGTTCAAAGTTTTTTTCTTCCATTTCAGGTGTCGTGA |
| 35 | Promoter; PGK | GGGGTTGGGGTTGCGCCTTTTCCAAGGCAGCCCTGGGTTTGCGCAG GACGCGGCTGCTCTGGGCGTGGTTCCGGGAAACGCAGCGGCGCCG ACCCTGGGTCTCGCACATTCTTCACGTCCGTTCGCAGCGTCACCCG GATCTTCGCCGCTACCCTTGTGGGCCCCCCGGCGACGCTTCCTGCT CCGCCCCTAAGTCGGGAAGGTTCCTTGCGGTTCGCGGCGTGCCGGA CGTGACAAACGGAAGCCGCACGTCTCACTAGTACCCTCGCAGACGG ACAGCGCCAGGGAGCAATGGCAGCGCGCCGACCGCGATGGGCTGTG GCCAATAGCGGCTGCTCAGCAGGGCGCGCCGAGAGCAGCGGCCGGG AAGGGGCGGTGCGGGAGGCGGGGTGTGGGCGGTAGTGTGGGCCCT GTTCCTGCCCGCGCGGTGTTCCGCATTCTGCAAGCCTCCGGAGCGC ACGTCGGCAGTCGGCTCCCTCGTTGACCGAATCACCGACCTCTCTC CCCAG |
| 36 | Promoter; UbC | GCGCCGGGTTTTGGCGCCTCCCGCGGGCGCCCCCCTCCTCACGGCG AGCGCTGCCACGTCAGACGAAGGGCGCAGGAGCGTTCCTGATCCTT CCGCCCGGACGCTCAGGACAGCGGCCCGCTGCTCATAAGACTCGGC CTTAGAACCCCAGTATCAGCAGAAGGACATTTTAGGACGGGACTTG GGTGACTCTAGGGCACTGGTTTTCTTTCCAGAGAGCGGAACAGGCG AGGAAAAGTAGTCCCTTCTCGGCGATTCTGCGGAGGGATCTCCGTG GGGCGGTGAACGCCGATGATTATATAAGGACGCGCCGGGTGTGGCA CAGCTAGTTCCGTCGCAGCCGGGATTTGGGTCGCGGTTCTTGTTTG TGGATCGCTGTGATCGTCACTTGGTGAGTTGCGGGCTGCTGGGCTG GCCGGGGCTTTCGTGGCCGCCGGGCCGCTCGGTGGACGGAAGCGT GTGGAGAGACCGCCAAGGGCTGTAGTCTGGGTCCGCGAGCAAGGTT |

| SEQ ID NO: | Description | Sequence |
|---|---|---|
| | | GCCCTGAACTGGGGGTTGGGGGGAGCGCACAAAATGGCGGCTGTTC<br>CCGAGTCTTGAATGGAAGACGCTTGTAAGGCGGGCTGTGAGGTCGT<br>TGAAACAAGGTGGGGGGCATGGTGGGCGGCAAGAACCCAAGGTCTT<br>GAGGCCTTCGCTAATGCGGGAAAGCTCTTATTCGGGTGAGATGGGC<br>TGGGGCACCATCTGGGGACCCTGACGTGAAGTTTGTCACTGACTGG<br>AGAACTCGGGTTTGTCGTCTGGTTGCGGGGCGGCAGTTATGCGGT<br>GCCGTTGGGCAGTGCACCCGTACCTTTGGGAGCGCGCGCCTCGTCG<br>TGTCGTGACGTCACCCGTTCTGTTGGCTTATAATGCAGGGTGGGGC<br>CACCTGCCGGTAGGTGTGCGGTAGGCTTTTCTCCGTCGCAGGACGC<br>AGGGTTCGGGCCTAGGGTAGGCTCTCCTGAATCGACAGGCGCCGGA<br>CCTCTGGTGAGGGGAGGGATAAGTGAGGCGTCAGTTTCTTTGGTCG<br>GTTTTATGTACCTATCTTCTTAAGTAGCTGAAGCTCCGGTTTTGAA<br>CTATGCGCTCGGGGTTGGCGAGTGTGTTTTGTGAAGTTTTTTAGGC<br>ACCTTTTGAAATGTAATCATTTGGGTCAATATGTAATTTTCAGTGT<br>TAGACTAGTAAA |
| 37 | Poly A; SV40 | GTTTATTGCAGCTTATAATGGTTACAAATAAAGCAATAGCATCACA<br>AATTTCACAAATAAAGCATTTTTTTCACTGCATTCTAGTTGTGGTT<br>TGTCCAAACTCATCAATGTATCTTATCA |
| 38 | Poly A; bGH | GACTGTGCCTTCTAGTTGCCAGCCATCTGTTGTTTGCCCCTCCCCC<br>GTGCCTTCCTTGACCCTGGAAGGTGCCACTCCCACTGTCCTTTCCT<br>AATAAAATGAGGAAATTGCATCGCATTGTCTGAGTAGGTGTCATTC<br>TATTCTGGGGGGTGGGGTGGGGCAGGACAGCAAGGGGGAGGATTGG<br>GAAGACAATAGCAGGCATGCTGGGGATGCGGTGGGCTCTATGG |
| 39 | Envelope;<br>RD114 | ATGAAACTCCCAACAGGAATGGTCATTTTATGTAGCCTAATAATAG<br>TTCGGGCAGGGTTTGACGACCCCGCAAGGCTATCGCATTAGTACA<br>AAAACAACATGGTAAACCATGCGAATGCAGCGGAGGGCAGGTATCC<br>GAGGCCCCACCGAACTCCATCCAACAGGTAACTTGCCCAGGCAAGA<br>CGGCCTACTTAATGACCAACCAAAAATGGAAATGCAGAGTCACTCC<br>AAAAAAATCTCACCCCTAGCGGGGGAGAACTCCAGAACTGCCCCTGT<br>AACACTTTCCAGGACTCGATGCACAGTTCTTGTTATACTGAATACC<br>GGCAATGCAGGGCGAATAATAAGACATACTACACGGCCACCTTGCT<br>TAAAATACGGTCTGGGAGCCTCAACGAGGTACAGATATTACAAAAC<br>CCCAATCAGCTCCTACAGTCCCCTTGTAGGGGCTCTATAAATCAGC<br>CCGTTTGCTGGAGTGCCACAGCCCCCATCCATATCTCCGATGGTGG<br>AGGACCCCTCGATACTAAGAGAGTGTGGACAGTCCAAAAAAGGCTA<br>GAACAAATTCATAAGGCTATGCATCCTGAACTTCAATACCACCCCT<br>TAGCCCCTGCCCAAAGTCAGAGATGACCTTAGCCTTGATGCACGGAC<br>TTTTGATATCCTGAATACCACTTTTAGGTTACTCCAGATGTCCAAT<br>TTTTAGCCTTGCCCAAGATTGTTGGCTCTGTTTAAAACTAGGTACCC<br>CTACCCCTCTTGCGATACCCACTCCCTCTTTAACCTACTCCCTAGC<br>AGACTCCCTAGCGAATGCCTCCTGTCAGATTATACCTCCCCTCTTG<br>GTTCAACCGATGCAGTTCTCCAACTCGTCCTGTTTATCTTCCCCTT<br>TCATTAACGATACGGAACAAATAGACTTAGGTGCAGTCACCTTTAC<br>TAACTGCACCTCTGTAGCCAATGTCAGTAGTCCTTTATGTGCCCTA<br>AACGGGTCAGTCTTCCTCTGTGGAAATAACATGGCATACACCTATT<br>TACCCCAAAACTGGACAGGACTTTGCGTCCAAGCCTCCCTCCTCCC<br>CGACATTGACATCATCCCGGGGGATGAGCCAGTCCCCATTCCTGCC<br>ATTGATCATTATATACATAGACCTAAACGAGCTGTACAGTTCATCC<br>CTTTACTAGCTGGACTGGGAATCACCGCAGCATTCACCACCGGAGC<br>TACAGGCCTAGGTGTCTCCGTCACCCAGTATACAAAATTATCCCAT<br>CAGTTAATATCTGATGTCCAAGTCTTATCCGGTACCATACAAGATT<br>TACAAGACCAGGTAGACTCGTTAGCTGAAGTAGTTCTCCAAAATAG<br>GAGGGGACTGGACCTACTAACGGCAGAACAAGGAGGAATTTGTTTA<br>GCCTTACAAGAAAATGCTGTTTTTATGCTAACAAGTCAGGAATTG<br>TGAGAACAAAATAAGAACCCTACAAGAAGAATTACAAAAACGCAG<br>GGAAAGCCTGGCATCCAACCCTCTCTGGACCGGGCTGCAGGGCTTT<br>CTTCCGTACCTCCTACCTCTCCTGGGACCCCTACTCACCCTCCTAC<br>TCATACTAACCATTGGGCCATGCGTTTTCAATCGATTGGTCCAATT<br>TGTTAAAGACAGGATCTCAGTGGTCAGGCTCTGGTTTTGACTCAG<br>CAATATCACCAGCTAAAACCCATAGAGTACGAGCCATGA |
| 40 | Envelope;<br>GALV | ATGCTTCTCACCTCAAGCCCGCACCACCTTCGGCACCAGATGAGTC<br>CTGGGAGCTGGAAAAGACTGATCATCCTCTTAAGCTGCGTATTCGG<br>AGACGGCAAAACGAGTCTGCAGAATAAGAACCCCCACCAGCCTGTG<br>ACCCTCACCTGGCAGGTACTGTCCCAAACTGGGGACGTTGTCTGGG<br>ACAAAAAGGCAGTCCAGCCCCTTTGGACTTGGTGGCCCTCTCTTAC<br>ACCTGATGTATGTGCCCTGGCGGCCGGTCTTGAGTCCTGGGATATC<br>CCGGGATCCGATGTATCGTCCTCTAAAAGAGTTAGACCTCCTGATT<br>CAGACTATACTGCCGCTTATAAGCAAATCACCTGGGGAGCCATAGG<br>GTGCAGCTACCCTCGGGCTAGGACCAGGATGGCAAATTCCCCCTTC<br>TACGTGTGTCCCCGAGCTGGCCGAACCCATTCAGAAGCTAGGAGGT<br>GTGGGGGGCTAGAATCCCTATACTGTAAAGAATGGAGTTGTGAGAC |

-continued

Sequence Listings

| SEQ ID NO: | Description | Sequence |
|---|---|---|
| | | CACGGGTACCGTTTATTGGCAACCCAAGTCCTCATGGGACCTCATA<br>ACTGTAAAATGGGACCAAAATGTGAAATGGGAGCAAAAATTTCAAA<br>AGTGTGAACAAACCGGCTGGTGTAACCCCCTCAAGATAGACTTCAC<br>AGAAAAAGGAAAACTCTCCAGAGATTGGATAACGGAAAAAACCTGG<br>GAATTAAGGTTCTATGTATATGGACACCCAGGCATACAGTTGACTA<br>TCCGCTTAGAGGTCACTAACATGCCGGTTGTGGCAGTGGGCCCAGA<br>CCCTGTCCTTGCGGAACAGGGACCTCCTAGCAAGCCCCTCACTCTC<br>CCTCTCTCCCCACGGAAAGCGCCGCCCACCCCTCTACCCCCGGCGG<br>CTAGTGAGCAAACCCCTGCGGTGCATGGAGAAACTGTTACCCTAAA<br>CTCTCCGCCTCCCACCAGTGGCGACCGACTCTTTGGCCTTGTGCAG<br>GGGGCCTTCCTAACCTTGAATGCTACCAACCCAGGGGCCACTAAGT<br>CTTGCTGGCTCTGTTTGGGCATGAGCCCCCCTTATTATGAAGGGAT<br>AGCCTCTTCAGGAGAGGTCGCTTATACCTCCAACCATACCCGATGC<br>CACTGGGGGGCCCAAGGAAAGCTTACCCTCACTGAGGTCTCCGGAC<br>TCGGGTCATGCATAGGGAAGGTGCCTCTTACCCATCAACATCTTTG<br>CAACCAGACCTTACCCATCAATTCCTCTAAAAACCATCAGTATCTG<br>CTCCCCTCAAACCATAGCTGGTGGGCCTGCAGCACTGGCCTCACCC<br>CCTGCCTCTCCACCTCAGTTTTTAATCAGTCTAAAGACTTCTGTGT<br>CCAGGTCCAGCTGATCCCCCGCATCTATTACCATTCTGAAGAAACC<br>TTGTTACAAGCCTATGACAAATCACCCCCCAGGTTTAAAAGAGAGC<br>CTGCCTCACTTACCCTAGCTGTCTTCCTGGGGTTAGGGATTGCGGC<br>AGGTATAGGTACTGGCTCAACCGCCCTAATTAAAGGGCCCATAGAC<br>CTCCAGCAAGGCCTAACCAGCCTCCAAATCGCCATTGACGCTGACC<br>TCCGGGCCCTTCAGGACTCAATCAGCAAGCTAGAGGACTCACTGAC<br>TTCCCTATCTGAGGTAGTACTCCAAAATAGGAGAGGCCTTGACTTA<br>CTATTCCTTAAAGAAGGAGGCCTCTGCGCGGCCCTAAAAGAAGAGT<br>GCTGTTTTTATGTAGACCACTCAGGTGCAGTACGAGACTCCATGAA<br>AAAACTTAAAGAAAGACTAGATAAAAGACAGTTAGAGCGCCAGAAA<br>AACCAAAACTGGTATGAAGGGTGGTTCAATAACTCCCCTTGGTTTA<br>CTACCCTACTATCAACCATCGCTGGGCCCCTATTGCTCCTCCTTTT<br>GTTACTCACTCTTGGGCCCTGCATCATCAATAAATTAATCCAATTC<br>ATCAATGATAGGATAAGTGCAGTCAAAATTTTAGTCCTTAGACAGA<br>AATATCAGACCCTAGATAACGAGGAAAACCTTTAA |
| 41 | Envelope;<br>FUG | ATGGTTCCGCAGGTTCTTTTGTTTGTACTCCTTCTGGGTTTTTCGT<br>TGTGTTTCGGGAAGTTCCCCATTTACACGATACCAGACGAACTTGG<br>TCCCTGGAGCCCTATTGACATACACCATCTCAGCTGTCCAAATAAC<br>CTGGTTGTGGAGGATGAAGGATGTACCAACCTGTCCGAGTTCTCCT<br>ACATGGAACTCAAAGTGGGATACATCTCAGCCATCAAAGTGAACGG<br>GTTCACTTGCACAGGTGTTGTGACAGAGGCAGAGACCTACACCAAC<br>TTTGTTGGTTATGTCACAACCACATTCAAGAGAAAGCATTTCCGCC<br>CCACCCCAGACGCATGTAGAGCCGCGTATAACTGGAAGATGGCCGG<br>TGACCCCAGATATGAAGAGTCCCTACACAATCCATACCCCGACTAC<br>CACTGGCTTCGAACTGTAAGAACCACCAAAGAGTCCCTCATTATCA<br>TATCCCCAAGTGTGACAGATTTGGACCCATATGACAAATCCCTTCA<br>CTCAAGGGTCTTCCCTGGCGGAAAGTGCTCAGGAATAACGGTGTCC<br>TCTACCTACTGCTCAACTAACCATGATTACACCATTTGGATGCCCG<br>AGAATCCGAGACCAAGGACACCTTGTGACATTTTTACCAATAGCAG<br>AGGGAAGAGAGCATCCAACGGGAACAAGACTTGCGGCTTTGTGGAT<br>GAAAGAGGCCTGTATAAGTCTCTAAAAGGAGCATGCAGGCTCAAGT<br>TATGTGGAGTTCTTGGACTTAGACTTATGGATGGAACATGGGTCGC<br>GATGCAAACATCAGATGAGACCAAATGGTGCCCTCCAGATCAGTTG<br>GTGAATTTGCACGACTTTCGCTCAGACGAGATCGAGCATCTCGTTG<br>TGGAGGAGTTAGTTAAGAAAAGAGAGGAATGTCTGGATGCATTAGA<br>GTCCATCATGACCACCAAGTCAGTAAGTTTCAGACGTCTCAGTCAC<br>CTGAGAAAACTTGTCCCAGGGTTTGGAAAAGCATATACCATATTCA<br>ACAAAACCTTGATGGAGGCTGATGCTCACTACAAGTCAGTCCGGAC<br>CTGGAATGAGATCATCCCCTCAAAAGGGTGTTTGAAAGTTGGAGGA<br>AGGTGCCATCCTCATGTGAACGGGGTGTTTTTCAATGGTATAATAT<br>TAGGGCCTGACGACCATGTCCTAATCCCAGAGATGCAATCATCCCT<br>CCTCCAGCAACATATGGAGTTGTTGGAATCTTCAGTTATCCCCCTG<br>ATGCACCCCCTGGCAGACCCTTCTACAGTTTTCAAAGAAGGTGATG<br>AGGCTGAGGATTTTGTTGAAGTTCACCTCCCCGATGTGTACAAACA<br>GATCTCAGGGGTTGACCTGGGTCTCCCGAACTGGGGAAAGTATGTA<br>TTGATGACTGCAGGGGCCATGATTGGCCTGGTGTTGATATTTTCCC<br>TAATGACATGGTGCAGAGTTGGTATCCATCTTTGCATTAAATTAAA<br>GCACACCAAGAAAAGACAGATTTATACAGACATAGAGATGAACCGA<br>CTTGGAAAGTAA |
| 42 | Envelope;<br>LCMV | ATGGGTCAGATTGTGACAATGTTTGAGGCTCTGCCTCACATCATCG<br>ATGAGGTGATCAACATTGTCATTATTGTGCTTATCGTGATCACGGG<br>TATCAAGGCTGTCTACAATTTTGCCACCTGTGGGATATTCGCATTG<br>ATCAGTTTCCTACTTCTGGCTGGCAGGTCCTGTGGCATGTACGGTC<br>TTAAGGGACCCGACATTTACAAAGGAGTTTACCAATTTAAGTCAGT<br>GGAGTTTGATATGTCACATCTGAACCTGACCATGCCCAACGCATGT |

| SEQ ID NO: | Description | Sequence |
|---|---|---|
| | | TCAGCCAACAACTCCCACCATTACATCAGTATGGGGACTTCTGGAC
TAGAATTGACCTTCACCAATGATTCCATCATCAGTCACAACTTTTG
CAATCTGACCTCTGCCTTCAACAAAAAGACCTTTGACCACACACTC
ATGAGTATAGTTTCGAGCCTACACCTCAGTATCAGAGGGAACTCCA
ACTATAAGGCAGTATCCTGCGACTTCAACAATGGCATAACCATCCA
ATACAACTTGACATTCTCAGATCGACAAAGTGCTCAGAGCCAGTGT
AGAACCTTCAGAGGTAGAGTCCTAGATATGTTTAGAACTGCCTTCG
GGGGGAAATACATGAGGAGTGGCTGGGGCTGGACAGGCTCAGATGG
CAAGACCACCTGGTGTAGCCAGACGAGTTACCAATACCTGATTATA
CAAAATAGAACCTGGGAAAACCACTGCACATATGCAGGTCCTTTTG
GGATGTCCAGGATTCTCCTTTCCCAAGAGAAGACTAAGTTCTTCAC
TAGGAGACTAGCGGGCACATTCACCTGGACTTTGTCAGACTCTTCA
GGGGTGGAGAATCCAGGTGGTTATTGCCTGACCAAATGGATGATTC
TTGCTGCAGAGCTTAAGTGTTTCGGGAACACAGCAGTTGCGAAATG
CAATGTAAATCATGATGCCGAATTCTGTGACATGCTGCGACTAATT
GACTACAACAAGGCTGCTTTGAGTAAGTTCAAAGAGGACGTAGAAT
CTGCCTTGCACTTATTCAAAACAACAGTGAATTCTTTGATTTCAGA
TCAACTACTGATGAGGAACCACTTGAGAGATCTGATGGGGTGCCA
TATTGCAATTACTCAAAGTTTTGGTACCTAGAACATGCAAAGACCG
GCGAAACTAGTGTCCCCAAGTGCTGGCTTGTCACCAATGGTTCTTA
CTTAAATGAGACCCACTTCAGTGATCAAATCGAACAGGAAGCCGAT
AACATGATTACAGAGATGTTGAGGAAGGATTACATAAAGAGGCAGG
GGAGTACCCCCCTAGCATTGATGGACCTTCTGATGTTTTCCACATC
TGCATATCTAGTCAGCATCTTCCTGCACCTTGTCAAAATACCAACA
CACAGGCACATAAAAGGTGGCTCATGTCCAAAGCCACACCGATTAA
CCAACAAAGGAATTTGTAGTTGTGGTGCATTTAAGGTGCCTGGTGT
AAAAACCGTCTGGAAAAGACGCTGA |
| 43 | Envelope;
FPV | ATGAACACTCAAATCCTGGTTTTCGCCCTTGTGGCAGTCATCCCCA
CAAATGCAGACAAAATTTGTCTTGGACATCATGCTGTATCAAATGG
CACCAAAGTAAACACACTCACTGAGAGAGGAGTAGAAGTTGTCAAT
GCAACGGAAACAGTGGAGCGGACAAACATCCCCAAAATTTGCTCAA
AAGGGAAAAGAACCACTGATCTTGGCCAATGCGGACTGTTAGGGAC
CATTACCGGACCACCTCAATGCGACCAATTTCTAGAATTTTCAGCT
GATCTAATAATCGAGAGACGAGAAGGAAATGATGTTTGTTACCCGG
GGAAGTTTGTTAATGAAGAGGCATTGCGACAAATCCTCAGAGGATC
AGGTGGGATTGACAAAGAAACAATGGGATTCACATATAGTGGAATA
AGGACCAACGGAACAACTAGTGCATGTAGAAGATCAGGGTCTTCAT
TCTATGCAGAAATGGAGTGGCTCCTGTCAAATACAGACAATGCTGC
TTTCCCACAAATGACAAAATCATACAAAAACACAAGGAGAGAATCA
GCTCTGATAGTCTGGGGAATCCACCATTCAGGATCAACCACCGAAC
AGACCAAACTATATGGGAGTGGAAATAAACTGATAACAGTCGGGAG
TTCCAAATATCATCAATCTTTTGTGCCGAGTCCAGGAACACGACCG
CAGATAAATGGCCAGTCCGGACGGATTGATTTTCATTGGTTGATCT
TGGATCCCAATGATACAGTTACTTTTAGTTTCAATGGGGCTTTCAT
AGCTCCAAATCGTGCCAGCTTCTTGAGGGGAAAGTCCATGGGGATC
CAGAGCGATGTGCAGGTTGATGCCAATTGCGAAGGGGAATGCTACC
ACAGTGGAGGGACTATAACAAGCAGATTGCCTTTTCAAAACATCAA
TAGCAGAGCAGTTGGCAAATGCCCAAGATATGTAAAACAGGAAAGT
TTATTATTGGCAACTGGGATGAAGAACGTTCCCGAACCTTCCAAAA
AAAGGAAAAAAAGAGGCCTGTTTGGCGCTATAGCAGGGTTTATTGA
AAATGGTTGGGAAGGTCTGGTCGACGGGTGGTACGGTTTCAGGCAT
CAGAATGCACAAGGAGAAGGAACTGCAGCAGACTACAAAAGCACCC
AATCGGCAATTGATCAGATAACCGGAAAGTTAAATAGACTCATTGA
GAAAACCAACCAGCAATTTGAGCTAATAGATAATGAATTCACTGAG
GTGGAAAAGCAGATTGGCAATTTAATTAACTGGACCAAAGACTCCA
TCACAGAAGTATGGTCTTACAATGCTGAACTTCTTGTGGCAATGGA
AAACCAGCACACTATTGATTTGGCTGATTCAGAGATGAACAAGCTG
TATGAGCGAGTGAGGAAACAATTAAGGGAAAATGCTGAAGAGGATG
GCACTGGTTGCTTTGAAATTTTTCATAAATGTGACGATGATTGTAT
GGCTAGTATAAGGAACAATACTTATGATCACAGCAAATACAGAGAA
GAAGCGATGCAAAATAGAATACAAATTGACCCAGTCAAATTGAGTA
GTGGCTACAAAGATGTGATACTTTGGTTTAGCTTCGGGGCATCATG
CTTTTTGCTTCTTGCCATTGCAATGGGCCTTGTTTTCATATGTGTG
AAGAACGGAAACATGCGGTGCACTATTTGTATATAA |
| 44 | Envelope;
RRV | AGTGTAACAGAGCACTTTAATGTGTATAAGGCTACTAGACCATACC
TAGCACATTGCGCCGATTGCGGGGACGGGTACTTCTGCTATAGCCC
AGTTGCTATCGAGGAGATCCGAGATGAGGCGTCTGATGGCATGCTT
AAGATCCAAGTCTCCGCCCAAATAGGTCTGGACAAGGCAGGCACCC
ACGCCCACACGAAGCTCCGATATATGGCTGGTCATGATGTTCAGGA
ATCTAAGAGAGATTCCTTGAGGGTGTACACGTCCGCAGCGTGCTCC
ATACATGGGACGATGGGACACTTCATCGTCGCACACTGTCCACCAG
GCGACTACCTCAAGGTTTCGTTCGAGGACGCAGATTCGCACGTGAA
GGCATGTAAGGTCCAATACAAGCACAATCCATTGCCGGTGGGTAGA |

-continued

Sequence Listings

| SEQ ID NO: | Description | Sequence |
| --- | --- | --- |
| | | GAGAAGTTCGTGGTTAGACCACACTTTGGCGTAGAGCTGCCATGCA<br>CCTCATACCAGCTGACAACGGCTCCCACCGACGAGGAGATTGACAT<br>GCATACACCGCCAGATATACCGGATCGCACCCTGCTATCACAGACG<br>GCGGGCAACGTCAAAATAACAGCAGGCGGCAGGACTATCAGGTACA<br>ACTGTACCTGCGGCCGTGACAACGTAGGCACTACCAGTACTGACAA<br>GACCATCAACACATGCAAGATTGACCAATGCCATGCTGCCGTCACC<br>AGCCATGACAAATGGCAATTTACCTCTCCATTTGTTCCCAGGGCTG<br>ATCAGACAGCTAGGAAAGGCAAGGTACACGTTCCGTTCCCTCTGAC<br>TAACGTCACCTGCCGAGTGCCGTTGGCTCGAGCGCCGGATGCCACC<br>TATGGTAAGAAGGAGGTGACCCTGAGATTACACCCAGATCATCCGA<br>CGCTCTTCTCCTATAGGAGTTTAGGAGCCGAACCGCACCCGTACGA<br>GGAATGGGTTGACAAGTTCTCTGAGCGCATCATCCCAGTGACGGAA<br>GAAGGGATTGAGTACCAGTGGGGCAACAACCCGCCGGTCTGCCTGT<br>GGGCGCAACTGACGACCGAGGGCAAACCCCATGGCTGGCCACATGA<br>AATCATTCAGTACTATTATGGACTATACCCCGCCGCCACTATTGCC<br>GCAGTATCCGGGGCGAGTCTGATGGCCCTCCTAACTCTGGCGGCCA<br>CATGCTGCATGCTGGCCACCGCGAGGAGAAAGTGCCTAACACCGTA<br>CGCCCTGACGCCAGGAGCGGTGGTACCGTTGACACTGGGGCTGCTT<br>TGCTGCGCACCGAGGGCGAATGCA |
| 45 | Envelope;<br>MLV 10A1 | ATGGAAGGTCCAGCGTTCTCAAAACCCCTTAAAGATAAGATTAACC<br>CGTGGAAGTCCTTAATGGTCATGGGGGTCTATTTAAGAGTAGGGAT<br>GGCAGAGAGCCCCCATCAGGTCTTTAATGTAACCTGGAGAGTCACC<br>AACCTGATGACTGGGCGTACCGCCAATGCCACCTCCCTTTTAGGAA<br>CTGTACAAGATGCCTTCCCAAGATTATATTTTGATCTATGTGATCT<br>GGTCGGAGAAGAGTGGGACCCTTCAGACCAGGAACCATATGTCGGG<br>TATGGCTGCAAATACCCCGGAGGGAGAAAGCGGACCCGGACTTTTG<br>ACTTTTACGTGTGCCCTGGGCATACCGTAAAATCGGGGTGTGGGGG<br>GCCAAGAGAGGGCTACTGTGGTGAATGGGGTTGTGAAACCACCGGA<br>CAGGCTTACTGGAAGCCCACATCATCATGGACCTAATCTCCCTTA<br>AGCGCGGTAACACCCCCTGGGACACGGGATGCTCCAAAATGGCTTG<br>TGGCCCCTGCTACGACCTCTCCAAAGTATCCAATTCCTTCCAAGGG<br>GCTACTCGAGGGGGCAGATGCAACCCTCTAGTCCTAGAATTCACTG<br>ATGCAGGAAAAAAGGCTAATTGGGACGGGCCCAAATCGTGGGGACT<br>GAGACTGTACCGGACAGGAACAGATCCTATTACCATGTTCTCCCTG<br>ACCCGCCAGGTCCTCAATATAGGGCCCCGCATCCCCATTGGGCCTA<br>ATCCCGTGATCACTGGTCAACTACCCCCCTCCCGACCCGTGCAGAT<br>CAGGCTCCCCAGGCCTCCTCAGCCTCCTCCTACAGGCGCAGCCTCT<br>ATAGTCCCTGAGACTGCCCCACCTTCTCAACAACCTGGGACGGGAG<br>ACAGGCTGCTAAACCTGGTAGAAGGAGCCTATCAGGCGCTTAACCT<br>CACCAATCCCGACAAGACCCAAGAATGTTGGCTGTGCTTAGTGTCG<br>GGACCTCCTTATTACGAAGGAGTAGCGGTCGTGGGCACTTATACCA<br>ATCATTCTACCGCCCCGGCCAGCTGTACGGCCACTTCCCAACATAA<br>GCTTACCCTATCTGAAGTGACAGGACAGGGCCTATGCATGGGAGCA<br>CTACCTAAAACTCACCAGGCCTTATGTAACACCACCCAAAGTGCCG<br>GCTCAGGATCCTACTACCTTGCAGCACCCGCTGGAACAATGTGGGC<br>TTGTAGCACTGGATTGACTCCCTGCTTGTCCACCACGATGCTCAAT<br>CTAACCACAGACTATTGTGTATTAGTTGAGCTCTGGCCCAGAATAA<br>TTTACCACTCCCCCGATTATATGTATGGTCAGCTTGAACAGCGTAC<br>CAAATATAAGAGGGAGCCAGTATCGTTGACCCTGGCCCTTCTGCTA<br>GGAGGATTAACCATGGGAGGGATTGCAGCTGGAATAGGGACGGGGA<br>CCACTGCCCTAATCAAAACCCAGCAGTTTGAGCAGCTTCACGCCGC<br>TATCCAGACAGACCTCAACGAAGTCGAAAAATCAATTACCAACCTA<br>GAAAAGTCACTGACCTCGTTGTCTGAAGTAGTCCTACAGAACCGAA<br>GAGGCCTAGATTTGCTCTTCCTAAAAGAGGGAGGTCTCTGCGCAGC<br>CCTAAAAGAAGAATGTTGTTTTTATGCAGACCACACGGGACTAGTG<br>AGAGACAGCATGGCCAAACTAAGGGAAAGGCTTAATCAGAGACAAA<br>AACTATTTGAGTCAGGCCAAGGTTGGTTCGAAGGGCAGTTTAATAG<br>ATCCCCCTGGTTTACCACCTTAATCTCCACCATCATGGGACCTCTA<br>ATAGTACTCTTACTGATCTTACTCTTTGGACCCTGCATTCTCAATC<br>GATTGGTCCAATTTGTTAAAGACAGGATCTCAGTGGTCCAGGCTCT<br>GGTTTTGACTCAACAATATCACCAGCTAAAACCTATAGAGTACGAG<br>CCATGA |
| 46 | Envelope;<br>Ebola | ATGGGTGTTACAGGAATATTGCAGTTACCTCGTGATCGATTCAAGA<br>GGACATCATTCTTTCTTTGGGTAATTATCCTTTTCCAAAGAACATT<br>TTCCATCCCACTTGGAGTCATCCACAATAGCACATTACAGGTTAGT<br>GATGTCGACAAACTGGTTTGCCGTGACAAACTGTCATCCACAAATC<br>AATTGAGATCAGTTGGACTGAATCTCGAAGGGAATGGAGTGGCAAC<br>TGACGTGCCATCTGCAACTAAAAGATGGGGCTTCAGGTCCGGTGTC<br>CCACCAAAGGTGGTCAATTATGAAGCTGGTGAATGGGCTGAAAACT<br>GCTACAATCTTGAAATCAAAAAACCTGACGGGAGTGAGTGTCTACC<br>AGCAGCGCCAGACGGGATTCGGGGCTTCCCCCGGTGCCGGTATGTG<br>CACAAAGTATCAGGAACGGGACCGTGTGCCGGAGACTTTGCCTTCC<br>ACAAAGAGGGTGCTTTCTTCCTGTATGACCGACTTGCTTCCACAGT |

| SEQ ID NO: | Description | Sequence |
|---|---|---|
| | | TATCTACCGAGGAACGACTTTCGCTGAAGGTGTCGTTGCATTTCTG
ATACTGCCCCAAGCTAAGAAGGACTTCTTCAGCTCACACCCCTTGA
GAGAGCCGGTCAATGCAACGGAGGACCCGTCTAGTGGCTACTATTC
TACCACAATTAGATATCAAGCTACCGGTTTTGGAACCAATGAGACA
GAGTATTTGTTCGAGGTTGACAATTTGACCTACGTCCAACTTGAAT
CAAGATTCACACCACAGTTTCTGCTCCAGCTGAATGAGACAATATA
TACAAGTGGGAAAAGGAGCAATACCACGGGAAAACTAATTTGGAAG
GTCAACCCCGAAATTGATACAACAATCGGGGAGTGGGCCTTCTGGG
AAACTAAAAAAACCTCACTAGAAAAATTCGCAGTGAAGAGTTGTCT
TTCACAGCTGTATCAAACAGAGCCAAAAACATCAGTGGTCAGAGTC
CGGCGCGAACTTCTTCCGACCCAGGGACCAACACAACAACTGAAGA
CCACAAAATCATGGCTTCAGAAAATTCCTCTGCAATGGTTCAAGTG
CACAGTCAAGGAAGGGAAGCTGCAGTGTCGCATCTGACAACCCTTG
CCACAATCTCCACGAGTCCTCAACCCCCCACAACCAAACCAGGTCC
GGACAACAGCACCCACAATACACCCGTGTATAAACTTGACATCTCT
GAGGCAACTCAAGTTGAACAACATCACCGCAGAACAGACAACGACA
GCACAGCCTCCGACACTCCCCCCGCCACGACCGCAGCCGGACCCCT
AAAAGCAGAGAACACCAACACGAGCAAGGGTACCGACCTCCTGGAC
CCCGCCACCACAACAAGTCCCCAAAACCACAGCGAGACCGCTGGCA
ACAACAACACTCATCACCAAGATACCGGAGAAGAGAGTGCCAGCAG
CGGGAAGCTAGGCTTAATTACCAATACTATTGCTGGAGTCGCAGGA
CTGATCACAGGCGGGAGGAGAGCTCGAAGAGAAGCAATTGTCAATG
CTCAACCCAAATGCAACCCTAATTTACATTACTGGACTACTCAGGA
TGAAGGTGCTGCAATCGGACTGGCCTGGATACCATATTTCGGGCCA
GCAGCCGAGGGAATTTACATAGAGGGGCTGATGCACAATCAAGATG
GTTTAATCTGTGGGTTGAGACAGCTGGCCAACGAGACGACTCAGG
TCTTCAACTGTTCCTGAGAGCCACAACCGAGCTACGCACCTTTTCA
ATCCTCAACCGTAAGGCAATTGATTTCTTGCTGCAGCGATGGGGCG
GCACATGCCACATTTTGGGACCGGACTGCTGTATCGAACCACATGA
TTGGACCAAGAACATAACAGACAAAATTGATCAGATTATTCATGAT
TTTGTTGATAAAACCCTTCCGGACCAGGGGGACAATGACAATTGGT
GGACAGGATGGAGACAATGGATACCGGCAGGTATTGGAGTTACAGG
CGTTATAATTGCAGTTATCGCTTTATTCTGTATATGCAAATTTGTC
TTTTAG |
| 47 | Left ITR | CCTGCAGGCAGCTGCGCGCTCGCTCGCTCACTGAGGCCGCCCGGGC
AAAGCCCGGGCGTCGGGCGACCTTTGGTCGCCCGGCCTCAGTGAGC
GAGCGAGCGCGCAGAGAGGGAGTGGCCAACTCCATCACTAGGGGTT
CCT |
| 48 | Prothrombin enhancer | GCGAGAACTTGTGCCTCCCCGTGTTCCTGCTCTTTGTCCCTCTGTC
CTACTTAGACTAATATTTGCCTTGGGTACTGCAAACAGGAAATGGG
GGAGGGACAGGAGTAGGGCGGAGGGTAG |
| 49 | PolyA | GACTGTGCCTTCTAGTTGCCAGCCATCTGTTGTTTGCCCCTCCCCC
GTGCCTTCCTTGACCCTGGAAGGTGCCACTCCCACTGTCCTTTCCT
AATAAAATGAGGAAATTGCATCGCATTGTCTGAGTAGGTGTCATTC
TATTCTGGGGGGTGGGGTGGGGCAGGACAGCAAGGGGGAGGATTGG
GAAGACAATAGCAGGCATGCTGGGGATGCGGTGGGCTCTATGGC |
| 50 | Right ITR | AGGAACCCCTAGTGATGGAGTTGGCCACTCCCTCTCTGCGCGCTCG
CTCGCTCACTGAGGCCGGGCGACCAAAGGTCGCCCGACGCCCGGGC
TTTGCCCGGGCGGCCTCAGTGAGCGAGCGAGCGCGCAGCTGCCTGC
AGG |
| 51 | E2A | TTAAAAGTCGAAGGGGTTCTCGCGCTCGTCGTTGTGCGCCGCGCTG
GGGAGGGCCACGTTGCGGAACTGGTACTTGGGCTGCCACTTGAACT
CGGGGATCACCAGTTTGGGCACTGGGGTCTCGGGGAAGGTCTCGCT
CCACATGCGCCGGCTCATCTGCAGGGCGCCCAGCATGTCAGGCGCG
GAGATCTTGAAATCGCAGTTGGGGCCGGTGCTCTGCGCGCGCGAGT
TGCGGTACACTGGGTTGCAGCACTGGAACACCATCAGACTGGGGTA
CTTCACACTAGCCAGCACGCTCTTGTCGCTGATCTGATCCTTGTCC
AGGTCCTCGGCGTTGCTCAGGCCGAACGGGGTCATCTTGCACAGCT
GGCGGCCCAGGAAGGGCACGCTCTGAGGCTTGTGGTTACACTCGCA
GTGCACGGGCATCAGCATCATCCCCGCGCCGCGCTGCATATTCGGG
TAGAGGGCCTTGACGAAGGCCGCGATCTGCTTGAAAGCTTGCTGGG
CCTTGGCCCCCTCGCTGAAAAACAGGCCGCAGCTCTTCCCGCTGAA
CTGATTATTCCCGCACCCGGCATCATGGACGCAGCAGCGCGCGTCA
TGGCTGGTCAGTTGCACCACGCTCCGTCCCCAGCGGTTCTGGGTCA
CCTTGGCCTTGCTGGGTTGCTCCTTCAGCGCACGCTGCCCGTTCTC
ACTGGTCACATCCATCTCCACCACGTGGTCCTTGTGGATCATCACC
GTCCCATGCAGACACTTGAGCTGGCCTTCCACCTCGGTGCAGCCGT
GGTCCCACAGGGCACTGCCGGTGCACTCCCAGTTCTTGTGCGCGAT
CCCGCTGTGGCTGAAGATGTAACCTTGCAACAGGCGACCCATGATG
GTGCTAAAGCTCTTCTGGGTGGTGAAGGTCAGTTGCAGACCGCGGG |

| SEQ ID NO: | Description | Sequence |
|---|---|---|
| | | CCTCCTCGTTCATCCAGGTCTGGCACATCTTTTGGAAGATCTCGGT<br>CTGCTCGGGCATGAGCTTGTAAGCATCGCGCAGGCCGCTGTCGACG<br>CGGTAGCGTTCCATCAGCACATTCATGGTATCCATGCCCTTCTCCC<br>AGGACGAGACCAGAGGCAGACTCAGGGGGTTGCGCACGTTCAGGAC<br>ACCGGGGGTCGCGGGCTCGACGATGCGTTTTCCGTCCTTGCCTTCC<br>TTCAACAGAACCGGCGGCTGGCTGAATCCCACTCCCACGATCACGG<br>CTTCTTCCTGGGGCATCTCTTCGTCTGGGTCTACCTTGGTCACATG<br>CTTGGTCTTTCTGGCTTGCTTCTTTTTTGGAGGGCTGTCCACGGGG<br>ACCACGTCCTCCTCGGAAGACCCGGATCCCACCCGCTGATACTTTC<br>GGCGCTTGGTTGGCAGAGGAGGTGGCGGCGAGGGGCTCCTCTCCTG<br>CTCCGGCGGATAGCGCGCTGAACCGTGGCCCCGGGGCGGAGTGGCC<br>TCTCGGTCCATGAACCGGCGCACGTCCTGACTGCCGCCGGCCAT |
| 52 | E4 | TCATGTATCTTTATTGATTTTTACACCAGCACGGGTAGTCAGTCTC<br>CCACCACCAGCCCCATTTCACAGTGTAAACAATTCTCTCAGCACGGG<br>TGGCCTTAAATAGGGCAATATTCTGATTAGTGCGGGAACTGGACTT<br>GGGGTCTATAATCCACACAGTTTCCTGGCGAGCCAAACGGGGGTCG<br>GTGATTGAGATGAAGCCGTCCTCTGAAAAGTCATCCAAGCGAGCCT<br>CACAGTCCAAGGTCACAGTATTATGATAATCTGCATGATCACAATC<br>GGGCAACAGGGGATGTTGTTCAGTCAGTGAAGCCCTGGTTTCCTCA<br>TCAGATCGTGGTAAACGGGCCCTGCGATATGGATGATGGCGGAGCG<br>AGCTGGATTGAATCTCGGTTTGCAT |
| 53 | VA RNA | AGCGGGCACTCTTCCGTGGTCTGGTGGATAAATTCGCAAGGGTATC<br>ATGGCGGACGACCGGGGTTCGAGCCCCGTATCCGGCCGTCCGCCGT<br>GATCCATGCGGTTACCGCCCGCGTGTCGAACCCAGGTGTGCGACGT<br>CAGACAACGGGGGAGTGCTCCTTT |
| 54 | AAV2 Rep | ATGGCTGCCGATGGTTATCTTCCAGATTGGCTCGAGGACACTCTCT<br>CTGAAGGAATAAGACAGTGGTGGAAGCTCAAACCTGGCCCACCACC<br>ACCAAAGCCCGCAGAGCGGCATAAGGACGACAGCAGGGGTCTTGTG<br>CTTCCTGGGTACAAGTACCTCGGACCCTTCAACGGACTCGACAAGG<br>GAGAGCCGGTCAACGAGGCAGACGCCGCGGCCCTCGAGCACGACAA<br>AGCCTACGACCGGCAGCTCGACAGCGGAGACAACCCGTACCTCAAG<br>TACAACCACGCCGACGCGGAGTTTCAGGAGCGCCTTAAAGAAGATA<br>CGTCTTTTGGGGGCAACCTCGGACGAGCAGTCTTCCAGGCGAAAAA<br>GAGGGTTCTTGAACCTCTGGGCCTGGTTGAGGAACCTGTTAAGACG<br>GCTCCGGGAAAAAAGAGGCCGGTAGAGCACTCTCCTGTGGAGCCAG<br>ACTCCTCCTCGGGAACCGGAAAGGCGGGCCAGCAGCCTGCAAGAAA<br>AAGATTGAATTTTGGTCAGACTGGAGACGCAGACTCAGTACCTGAC<br>CCCCAGCCTCTCGGACAGCCACCAGCAGCCCCCTCTGGTCTGGGAA<br>CTAATACGATGGCTACAGGCAGTGGCGCACCAATGGCAGACAATAA<br>CGAGGGCGCCGACGGAGTGGGTAATTCCTCGGGAAATTGGCATTGC<br>GATTCCACATGGATGGGCGACAGAGTCATCACCACCAGCACCCGAA<br>CCTGGGCCCTGCCCACCTACAACAACCACCTCTACAAACAAATTTC<br>CAGCCAATCAGGAGCCTCGAACGACAATCACTACTTTGGCTACAGC<br>ACCCCTTGGGGGTATTTTGACTTCAACAGATTCCACTGCCACTTTT<br>CACCACGTGACTGGCAAAGACTCATCAACAACAACTGGGGATTCCG<br>ACCCAAGAGACTCAACTTCAAGCTCTTTAACATTCAAGTCAAAGAG<br>GTCACGCAGAATGACGGTACGACGACGATTGCCAATAACCTTACCA<br>GCACGGTTCAGGTGTTTACTGACTCGGAGTACCAGCTCCCGTACGT<br>CCTCGGCTCGGCGCATCAAGGATGCCTCCCGCCGTTCCCAGCAGAC<br>GTCTTCATGGTGCCACAGTATGGATACCTCACCCTGAACAACGGGA<br>GTCAGGCAGTAGGACGCTCTTCATTTTACTGCCTGGAGTACTTTCC<br>TTCTCAGATGCTGCGTACCGGAAACAACTTTACCTTCAGCTACACT<br>TTTGAGGACGTTCCTTTCCACAGCAGCTACGCTCACAGCCAGAGTC<br>TGGACCGTCTCATGAATCCTCTCATCGACCAGTACCTGTATTACTT<br>GAGCAGAACAAACACTCCAAGTGGAACCACCACGCAGTCAAGGCTT<br>CAGTTTTCTCAGGCCGGAGCGAGTGACATTCGGGACCAGTCTAGGA<br>ACTGGCTTCCTGGACCCTGTTACCGCCAGCAGCGAGTATCAAAGAC<br>ATCTGCGGATAACAACAGTGAATACTCGTGGACTGGAGCTACC<br>AAGTACCACCTCAATGGCAGAGACTCTCTGGTGAATCCGGGCCCGG<br>CCATGGCAAGCCACAAGGACGATGAAGAAAAGTTTTTTCCTCAGAG<br>CGGGGTTCTCATCTTTGGGAAGCAAGGCTCAGAGAAAACAAATGTG<br>GACATTGAAAAGGTCATGATTACAGACGAAGAGGAAATCAGGACAA<br>CCAATCCCGTGGCTACGGAGCAGTATGGTTCTGTATCTACCAACCT<br>CCAGAGAGGCAACAGACAAGCAGCTACCGCAGATGTCAACACACAA<br>GGCGTTCTTCCAGGCATGGTCTGGCAGGACAGAGATGTGTACCTTC<br>AGGGGCCCATCTGGGCAAAGATTCCACACACGGACGGACATTTTCA<br>CCCCTCTCCCCTCATGGGTGGATTCGGACTTAAACACCCTCCTCCA<br>CAGATTCTCATCAAGAACACCCCGGTACCTGCGAATCCTTCGACCA<br>CCTTCAGTGCGGCAAAGTTTGCTTCCTTCATCACACAGTACTCCAC |

| SEQ ID NO: | Description | Sequence |
|---|---|---|
| | | GGGACAGGTCAGCGTGGAGATCGAGTGGGAGCTGCAGAAGGAAAAC<br>AGCAAACGCTGGAATCCCGAAATTCAGTACACTTCCAACTACAACA<br>AGTCTGTTAATGTGGACTTTACTGTGGACACTAATGGCGTGTATTC<br>AGAGCCTCGCCCCATTGGCACCAGATACCTGACTCGTAATCTGTAA |
| 55 | AAV2 Cap | ATGCCGGGGTTTTACGAGATTGTGATTAAGGTCCCCAGCGACCTTG<br>ACGAGCATCTGCCCGGCATTTCTGACAGCTTTGTGAACTGGGTGGC<br>CGAGAAGGAATGGGAGTTGCCGCCAGATTCTGACATGGATCTGAAT<br>CTGATTGAGCAGGCACCCCTGACCGTGGCCGAGAAGCTGCAGCGCG<br>ACTTTCTGACGGAATGGCGCCGTGTGAGTAAGGCCCCGGAGGCCCT<br>TTTCTTTGTGCAATTTGAGAAGGGAGAGAGCTACTTCCACATGCAC<br>GTGCTCGTGGAAACCACCGGGGTGAATCCATGGTTTTGGGACGTT<br>TCCTGAGTCAGATTCGCGAAAAACTGATTCAGAGAATTTACCGCGG<br>GATCGAGCCGACTTTGCCAAACTGGTTCGCGGTCACAAAGACCAGA<br>AATGGCGCCGGAGGCGGGAACAAGGTGGTGGATGAGTGCTACATCC<br>CCAATTACTTGCTCCCCAAAACCCAGCCTGAGCTCCAGTGGGCGTG<br>GACTAATATGGAACAGTATTTAAGCGCCTGTTTGAATCTCACGGAG<br>CGTAAACGGTTGGTGGCGCAGCATCTGACGCACGTGTCGCAGACGC<br>AGGAGCAGAACAAAGAGAATCAGAATCCCAATTCTGATGCGCCGGT<br>GATCAGATCAAAAACTTCAGCCAGGTACATGGAGCTGGTCGGGTGG<br>CTCGTGGACAAGGGGATTACCTCGGAGAAGCAGTGGATCCAGGAGG<br>ACCAGGCCTCATACATCTCCTTCAATGCGGCCTCCAACTCGCGGTC<br>CCAAATCAAGGCTGCCTTGGACAATGCGGGAAAGATTATGAGCCTG<br>ACTAAAACCGCCCCCGACTACCTGGTGGGCCAGCAGCCCGTGGAGG<br>ACATTTCCAGCAATCGGATTTATAAAATTTTGGAACTAAACGGGTA<br>CGATCCCCAATATGCGGCTTCCGTCTTTCTGGGATGGGCCACGAAA<br>AAGTTCGGCAAGAGGAACACCATCTGGCTGTTTGGGCCTGCAACTA<br>CCGGGAAGACCAACATCGCGGAGGCCATAGCCCACACTGTGCCCTT<br>CTACGGGTGCGTAAACTGGACCAATGAGAACTTTCCCTTCAACGAC<br>TGTGTCGACAAGATGGTGATCTGGTGGGAGGAGGGGAAGATGACCG<br>CCAAGGTCGTGGAGTCGGCCAAAGCCATTCTCGGAGGAAGCAAGGT<br>GCGCGTGGACCAGAAATGCAAGTCCTCGGCCCAGATAGACCCGACT<br>CCCGTGATCGTCACCTCCAACACCAACATGTGCGCCGTGATTGACG<br>GGAACTCAACGACCTTCGAACACCAGCAGCCGTTGCAAGACCGGAT<br>GTTCAAATTTGAACTCACCCGCCGTCTGGATCATGACTTTGGGAAG<br>GTCACCAAGCAGGAAGTCAAAGACTTTTTCCGGTGGGCAAAGGATC<br>ACGTGGTTGAGGTGGAGCATGAATTCTACGTCAAAAAGGGTGGAGC<br>CAAGAAAAGACCCGCCCCCAGTGACGCAGATATAAGTGAGCCCAAA<br>CGGGTGCGCGAGTCAGTTGCGCAGCCATCGACGTCAGACGCGGAAG<br>CTTCGATCAACTACGCAGACAGGTACCAAAACAAATGTTCTCGTCA<br>CGTGGGCATGAATCTGATGCTGTTTCCCTGCAGACAATGCGAGAGA<br>ATGAATCAGAATTCAAATATCTGCTTCACTCACGGACAGAAAGACT<br>GTTTAGAGTGCTTTCCCGTGTCAGAATCTCAACCCGTTTCTGTCGT<br>CAAAAAGGCGTATCAGAAACTGTGCTACATTCATCATATCATGGGA<br>AAGGTGCCAGACGCTTGCACTGCCTGCGATCTGGTCAATGTGGATT<br>TGGATGACTGCATCTTTGAACAATAA |
| 56 | DNA Fragment containing RRE and rabbit beta globin poly A | TCTAGAAGGAGCTTTGTTCCTTGGGTTCTTGGGAGCAGCAGGAAGC<br>ACTATGGGCGCAGCGTCAATGACGCTGACGGTACAGGCCAGACAAT<br>TATTGTCTGGTATAGTGCAGCAGCAGAACAATTTGCTGAGGGCTAT<br>TGAGGCGCAACAGCATCTGTTGCAACTCACAGTCTGGGGCATCAAG<br>CAGCTCCAGGCAAGAATCCTGGCTGTGAAAGATACCTAAAGGATC<br>AACAGCTCCTAGATCTTTTTCCCTCTGCCAAAAATTATGGGGACAT<br>CATGAAGCCCCTTGAGCATCTGACTTCTGGCTAATAAAGGAAATTT<br>ATTTTCATTGCAATAGTGTGTTGGAATTTTTTGTGTCTCTCACTCG<br>GAAGGACATATGGGAGGGCAAATCATTTAAAACATCAGAATGAGTA<br>TTTGGTTTAGAGTTTGGCAACATATGCCATATGCTGGCTGCCATGA<br>ACAAAGGTGGCTATAAAGAGGTCATCAGTATATGAAACAGCCCCCT<br>GCTGTCCATTCCTTATTCCATAGAAAGCCTTGACTTGAGGTTAGA<br>TTTTTTTTATATTTTGTTTTGTGTTATTTTTTCTTTAACATCCCT<br>AAAATTTTCCTTACATGTTTTACTAGCCAGATTTTCCTCCTCTCC<br>TGACTACTCCCAGTCATAGCTGTCCCTCTTCTCTTATGAAGATCCC<br>TCGACCTGCAGCCCAAGCTTGGCGTAATCATGGTCATAGCTGTTTC<br>CTGTGTGAAATTGTTATCCGCTCACAATTCCACACAACATACGAGC<br>CGGAAGCATAAAGTGTAAAGCCTGGGGTGCCTAATGAGTGAGCTAA<br>CTCACATTAATTGCGTTGCGCTCACTGCCCGCTTTCCAGTCGGGAA<br>ACCTGTCGTGCCAGCGGATCCGCATCTCAATTAGTCAGCAACCATA<br>GTCCCGCCCCTAACTCCGCCCATCCCGCCCCTAACTCCGCCCAGTT<br>CCGCCCATTCTCCGCCCCATGGCTGACTAATTTTTTTATTTATGC<br>AGAGGCCGAGGCCGCCTCGGCCTCTGAGCTATTCCAGAAGTAGTGA<br>GGAGGCTTTTTTGGAGGCCTAGGCTTTTGCAAAAAGCTAACTTGTT<br>TATTGCAGCTTATAATGGTTACAAATAAAGCAATAGCATCACAAAT<br>TTCACAAATAAAGCATTTTTTTCACTGCATTCTAGTTGTGGTTTGT<br>CCAAACTCATCAATGTATCTTATCACCCGGG |

| SEQ ID NO: | Description | Sequence |
|---|---|---|
| 57 | hPAH with full 5' and 3' UTR | GGCACGAGGTACCTGAGGCCCTAAAAAGCCAGAGACCTCACTCCCG GGGAGCCAGCATGTCCACTGCGGTCCTGGAAAACCCAGGCTTGGGC AGGAAACTCTCTGACTTTGGACAGGAAACAAGCTATATTGAAGACA ACTGCAATCAAAATGGTGCCATATCACTGATCTTCTCACTCAAAGA AGAAGTTGGTGCATTGGCCAAAGTATTGCGCTTATTTGAGGAGAAT GATGTAAACCTGACCCACATTGAATCTAGACCTTCTCGTTTAAAGA AAGATGAGTATGAATTTTTCACCCATTTGGATAAACGTAGCCTGCC TGCTCTGACAAACATCATCAAGATCTTGAGGCATGACATTGGTGCC ACTGTCCATGAGCTTTCACGAGATAAGAAGAAAGACACAGTGCCCT GGTTCCCAAGAACCATTCAAGAGCTGGACAGATTTGCCAATCAGAT TCTCAGCTATGGAGCGGAACTGGATGCTGACCACCCTGGTTTTAAA GATCCTGTGTACCGTGCAAGACGGAAGCAGTTTGCTGACATTGCCT ACAACTACCGCCATGGGCAGCCCATCCCTCGAGTGGAATACATGGA GGAAGAAAAGAAAACATGGGGCACAGTGTTCAAGACTCTGAAGTCC TTGTATAAAACCCATGCTTGCTATGAGTACAATCACATTTTTCCAC TTCTTGAAAAGTACTGTGGCTTCCATGAAGATAACATTCCCCAGCT GGAAGACGTTTCTCAGTTCCTGCAGACTTGCACTGGTTTCCGCCTC CGACCTGTAGCTGGCCTGCTTTCCTCTCGGGATTTCTTGGGTGGCC TGGCCTTCCGAGTCTTCCACTGCACACAGTACATCAGACATGGATC CAAGCCCATGTATACCCCCGAACCTGACATCTGCCATGAGCTGTTG GGACATGTGCCCTTGTTTTCAGATCGCAGCTTTGCCCAGTTTTCCC AGGAAATTGGCCTTGCCTCTCTGGGTGCACCTGATGAATACATTGA AAAGCTCGCCACAATTTACTGGTTTACTGTGGAGTTTGGGCTCTGC AAACAAGGAGACTCCATAAAGGCATATGGTGCTGGGCTCCTGTCAT CCTTTGGTGAATTACAGTACTGCTTATCAGAGAAGCCAAAGCTTCT CCCCCTGGAGCTGGAGAAGACAGCCATCCAAAATTACACTGTCACG GAGTTCCAGCCCCTGTATTACGTGGCAGAGAGTTTTAATGATGCCA AGGAGAAAGTAAGGAACTTTGCTGCCACAATACCTCGGCCCTTCTC AGTTCGCTACGACCCATACACCCAAAGGATTGAGGTCTTGGACAAT ACCCAGCAGCTTAAGATTTTGGCTGATTCCATTAACAGTGAAATTG GAATCCTTTGCAGTGCCCTCCAGAAAATAAAGTAAAGCCATGGACA GAATGTGGTCTGTCAGCTGTGAATCTGTTGATGGAGATCCAACTAT TTCTTTCATCAGAAAAGTCCGAAAAGCAAACCTTAATTTGAAATA ACAGCCTTAAATCCTTTACAAGATGGAGAAACAACAAATAAGTCAA AATAATCTGAAATGACAGGATATGAGTACATACTCAAGAGCATAAT GGTAAATCTTTTGGGGTCATCTTTGATTTAGAGATGATAATCCCAT ACTCTCAATTGAGTTAAATCAGTAATCTGTCGCATTTCATCAAGAT TAATTAAAATTTGGGACCTGCTTCATTCAAGCTTCATATATGCTTT GCAGAGAACTCATAAAGGAGCATATAAGGCTAAATGTAAAACCCAA GACTGTCATTAGAATTGAATTATTGGGCTTAATATAAATCGTAACC TATGAAGTTTATTTTTTATTTTAGTTAACTATGATTCCAATTACTA CTTTGTTATTGTACCTAAGTAAATTTTCTTTAAGTCAGAAGCCCAT TAAAATAGTTACAAGCATTGAACTTCTTTAGTATTATATTAATATA AAAACATTTTTGTATGTTTTATTGTAATCATAAATACTGCTGTATA AGGTAATAAAACTCTGCACCTAATCCCCATAACTTCCAGTATCATT TTCCAATTAATTATCAAGTCTGTTTTGGGAAACACTTTGAGGACAT TTATGATGCAGCAGATGTTGACTAAAGGCTTGGTTGGTAGATATTC AGGAAATGTTCACTGAATAAATAAGTAAATACATTATTGAAAAGCA AATCTGTATAAATGTGAAATTTTTATTTGTATTAGTAATAAAACAT TAGTAGTTTAAACAAAAAAAAAAAAAAAAAAAAAAAAAAAAAACT CGACTCTAGATT |
| 58 | hPAH with full 5' UTR and truncated 3' UTR | GGCACGAGGTACCTGAGGCCCTAAAAAGCCAGAGACCTCACTCCCG GGGAGCCAGCATGTCCACTGCGGTCCTGGAAAACCCAGGCTTGGGC AGGAAACTCTCTGACTTTGGACAGGAAACAAGCTATATTGAAGACA ACTGCAATCAAAATGGTGCCATATCACTGATCTTCTCACTCAAAGA AGAAGTTGGTGCATTGGCCAAAGTATTGCGCTTATTTGAGGAGAAT GATGTAAACCTGACCCACATTGAATCTAGACCTTCTCGTTTAAAGA AAGATGAGTATGAATTTTTCACCCATTTGGATAAACGTAGCCTGCC TGCTCTGACAAACATCATCAAGATCTTGAGGCATGACATTGGTGCC ACTGTCCATGAGCTTTCACGAGATAAGAAGAAAGACACAGTGCCCT GGTTCCCAAGAACCATTCAAGAGCTGGACAGATTTGCCAATCAGAT TCTCAGCTATGGAGCGGAACTGGATGCTGACCACCCTGGTTTTAAA GATCCTGTGTACCGTGCAAGACGGAAGCAGTTTGCTGACATTGCCT ACAACTACCGCCATGGGCAGCCCATCCCTCGAGTGGAATACATGGA GGAAGAAAAGAAAACATGGGGCACAGTGTTCAAGACTCTGAAGTCC TTGTATAAAACCCATGCTTGCTATGAGTACAATCACATTTTTCCAC TTCTTGAAAAGTACTGTGGCTTCCATGAAGATAACATTCCCCAGCT GGAAGACGTTTCTCAGTTCCTGCAGACTTGCACTGGTTTCCGCCTC CGACCTGTAGCTGGCCTGCTTTCCTCTCGGGATTTCTTGGGTGGCC TGGCCTTCCGAGTCTTCCACTGCACACAGTACATCAGACATGGATC CAAGCCCATGTATACCCCCGAACCTGACATCTGCCATGAGCTGTTG GGACATGTGCCCTTGTTTTCAGATCGCAGCTTTGCCCAGTTTTCCC AGGAAATTGGCCTTGCCTCTCTGGGTGCACCTGATGAATACATTGA AAAGCTCGCCACAATTTACTGGTTTACTGTGGAGTTTGGGCTCTGC |

| Sequence Listings | |
|---|---|
| SEQ ID NO: Description | Sequence |
| | AAACAAGGAGACTCCATAAAGGCATATGGTGCTGGGCTCCTGTCAT<br>CCTTTGGTGAATTACAGTACTGCTTATCAGAGAAGCCAAAGCTTCT<br>CCCCCTGGAGCTGGAGAAGACAGCCATCCAAAATTACACTGTCACG<br>GAGTTCCAGCCCCTGTATTACGTGGCAGAGAGTTTTAATGATGCCA<br>AGGAGAAAGTAAGGAACTTTGCTGCCACAATACCTCGGCCCTTCTC<br>AGTTCGCTACGACCCATACACCCAAAGGATTGAGGTCTTGGACAAT<br>ACCCAGCAGCTTAAGATTTTGGCTGATTCCATTAACAGTGAAATTG<br>GAATCCTTTGCAGTGCCCTCCAGAAAATAAAGTAAAGCCATGGACA<br>GAATGTGGTCTGTCAGCTGTGAATCTGTTGATGGAGATCCAACTAT<br>TTCTTTCATCAGAAAAGTCCGAAAAGCAAACCTTAATTTGAAATA<br>ACAGCCTTAAATCCTTTACAAGATGGAGAAACAACAAATAAGTCAA<br>AATAATCTGAAATGACAGGATATGAGTACATACTCAAGAGCATAAT<br>GGTAAATCTTTTGGGGTCATCTTTGATTTAGAGATGATAATCCCAT<br>ACTCTCAATTGAGTTAAATCAGTAATCTGTCGCATTTCATCAAGAT<br>TA |

What is claimed is:

1. A viral vector comprising:

a phenylalanine hydroxylase (PAH) sequence for expressing at least one of PAH or a variant thereof, wherein the PAH sequence is truncated, wherein the truncated sequence is SEQ ID NO: 3, SEQ ID NO: 4, or a sequence that has 80%, 85%, 90%, 95%, or 100% identity to SEQ ID NO: 3 or SEQ ID NO: 4.

2. The viral vector of claim 1, further comprising:

at least one small RNA sequence that is capable of binding to at least one pre-determined complementary mRNA sequence.

3. The viral vector of claim 2, wherein the at least one small RNA sequence is under the control of a first promoter, and wherein the PAH sequence is under the control of a second promoter.

4. The viral vector of claim 3, wherein the first promoter comprises a H1 promoter and wherein the second promoter comprises a liver-specific promoter.

5. The viral vector of claim 4, wherein the liver-specific promoter comprises a hAAT promoter.

6. The viral vector of claim 2, wherein the at least one small RNA sequence comprises a sequence having at least one of 80%, 85%, 90%, 95%, or 100% identity with at least one of SEQ ID NO: 5 or SEQ ID NO: 6.

* * * * *